United States Patent
Lockwood

(10) Patent No.: US 9,180,111 B2
(45) Date of Patent: *Nov. 10, 2015

(54) REDUCTION IN COMPLEMENT ACTIVATION AND INFLAMMATION DURING TISSUE INJURY BY CAROTENOIDS, CAROTENOID ANALOGS, OR DERIVATIVES THEREOF

(71) Applicants: Cardax Pharma, Inc., Honolulu, HI (US); Cardax Pharmaceuticals, Inc., Honolulu, HI (US)

(72) Inventor: Samuel F. Lockwood, Calumet, MI (US)

(73) Assignee: Cardax Pharma, Inc., Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,876

(22) Filed: Jun. 19, 2013

(65) Prior Publication Data

US 2014/0005151 A1 Jan. 2, 2014

Related U.S. Application Data

(63) Continuation of application No. 11/392,470, filed on Mar. 29, 2006, now abandoned.

(60) Provisional application No. 60/666,119, filed on Mar. 29, 2005.

(51) Int. Cl.

| | | |
|---|---|---|
| A61K 31/195 | (2006.01) |
| A61K 31/225 | (2006.01) |
| A61K 31/197 | (2006.01) |
| A61K 38/16 | (2006.01) |
| A61K 45/06 | (2006.01) |
| A61K 31/215 | (2006.01) |
| A61K 31/221 | (2006.01) |
| A61K 31/192 | (2006.01) |
| A61K 31/341 | (2006.01) |
| A61K 31/573 | (2006.01) |
| A61K 31/6615 | (2006.01) |
| A61K 31/7034 | (2006.01) |

(52) U.S. Cl.
CPC ............. *A61K 31/225* (2013.01); *A61K 31/192* (2013.01); *A61K 31/195* (2013.01); *A61K 31/341* (2013.01); *A61K 31/573* (2013.01); *A61K 31/6615* (2013.01); *A61K 31/7034* (2013.01); *A61K 38/16* (2013.01); *A61K 45/06* (2013.01)

(58) Field of Classification Search
CPC . A61K 31/195; A61K 31/225; A61K 31/197; A61K 38/16; A61K 45/06; A61K 31/215; A61K 31/221

See application file for complete search history.

(56) References Cited

U.S. PATENT DOCUMENTS

| | | |
|---|---|---|
| 4,176,179 A | 11/1979 | Gainer |
| 4,491,574 A | 1/1985 | Seifter et al. |
| 5,536,504 A | 7/1996 | Eugster et al. |
| 5,801,159 A | 9/1998 | Miller et al. |
| 6,051,587 A | 4/2000 | Dakashinamurti et al. |
| 6,245,818 B1 | 6/2001 | Lignell |
| 6,258,855 B1 | 7/2001 | Lorenz et al. |
| 6,426,362 B1 | 7/2002 | Miller et al. |
| 6,540,654 B2 | 4/2003 | Levy et al. |
| 7,521,584 B2 * | 4/2009 | Lockwood et al. ............ 585/351 |
| 7,592,449 B2 * | 9/2009 | Lockwood et al. ............ 544/106 |
| 2004/0043992 A1 * | 3/2004 | Tolba et al. ................. 514/226.5 |
| 2004/0044028 A1 * | 3/2004 | Obukowicz .................... 514/303 |
| 2004/0076691 A1 * | 4/2004 | Haines et al. .................. 424/729 |
| 2005/0026874 A1 * | 2/2005 | Lockwood et al. ........... 514/143 |

FOREIGN PATENT DOCUMENTS

| | | |
|---|---|---|
| JP | 7300421 | 11/1995 |
| WO | 99/11251 | 3/1999 |
| WO | 03/066583 | 8/2003 |

OTHER PUBLICATIONS

Holtin et al. "Determination of astaxanthin and astaxanthin esters in the microalgae *Haematococcus pluvialis* by LC-(APCI)MS and characterization of predominant carotenoid isomers by NMR spectroscopy" Anal. Bioanal. Chem. 2009, 395(6): 1613-1622. (Abstract).

Hermann et al. "Selective COX-2 Inhibitors and Renal Injury in Salt-sensitive Hypertension" Hypertension (2005) 45: 193-197.

Hermann et al. "Differential Effects of Selective Cyclooxygenase-2 Inhibitors on Endothelial Function in Salt-Induced Hypertension" Circulation (2003) 108: 2308-2311.

Jiang et al. "g-Tocopherol, but not a-Tocopherol, Decreases Proinflammatory Eicosanoids and Inflammation Damage in Rats" FASEB J. (2003) 17,816-822.

Krinsky "In NATO ASI Series, Sub-Series A (Life Sciences): Free Radicals, Oxidative Stress and Antioxidants: Pathological and Physiological Significance" Özben, T., Ed.; Plenum: NewYork, (1998) vol. 296, pp. 323-332.

Lee et al., "Astaxanthin inhibits Nitric Oxide production and inflammatory gene expression by suppressing IkB kinase-dependent NF-kB activation", 2003, Mol. Cells, vol. 16, pp. 97-105.

(Continued)

*Primary Examiner* — Kendra D Carter
(74) *Attorney, Agent, or Firm* — Meyertons, Hood, Kivlin, Kowert & Goetzel, P.C.; Eric B. Meyertons

(57) ABSTRACT

Administering water-soluble or dispersible synthetic analogs or derivatives of astaxanthin, lutein, zeaxanthin, or lycophyll and/or other carotenoids to a subject may reduce some of the adverse effects of inflammation in a body organ or tissue. The analogs or derivatives may be incorporated into pharmaceutical, over-the-counter, or nutraceutical preparations. Administration of the analogs or derivatives described herein may reduce deposition of inflammatory mediators such as C-reactive protein, complement system proteins or the membrane attack complex (MAC) in tissues. Reduced deposition of these molecules in tissues may reduce cell damage and/or lysis in the tissues.

15 Claims, 10 Drawing Sheets

(56) References Cited

OTHER PUBLICATIONS

Lee et al. "Biphasic regulation of leukocyte superoxide generation by nitric oxide and peroxynitrite." Journal of Biological Chemistry (2000). 275: 38965-38972.

Marnett et al. "COX-2: A Target for Colon Cancer Prevention" Annu. Rev. Pharmacol. Toxicol. (2002) 42: 55-80.

Martin et al. "Anti- and prooxidant properties of carotenoids" J. Prakt. Chem. (1999), 341( 3) 302-308.

Mathews-Roth "Recent Progress in the Medical Applications of Carotenoids" Pure Appl Chem (1991) 63:147-156.

Ohgami et al. "Effects of Astaxanthin on Lipopolysaccharide-induced Inflammation in vitro and in vivo" Investigative Ophthalmology & Visual Science (2003) 44(6):2694-2701.

Pratico et al. "F2-Isoprostanes as Indices of Lipid Peroxidation in Inflammatory Diseases" Chemistry and Physics of Lipids (2004) 128 (1-2), 165-171.

Ridker "C-Reactive Protein, Inflammation and Cardiovascular Disease—Clinical Update" Current Issues in Cardiology, vol. 32(3), 2005,384-386.

Shishehbor, et al., "Statins promote potent systemic antioxidant effects through specific inflammatory pathways", (2003), Circulation, vol. 108, pp. 426-431.

Upritchard et al. "Effect of supplementation with tomato juice, vitamin E, and vitamin C on LDL oxidation and products of inflammatory activity in type 2 diabetes." Diabetes Care (2000). 23(6): 733-738.

Victor et al. "Immune Cells: Free Radicals and Antioxidants in Sepsis" Int. Immunopharmacol. (2004) 4:327-347.

Walter et al. "Sulfone COX-2 Inhibitors Increase Susceptibility of Human LDL and Plasma to Oxidative Modification: Comparison to Sulfonamide COX-2 Inhibitors and NSAIDs" Atherosclerosis (2004), vol. 77, pp. 235-243.

Warner et al. "Nonsteroid Drug Selectivities for Cyclo-oxygenase-1 Rather Than Cyclo-oxygenase-2 are Associated with Human Gastrointestinal Toxicity: A Full in vitro Analysis" Proc. Natl. Acad. Sci. U S A. (1999) 96:7563-7568.

Yeh et al. "C-reactive Protein: Linking Inflammation to Cardiovascular Complications" Circulation (2001) 104:974-975.

Zhang et al., "Myeloperoxidase functions as a major enzymatic catalyst for initiation of lipid peroxidation at sites of inflammation", (2002), J. Biol. Chem., vol. 277, pp. 46116-46122.

Zimpfer, U., et al., "Synthesis, biological effects and pathophysiological implications of the novel arachidonic acid metabolite 5-oxo-eicosatetraenoic acid (review)," International Journal of Molelecular Medicine, 2, (1998), pp. 149-153.

* cited by examiner

A.

B.

C.

REDUCTION IN COMPLEMENT ACTIVATION AND INFLAMMATION DURING TISSUE INJURY BY CAROTENOIDS, CAROTENOID ANALOGS, OR DERIVATIVES THEREOF

CROSS REFERENCE TO RELATED APPLICATION

This application is a continuation application of U.S. patent application Ser. No. 11/392,470, filed Mar. 29, 2006 which claims the benefit of priority under 35 U.S.C. §119(e) to Provisional Patent Application Ser. No. 60/666,119, filed Mar. 29, 2005, entitled "REDUCTION IN COMPLEMENT ACTIVATION AND INFLAMMATION DURING TISSUE INJURY BY CAROTENOIDS, CAROTENOID ANALOGS, OR DERIVATIVES THEREOF." The prior application is commonly assigned with the present invention, and the contents thereof are incorporated by reference in their entirety as though fully set forth herein.

BACKGROUND OF THE INVENTION

1. Field of the Invention

The present invention generally relates to the fields of medicinal and synthetic chemistry. Specifically, the invention relates to the synthesis and use of water-soluble and water-dispersible carotenoids, including analogs, derivatives, and intermediates thereof, as therapeutic and/or prophylactic anti-inflammatory and anti-oxidant agents that reduce tissue damage associated with inflammation.

2. Description of the Related Art

Inflammation plays an important role in the pathophysiology of ischemic heart disease (Yeh et al., 2001). Elevated levels (>2 mg/dl) of C-reactive protein concentration (CRP), commonly used as a marker for an acute inflammatory response, are correlated with increased mortality due to cardiovascular events (Lagrand et al., 1999).

This relationship holds true for asymptomatic individuals (Ridker et al., 2000) and patients with unstable angina (Lindahl et al., 2000) and acute myocardial infarction (Pietila et al., 1996). It has been suggested that the epidemiological studies relating CRP to the incidence and outcome of ischemic syndromes are not simply due to CRP being a non-specific marker of disease susceptibility or inflammation but rather that CRP might be involved directly in the pathogenesis of ischemic syndromes through a proinflammatory effect mediated by complement activation (Beranek, 1997). The primary evidence for this hypothesis is derived from studies of autopsy specimens showing co-localization of CRP with activated complement components in infarcted myocardial tissue but not in healthy myocardium (Lagrand et al., 1997; Yasojima et al., 1998b). Deposition of CRP also occurs in the ischemic rabbit myocardium (Kushner et al., 1963) and is closely correlated with the infiltration of polymorphonuclear leukocytes (pro-inflammatory cells) to the ischemic tissue (du Clos et al., 1981). Additionally, studies have shown that the endogenous increase in plasma CRP secondary to a remote inflammatory lesion is associated with an increase in myocardial tissue injury secondary to regional ischemia and reperfusion. The myocardial injury occurs via a complement-dependent mechanism, and can be ameliorated by pretreatment with heparin, N-acetylheparin or can be prevented in rabbits deficient in complement protein C6, which are incapable of forming the membrane attack complex (Barrett et al., 2002). The evolving paradigm suggests that in the normal, healthy adult any elevations of CRP in the absence of acute infection or acute tissue injury can potentially be deleterious; indeed, in umbilical cord blood levels are very low (<0.01 mg/dl). For example, cardiovascular patients at risk for inflammatory heart disease benefit from lowering of circulating CRP levels, without evidence of a "no effect level" for this marker (Ridker et al. 2005). Local production of CRP by cells of other than hepatic origin has now been convincingly demonstrated (Venugopal et al. 2005), suggesting a tissue-specific role for this acute phase protein. Previous studies have also shown that administering carotenoid analogs or derivatives can reduce the serum concentration of CRP following ischemic reperfusion injury (Publication No. US-2005-0009758 and PCT International Application Number PCT/US2003/023706). Therapies aimed at (1) reducing circulating levels of CRP in mammals; (2) in the localized and/or systemic production of CRP by liver and other tissues; and (3) the deposition of CRP (either with or without other endogenous inflammatory mediators) in pathological injury will have important therapeutic value (Ridker 2005).

Carotenoids are a group of natural pigments produced principally by plants, yeast, and microalgae. The family of related compounds now numbers greater than 700 described members, exclusive of Z and E isomers. Humans and other animals cannot synthesize carotenoids de novo and must obtain them from their diet. All carotenoids share common chemical features, such as a polyisoprenoid structure, a long polyene chain forming the chromophore, and near symmetry around the central double bond. Tail-to-tail linkage of two $C_{20}$ geranyl-geranyl diphosphate molecules produces the parent $C_{40}$ carbon skeleton. Carotenoids without oxygenated functional groups are called "carotenes", reflecting their hydrocarbon nature; oxygenated carotenes are known as "xanthophylls." Cyclization at one or both ends of the molecule yields 7 identified end groups (illustrative structures shown in FIG. 1). Examples of uses of carotenoid derivatives and analogs are illustrated in U.S. patent application Ser. No. 10/793,671 filed on Mar. 4, 2004, entitled "CAROTENOID ETHER ANALOGS OR DERIVATIVES FOR THE INHIBITION AND AMELIORATION OF DISEASE" by Lockwood et al. published on Jan. 13, 2005, as Publication No. US-2005-0009758 and PCT International Application Number PCT/US2003/023706 filed on Jul. 29, 2003, entitled "STRUCTURAL CAROTENOID ANALOGS FOR THE INHIBITION AND AMELIORATION OF DISEASE" by Lockwood et al. (International Publication Number WO 2004/011423 A2, published on Feb. 5, 2004) both of which are incorporated by reference as though fully set forth herein.

Documented carotenoid functions in nature include light harvesting, photoprotection, and protective and sex-related coloration in microscopic organisms, mammals, and birds, respectively. A relatively recent observation has been the protective role of carotenoids against age-related diseases in humans as part of a complex antioxidant network within cells. This role is dictated by the close relationship between the physicochemical properties of individual carotenoids and their in vivo functions in organisms. The long system of alternating double and single bonds in the central part of the molecule (delocalizing the π-orbital electrons over the entire length of the polyene chain) confers the distinctive molecular shape, chemical reactivity, and light-absorbing properties of carotenoids. Additionally, isomerism around C=C double bonds yields distinctly different molecular structures that may be isolated as separate compounds (known as Z ("cis") and E ("trans"), or geometric, isomers). Of the more than 700 described carotenoids, an even greater number of the theoretically possible mono-Z and poly-Z isomers are sometimes encountered in nature. The presence of a Z double bond creates greater steric hindrance between nearby hydrogen atoms and/or methyl groups, so that Z isomers are generally less stable thermodynamically, and more chemically reactive, than the corresponding all-E form. The all-E configuration is an extended, linear, and rigid molecule. Z-isomers are, by contrast, not simple, linear molecules (the so-called "bent-chain" isomers). The presence of any Z in the polyene chain creates a bent-chain molecule. The tendency of Z-isomers to crystallize or aggregate is much less than all-E, and Z isomers may sometimes be more readily solubilized, absorbed, and transported in vivo than their all-E counterparts. This has important implications for enterable (e.g., oral) and parenteral (e.g., intravenous, intra-arterial, intramuscular, intraperitoneal, intracoronary, and subcutaneous) dosing in mammals.

Problems related to the use of some prior art carotenoids and structural carotenoid analogs or derivatives include: (1) the complex isomeric mixtures, including non-carotenoid contaminants, provided in natural and synthetic sources leading to costly increases in safety and efficacy tests required by such agencies as the FDA; (2) limited bioavailability upon administration to a subject; and (3) the differential induction of cytochrome P450 enzymes (this family of enzymes exhibits species-specific differences which must be taken into account when extrapolating animal work to human studies). Selection of the appropriate analog or derivative and isomer composition for a particular application increases the utility of carotenoid analogs or derivatives for the uses defined herein.

New methods of reducing or inhibiting one or more of the pathological complications associated with inflammation and/or tissue injury associated with inflammation, including deposition of pro-inflammatory molecules and protein complexes in a body tissue of a subject would be useful therapeutic agents. Carotenoid analogs or derivatives displaying properties of increased water-dispersibility and bioavailability would be beneficial for such applications.

SUMMARY OF THE INVENTION

Methods and pharmaceutical compositions for reducing or inhibiting one or more of the pathological complications associated with inflammation and/or tissue injury associated with inflammation, including deposition of pro-inflammatory molecules and protein complexes in a body tissue of a subject are provided for herein. The methods and pharmaceutical compositions described herein may be used to treat of prevent a myriad of pathologies associated with inflammatory responses, including but not limited to those affecting the respiratory, cardiovascular or nervous systems, vision and hearing, dental tissues, smooth musculature, and transplantation of cells and tissues. Such methods can be used alone as the sole therapeutic regimen or in combination with one or more other established protocols for addressing a particular disease or condition. Carotenoid analogs or derivatives useful in the treatment methods contemplated herein are characterized in functioning as anti-inflammatory agents.

More specifically the presently disclosed treatment methods and pharmaceutical compositions relate to preventing, reducing or inhibiting one or more of the pathological complications associated with inflammation and/or tissue injury associated with inflammation caused, at least in part, by the deposition and accumulation of pro-inflammatory molecules and protein complexes in a body tissue of a subject. The treatment methods contemplated herein preferably include administering a therapeutically effective amount of at least one carotenoid analog or derivative which prevents, reduces or inhibits activation of complement proteins, initiation of complement-mediated cellular lysis, accumulation of the membrane attack complex, or accumulation of C-reactive protein in a tissue, such as for example a cardiovascular tissue, during an inflammatory response.

In some embodiments, methods of reducing, preventing or inhibiting pathological complications associated with inflammation and/or tissue injury associated with inflammation, including deposition of pro-inflammatory molecules and protein complexes in a body tissue of a subject may include administering to the cell, group of cells or subject an effective amount of a pharmaceutically acceptable formulation including a synthetic analog or derivative of a carotenoid.

In some embodiments, methods of reducing, preventing or inhibiting pathological complications associated with inflammation and/or tissue injury associated with inflammation, including deposition of pro-inflammatory molecules and protein complexes in a body tissue of a subject may include administering to the cell, group of cells or to a subject, an effective amount of a pharmaceutically acceptable formulation including a synthetic analog or derivative of a carotenoid.

In some embodiments, methods of reducing, preventing or inhibiting pathological complications associated with inflammation and/or ischemia/reperfusion injury in a body tissue of a subject may include administering to the subject an effective amount of a pharmaceutically acceptable formulation including a synthetic analog or derivative of a carotenoid. In an embodiment, the formulation may include diacid or diphosphate derivatives of a carotenoid.

In some embodiments, methods of reducing, preventing or inhibiting pathological complications associated with an inflammatory response in a tissue of a subject may include administering to the subject an effective amount of a pharmaceutically acceptable formulation including a synthetic analog or derivative of a carotenoid. In an embodiment, the formulation may include diacid or diphosphate derivatives of a carotenoid.

In some embodiments, methods of reducing, preventing or inhibiting pathological complications associated with an inflammatory response in a tissue of a subject may include administering to the subject an effective amount of a pharmaceutically acceptable formulation including a synthetic analog or derivative of a carotenoid so as to reduce, prevent or inhibit the activation of complement proteins (i.e., the "complement cascade") in the subject. In an embodiment, the formulation may include diacid or diphosphate derivatives of a carotenoid.

In some embodiments, methods of reducing, preventing or inhibiting pathological complications associated with an inflammatory response in a tissue of a subject may include administering to the subject an effective amount of a pharmaceutically acceptable formulation including a synthetic analog or derivative of a carotenoid so as to reduce, prevent or inhibit the membrane attack complex (MAC) deposition in a tissue of a subject. In an embodiment, the formulation may include diacid or diphosphate derivatives of a carotenoid.

In some embodiments, methods of reducing, preventing or inhibiting pathological complications associated with an inflammatory response in a tissue of a subject may include administering to the subject an effective amount of a pharmaceutically acceptable formulation including a synthetic analog or derivative of a carotenoid so as to reduce, prevent or inhibit the accumulation/deposition of C-reactive protein (CRP) in a tissue of a subject. In an embodiment, the formulation may include diacid or diphosphate derivatives of a carotenoid.

In some embodiments, methods of methods of reducing, preventing or inhibiting tissue injury associated with ischemia/reperfusion of a tissue, especially a cardiovascular tissue, of a subject may include administering to the subject an effective amount of a pharmaceutically acceptable formulation including a synthetic analog or derivative of a carotenoid so as to reduce, prevent or inhibit the accumulation of the membrane attack complex and/or C-reactive protein in the at the site of ischemia/reperfusion. In an embodiment, the formulation may include diacid or diphosphate derivatives of a carotenoid.

In some embodiments, methods of treating macular degeneration (any age of onset) as well as Age-Related Macular Degeneration (ARMD) in a subject may include administering to the subject an effective amount of a pharmaceutically acceptable formulation including a synthetic analog or derivative of a carotenoid. The treatment may reduce tissue damage associated with inflammation in the macula, and increase visual acuity or halt progression of its deterioration. In an embodiment, the formulation may include diacid or diphosphate derivatives of a carotenoid.

The presently described treatment methods, including the administration of pharmaceutically acceptable formulations containing synthetic carotenoid analogs or derivatives, may be provided alone as a primary therapy, or may be provided in conjunction with one more additional therapeutic agents (e.g. anti-inflammatory medications). Such determination may be made by an appropriate healthcare provider or practitioner of ordinary skill in the art.

Administration of analogs or derivatives of carotenoids according to the preceding embodiments may at least partially prevent, reduce or inhibit one or more of the pathological complications associated with inflammation and/or tissue injury. Complications associated with inflammation and ischemia/reperfusion injury that may be influenced according to some embodiments include activation of complement proteins, deposition of activated complement proteins and the membrane attack complex in tissues, cellular and tissue damage caused by generation of reactive oxygen species and other radicals, and deposition of C-reactive protein at sites of inflammation. Reduction in the incidence and/or severity of one or more of the aforementioned complications may reduce the amount of tissue damage occurring at a site of inflammation.

In some embodiments, the administration of structural analogs or derivatives of carotenoids by one skilled in the art—including consideration of the pharmacokinetics and pharmacodynamics of therapeutic drug delivery—is expected to inhibit and/or ameliorate disease conditions associated with abnormal cell division. In some of the foregoing embodiments, analogs or derivatives of carotenoids administered to cells may be at least partially water-soluble.

"Water-soluble" structural carotenoid analogs or derivatives are those analogs or derivatives that may be formulated in aqueous solution, either alone or with one or more excipients. Water-soluble carotenoid analogs or derivatives may include those compounds and synthetic derivatives which form molecular self-assemblies, and may be more properly termed "water dispersible" carotenoid analogs or derivatives. Water-soluble and/or "water-dispersible" carotenoid analogs or derivatives may be preferred in some embodiments.

Water-soluble carotenoid analogs or derivatives may have a water solubility of greater than about 1 mg/mL in some embodiments. In certain embodiments, water-soluble carotenoid analogs or derivatives may have a water solubility of greater than about 10 mg/mL. In certain embodiments, water-soluble carotenoid analogs or derivatives may have a water solubility of greater than about 20 mg/mL. In certain embodiments, water-soluble carotenoid analogs or derivatives may have a water solubility of greater than about 25 mg/mL. In some embodiments, water-soluble carotenoid analogs or derivatives may have a water solubility of greater than about 50 mg/mL.

In some embodiments, water-soluble analogs or derivatives of carotenoids may be administered to a cell, a group of cells or to a subject alone or in combination with additional carotenoid analogs or derivatives.

In some embodiments, a method to at least partially prevent, reduce or inhibit one or more of the pathological complications associated with inflammation and/or tissue injury may include administering to the subject an effective amount of a pharmaceutically acceptable formulation including a synthetic analog or derivative of a carotenoid. The synthetic analog or derivative of the carotenoid may have the structure

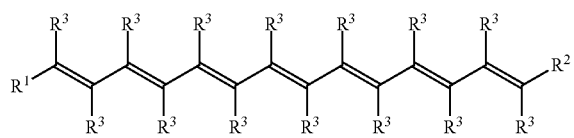

where each $R^3$ is independently hydrogen or methyl, and where each $R^1$ and $R^2$ are independently:

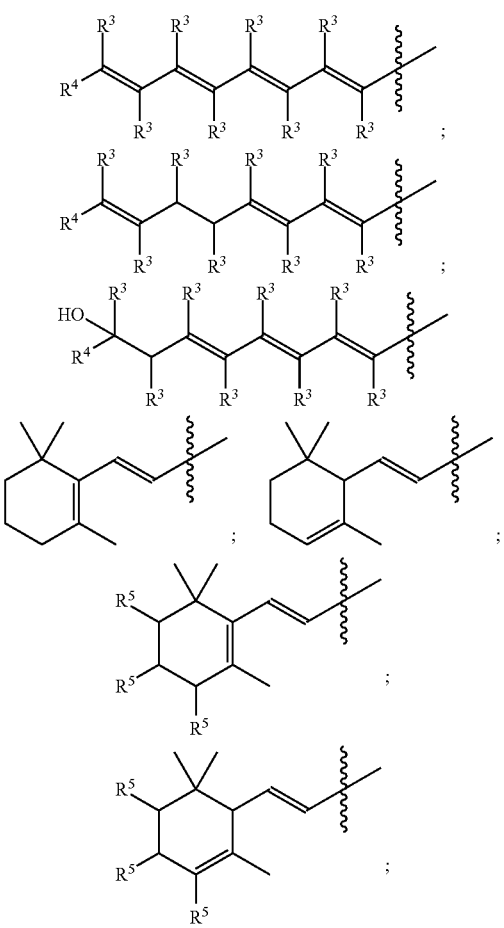

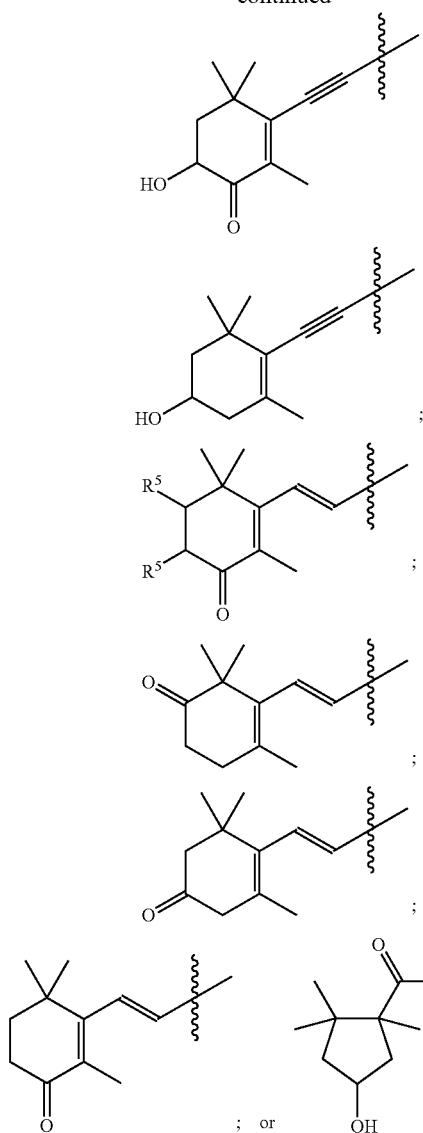

where $R^4$ is hydrogen, methyl, or —$CH_2OH$; and where each $R^5$ is independently hydrogen or —OH.

In some embodiments, a method to at least partially prevent, reduce or inhibit one or more of the pathological complications associated with inflammation and/or tissue injury may include administering to the subject an effective amount of a pharmaceutically acceptable formulation including a synthetic analog or derivative of a carotenoid. The synthetic analog or derivative of the carotenoid may have the structure

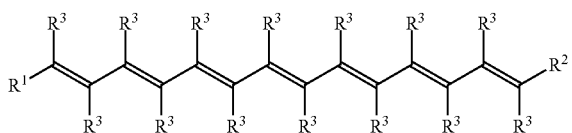

where each $R^3$ is independently hydrogen or methyl, and where each $R^1$ and $R^2$ are independently:

where $R^4$ is hydrogen or methyl; where each $R^5$ is independently hydrogen, —OH, or —$OR^6$ wherein at least one $R^5$ group is —$OR^6$; wherein each $R^6$ is independently: alkyl; aryl; -alkyl-$N(R^7)_2$; -aryl-$N(R^7)_2$; -alkyl-$CO_2H$; -aryl-$CO_2H$; —O—C(O)—$R^8$; —P(O)$(OR^8)_2$; —S(O)$(OR^8)_2$; an amino acid; a peptide, a carbohydrate; —C(O)—$(CH_2)_n$—$CO_2R^9$; —C(O)—$OR^9$; a nucleoside residue, or a co-antioxidant; where $R^7$ is hydrogen, alkyl, or aryl; wherein $R^8$ is hydrogen, alkyl, aryl, benzyl, or a co-antioxidant; and where $R^9$ is hydrogen; alkyl; aryl; —P(O)$(OR^8)_2$; —S(O)$(OR^8)_2$; an amino acid; a peptide, a carbohydrate; a nucleoside, or a co-antioxidant; and where n is 1 to 9. Pharmaceutically acceptable salts of any of the above listed carotenoid derivatives may also be used to ameliorate at least some of the pathological consequences associated with inflammatory responses in a tissue.

Each co-antioxidant may be independently Vitamin C, Vitamin C analogs, Vitamin C derivatives, Vitamin E, Vitamin E analogs, Vitamin E derivatives, flavonoids, flavonoid derivatives, or flavonoid analogs. Flavonoids include, but are not limited to, quercetin, xanthohumol, isoxanthohumol, or genistein. Selection of the co-antioxidant should not be seen as limiting for the therapeutic application of the current invention.

The carotenoid analogs or derivatives for use in the contemplated treatment methods and pharmaceutical compositions may have one or more of the non-limiting structures Na, K, Li or the like), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. In an embodiment, R' is $CH_2$, n is 1, and R is sodium.

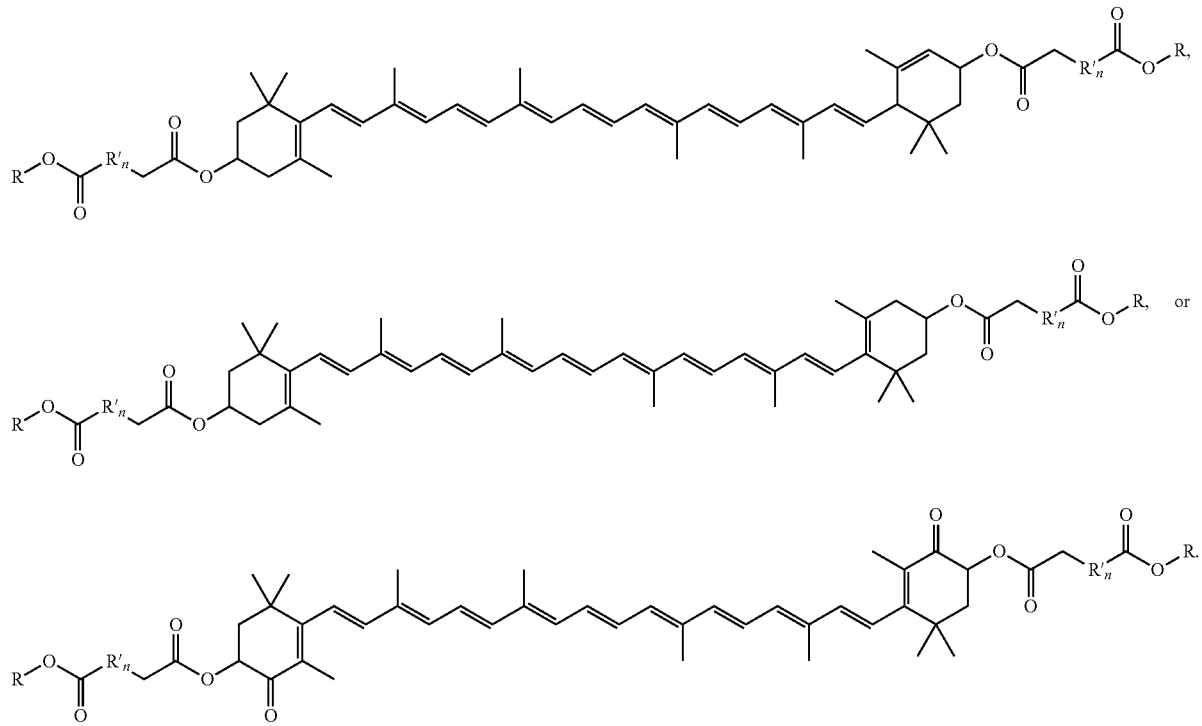

Each R' may be $CH_2$. n may range from 1 to 9. Each R may be independently H, alkyl, aryl, benzyl, a Group IA metal (e.g., In some embodiments, the carotenoid analog or derivative may have the structure

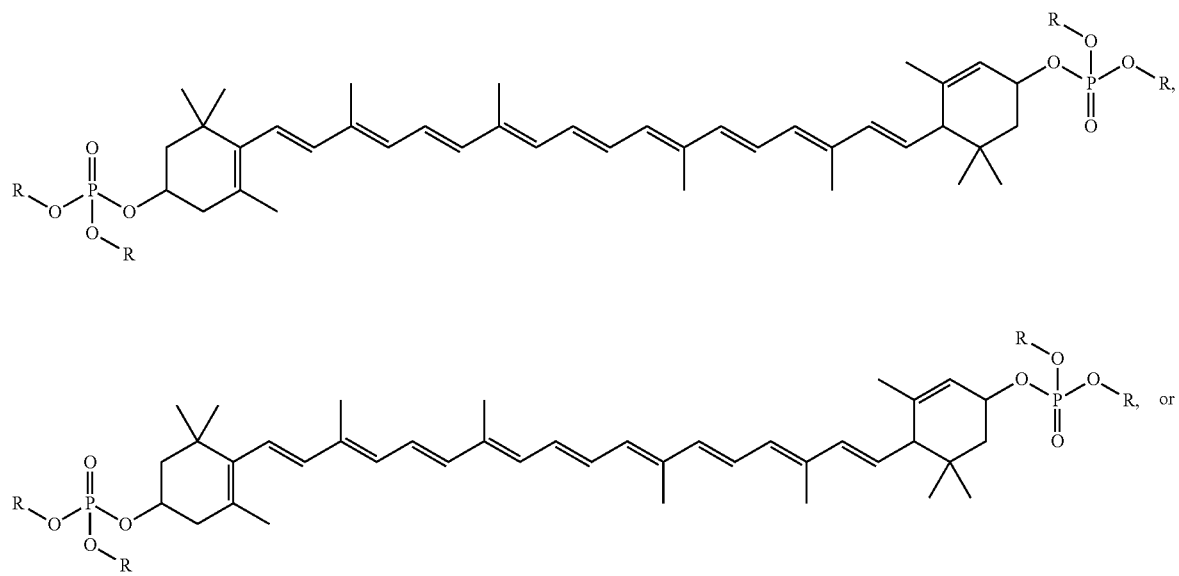

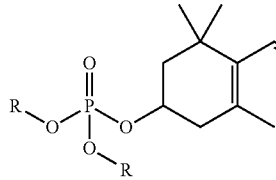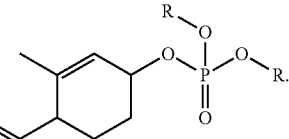

Each R may be independently H, alkyl, aryl, benzyl, a Group IA metal (e.g., Na, K, Li, or the like), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. In an embodiment, R is sodium. When R includes Vitamin C, Vitamin C analogs, or Vitamin C derivatives, some embodiments may include carotenoid analogs or derivatives having the structure to be administered orally, or by one or more parenteral routes of administration. In an embodiment, the pharmaceutical composition may be adapted such that at least a portion of the dosage of carotenoid or synthetic derivative or analog thereof is delivered prior to, during, or after at least a portion of the additional anti-inflammatory drug(s) are delivered.

In some embodiments, separate pharmaceutical compositions are provided, such that the one or more additional anti-inflammatory drugs are delivered separately from carotenoid, or synthetic derivatives or analogs thereof (sometimes referred to in the art as a "co-administration" strategy). The

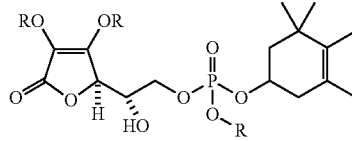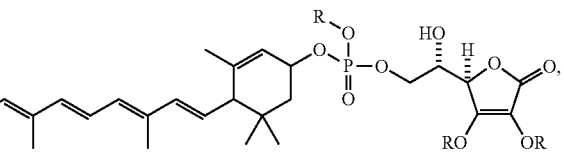

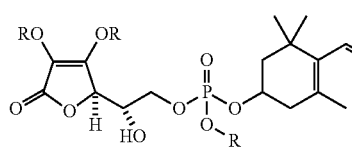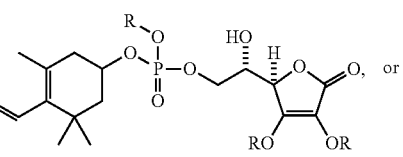

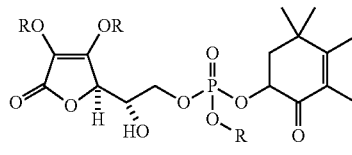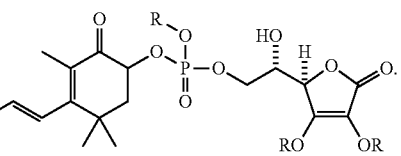

Each R may be independently H, alkyl, aryl, benzyl, or a Group IA metal.

In some embodiments, a pharmaceutical composition is provided that may include one or more synthetic carotenoids ("a co-formulation" strategy), or synthetic derivatives or analogs thereof, in combination with one or more anti-inflammatory drugs. Certain embodiments may further directed to pharmaceutical compositions that include combinations of two or more carotenoids or synthetic analogs or derivatives thereof. In an embodiment, a pharmaceutical composition may include a chiral astaxanthin or a synthetic derivative thereof in combination with one or more additional anti-inflammatory drugs. In an embodiment, a pharmaceutical composition may include a synthetic derivative of lycophyll in combination with one or more additional anti-inflammatory drugs. The pharmaceutical compositions may be adapted pharmaceutical compositions may be adapted to be administered orally, or by one or more parenteral routes of administration. In an embodiment, the pharmaceutical composition may be adapted such that at least a portion of the dosage of the carotenoid or synthetic derivative or analog thereof is delivered prior to, during, or after at least a portion of the one or more additional anti-inflammatory drugs are administered to the subject. The carotenoid, carotenoid analogs and/or derivatives may also be administered alone.

Embodiments directed to pharmaceutical compositions may further include appropriate vehicles for delivery of said pharmaceutical composition to a desired site of action (i.e., the site a subject's body where the biological effect of the pharmaceutical composition is most desired). Pharmaceutical compositions including xanthophyll carotenoids or analogs or derivatives of astaxanthin, lutein, zeaxanthin, or lycophyll that may be administered orally or intravenously may be particularly advantageous for and suited to embodiments described herein. In yet a further embodiment, an injectable astaxanthin formulation or a structural analog or derivative may be administered with a astaxanthin, zeaxanthin or lutein structural analog or derivative and/or other carotenoid structural analogs or derivatives, or in formulation with antioxidants and/or excipients that further the intended purpose. In some embodiments, one or more of the xanthophyll carotenoids or synthetic analogs or derivatives thereof may be at least partially water-soluble.

Certain embodiments may further directed to pharmaceutical compositions including combinations two or more structural carotenoid analogs or derivatives. Pharmaceutical compositions including injectable structural carotenoid analogs or derivatives of lutein may be particularly advantageous for the methods described herein. In yet a further embodiment, an injectable lutein structural analog or derivative may be administered with a zeaxanthin structural analog or derivative and/or other carotenoid structural analogs or derivatives, or in formulation with antioxidants and/or excipients that further the intended purpose. In some embodiments, one or more of the lutein structural analogs or derivatives are water-soluble.

In some embodiments, the administration of structural analogs or derivatives of carotenoids by one skilled in the art— including consideration of the pharmacokinetics and pharmacodynamics of therapeutic drug delivery—is expected to inhibit and/or ameliorate disease conditions associated with elevated inflammation and elevated CRP. In some of the foregoing embodiments, analogs or derivatives of carotenoids administered to a subject may be at least partially water-soluble.

"Water-soluble" structural carotenoid analogs or derivatives are those analogs or derivatives that may be formulated in aqueous solution, either alone or with one or more excipients. Water-soluble carotenoid analogs or derivatives may include those compounds and synthetic derivatives that form molecular self-assemblies, and may be more properly termed "water dispersible" carotenoid analogs or derivatives. Water-soluble and/or "water-dispersible" carotenoid analogs or derivatives may be preferred in some embodiments.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/ml-10 mg/mL. In certain embodiments, water-soluble carotenoid analogs or derivatives may have a water solubility of greater than about 20 mg/mL. In certain embodiments, water-soluble carotenoid analogs or derivatives may have a water solubility of greater than about 25 mg/mL. In some embodiments, water-soluble carotenoid analogs or derivatives may have a water solubility of greater than about 50 mg/mL.

Certain embodiments may further directed to pharmaceutical compositions including combinations two or more structural carotenoid analogs or derivatives. Embodiments directed to pharmaceutical compositions may further include appropriate vehicles for delivery of said pharmaceutical composition to a desired site of action (i.e., the site a subject's body where the biological effect of the pharmaceutical composition is most desired). Pharmaceutical compositions including injectable structural carotenoid analogs or derivatives of astaxanthin, lutein or zeaxanthin may be particularly advantageous for the methods described herein. In yet a further embodiment, an injectable astaxanthin structural analog or derivative may be administered with a astaxanthin, zeaxanthin or lutein structural analog or derivative and/or other carotenoid structural analogs or derivatives, or in formulation with antioxidants and/or excipients that further the intended purpose. In some embodiments, one or more of the astaxanthin, lutein or zeaxanthin structural analogs or derivatives are water-soluble.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

Figure 1:
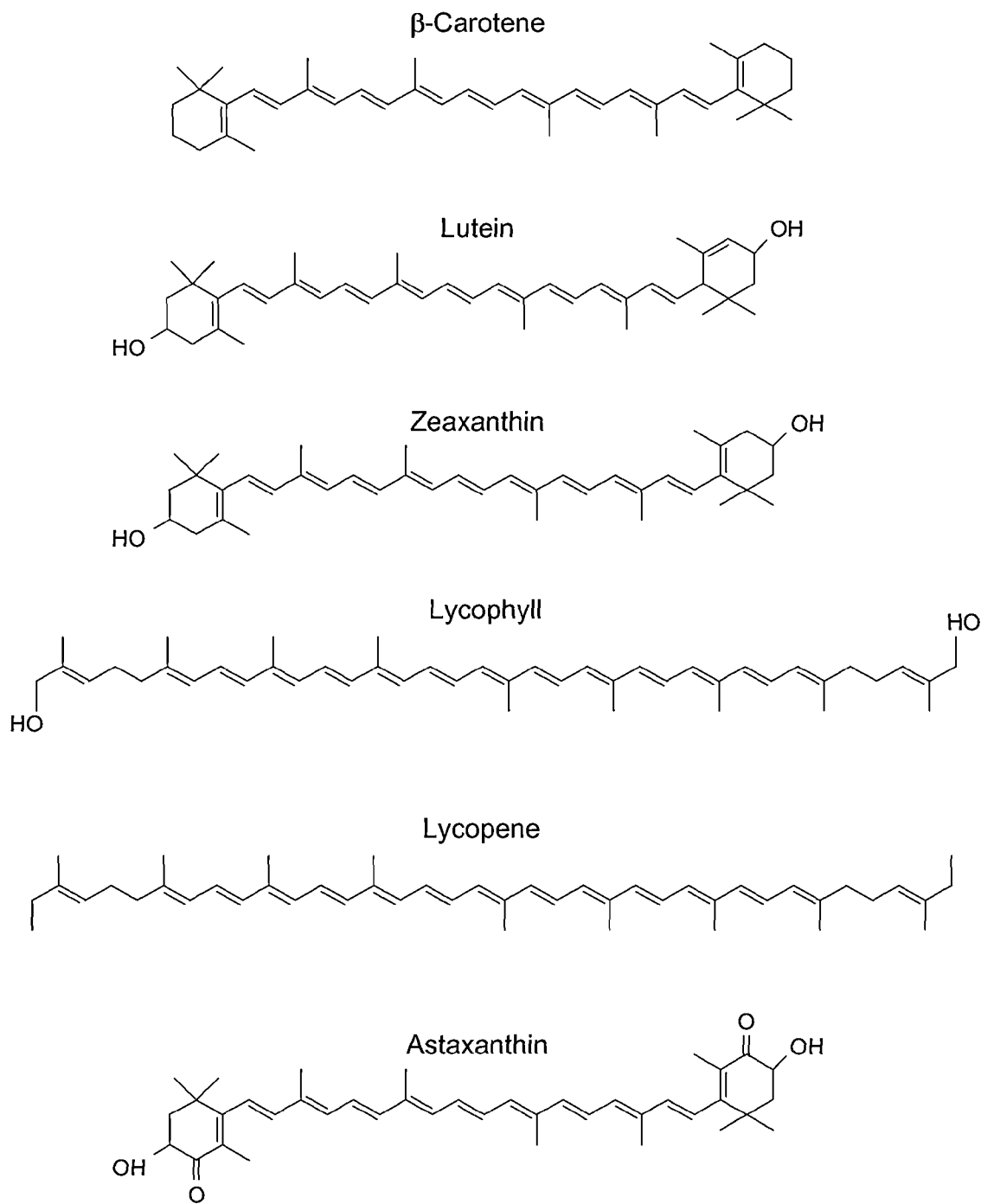
FIG. 1 depicts a graphic representation of several examples of "parent" carotenoid structures as found in nature.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

The terms used throughout this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "xanthophyll carotenoid" generally refers to a naturally occurring or synthetic 40-carbon polyene chain with a carotenoid structure that contains at least one oxygen-containing functional group. The chain may include terminal cyclic end groups. Exemplary, though non-limiting, xanthophyll carotenoids include astaxanthin, zeaxanthin, lutein, echinenone, lycophyll, canthaxanthin, and the like. Non-limiting examples of carotenoids that are not xanthophyll carotenoids include -carotene and lycopene.

Figure 10:
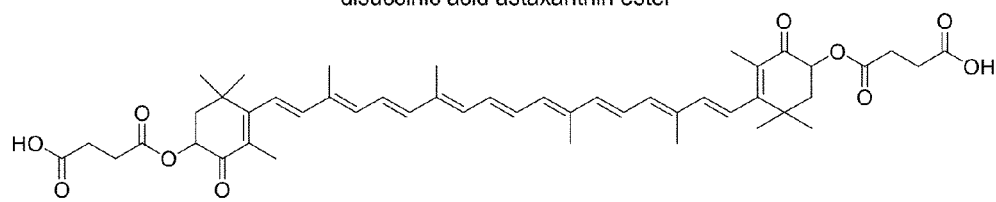
FIG. 10 depicts the chemical structures of three synthetic water-soluble carotenoid analogs or derivatives according to certain non-limiting embodiments. (A) disuccinic acid astaxanthin ester; (B) disodium disuccinic acid ester astaxanthin salt (Cardax™); and (C) divitamin C disuccinate astaxanthin ester.
Figure 10:
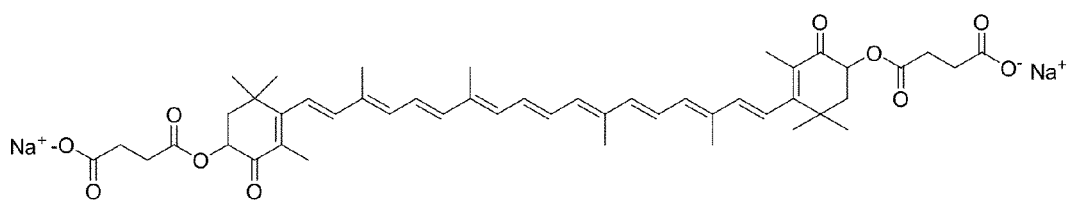
Figure 10:
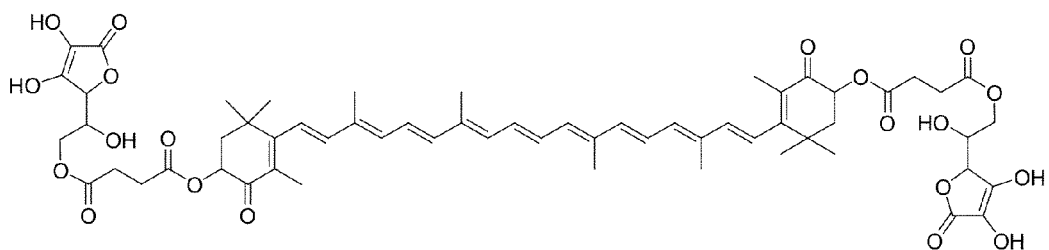

As used herein, terms such as "carotenoid analog" and "carotenoid derivative" generally refer to chemical compounds or compositions derived from a naturally occurring or synthetic carotenoid. Terms such as carotenoid analog and carotenoid derivative may also generally refer to chemical compounds or compositions that are synthetically derived from non-carotenoid based parent compounds; however, which ultimately substantially resemble a carotenoid derived analog. Non-limiting examples of carotenoid analogs and derivatives that may be used according to some of the embodiments described herein are depicted schematically in FIG. 10.

As used herein, the term "cell or a group of cells" is meant to include a single cell or group of cells that are isolated in culture as well as those cells or groups of cells naturally residing in a body or as part of a body organ or body tissue. The term "organ", when used in reference to a part of the body of an animal or of a human generally refers to the collection of cells, tissues, connective tissues, fluids and structures that are part of a structure in an animal or a human that is capable of performing some specialized function. Groups of organs constitute one or more specialized body systems. The specialized function performed by an organ is typically essential to the life or the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, musculoskeletal, nervous, digestive, endocrine, exocrine, hepato-biliary, reproductive, and urinary systems. In animals the organs are generally made up of several tissues, one of which usually predominates, and determines the principal function of the organ. The term "tissue", when used in reference to a part of a body or of an organ, generally refers to an aggregation or collection of morphologically similar cells and associated accessory cells and intercellular matter, including extracellular matrix material and fluids, acting together to perform specific functions in the body. There are generally four basic types of tissue in animals and humans including muscle, nerve, epithelial, and connective tissues.

As used herein, the term "organ", when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, terms such as "deposition in a tissue," "tissue deposition," "tissue accumulation," or the like generally refer to the accumulation of a particular factor or a group of factors in tissue. The factor(s) deposited in the tissue may be soluble or carried to the tissue as a suspended factor in plasma. A factor may also be deposited by other cells. Once immobilized in the tissue, a deposited factor may carry out any number of physiological or pathological functions. Examples of factors that may be deposited in tissues include acute phase proteins, sediments, immune complexes, pathogens, hormones and the like.

As used herein the term "ischemia-reperfusion injury" is generally defined as the pathology attributed to reoxygenation of previously ischemic tissue (either chronically or acutely ischemic), which includes atherosclerotic and thromboembolic vascular disease and its related illnesses. In particular, major diseases or processes including myocardial infarction, stroke, peripheral vascular disease, venous or arterial occlusion and/or restenosis, organ transplantation, coronary artery bypass graft surgery, percutaneous transluminal coronary angioplasty, and cardiovascular arrest and/or death are included, but are not seen as limiting for other pathological processes which involve reperfusion of ischemic tissue in their individual pathologies.

As used herein, terms such as "inflammation," "inflammatory response," or the like, generally refer to an important biological process that is a component of the immune system. Inflammation is the first response of the immune system to infection or irritation in a body tissue and may be referred to as the innate cascade. Inflammation may generally be characterized as causing a tissue to have one or more of the following characteristics: redness ("rubor"), heat ("calor"), swelling, pain ("dolor") and dysfunction of the organs involved. Though inflammation is an important component of innate immunity, if left unabated, it may result severe and sometimes irreparable tissue damage. Low levels of inflammation that persist through time without resolution ("chronic" or "smoldering" inflammation) are now recognized as an important pathological component of many diseases, in particular cardiovascular disease. Inflammation also contributes to the pathophysiology of numerous disorders such as, for example, tissue reperfusion injury following myocardial infacrtion, system lupus erythematosis, Crohn's disease, and the like.

As used herein, the term "inflammatory disorder" generally refers to Inflammatory disorders that may be treated using the methods contemplated herein may include those disorders that are characterized by aberrant or otherwise dysregulated, prolonged or inappropriate inflammatory responses, such as, for example, colorectal cancer; cardiovascular disease; ischemic reperfusion injury; Rheumatoid arthritis; Osteoarthritis; Inflammatory arthropathies (e.g., ankylosing spondylitis, psoriatic arthritis, Reiter's syndrome); Acute gout; Dysmenorrhoea; Metastatic bone pain; Headache and migraine; Postoperative pain; Mild-to-moderate pain due to inflammation and tissue injury; Pyrexia; Renal colic. A subset of inflammatory disorder may be due, at least in part, to abberant activation of the complement system. The complement system may contribute to the pathophysiology of certain diseases with an immunological/inflammatory component, such as Alzheimer's disease, asthma, systemic lupus erythematosus, diabetes mellitus, glomerulonephritis, Crohn's disease, atherosclerosis, various forms of arthritis (e.g. osteoarthritis and rheumatoid arthritis), autoimmune heart disease, multiple sclerosis and Age-Related Macular degeneration (ARMD). Deficiencies in terminal pathway components predispose patients to certain autoimmune diseases and infections (particularly meningitis).

As used herein, terms such as "complement," "complement system," "complement cascade," "complement pathway," or the like, when used in reference to a group of immunologically active polypeptides, generally refers to one or more of about 30 distinct art-recognized plasma proteins that function together as a component of the innate immune system of an organism. The terms may also be used by the skilled artisan to refer to the biochemical reactions that occur between various protein members of the complement system to initiate one or more components of an innate (e.g., formation of the membrane-attack complex or MAC) or cellular immune response (e.g., opsonization).

As used herein, the term "membrane-attack complex" or "MAC" generally refers to a multi-subunit macromolecular complex that is formed on the membrane of a target cell by the multimerization of terminal complement system components (in particular complement proteins C5b through C9). Assembly of the components into a MAC on the surface of a cell results in the formation of a membrane-spanning hydrophilic pore, and ultimately in the lysis and destruction of the cell on which the MAC formed. Although the evolutionary function of the formation of the terminal MAC appears to be protection against foreign invaders (i.e. infectious disease), in a form of molecular mimicry, normal cells exposed to this innate immune system can be destroyed (a form of auto-immune disease).

As used herein, the term "complement-mediated lysis" generally refers to the biological process described above, whereby one or more activated complement system proteins ultimately compromise the integrity of the plasma membrane of a cell.

As used herein, the term "C-reactive protein" or "CRP" generally refers to an acute phase protein synthesized predominantly in the liver, as well as in other cells locally such as endothelial cells, in response to inflammation.

As used herein, the term "complement factor H," or "CFH" generally refers to a roughly 155 kDa plasma glycoprotein that is a key regulator of the complement system.

The term "modulate," as used herein, generally refers to a change or an alteration in a biological parameter. Examples biological parameters subject to modulation according to certain embodiments described herein may include, by way of non-limiting example only: inflammation, complement activation, MAC tissue deposition, CRP tissue deposition, changes in protein or gene expression, complement-mediated cellular lysis, tissue damage associated with ischemia/reperfusion injury or the initiation or progression of an inflammatory reaction, or the like. "Modulation" may refer to a net increase or a net decrease in the biological parameter.

As used herein the terms "inhibiting," "reducing," "ameliorating," and the like, when used in the context of modulating a pathological or disease state, generally refers to the prevention and/or reduction of at least a portion of the negative consequences of the disease state. When used in the context of biochemical pathway or of protein function, the term "inhibiting" generally refers to a net reduction in the activity of the pathway or function.

As used herein, the term "systemically," when used in the context of a physiological parameter, generally refers to a parameter that affects the entire body of a subject, or to a particular body system.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, the term "treat" generally refers to an action taken by a caregiver that involves substantially inhibiting, slowing or reversing the progression of a disease, disorder or condition, substantially ameliorating clinical symptoms of a disease disorder or condition, or substantially preventing the appearance of clinical symptoms of a disease, disorder or condition.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release" or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, pharmaceutical compositions, formulations and preparations may include pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

As used herein the terms "subject" generally refers to a mammal, and in particular to a human.

Terms such as "in need of treatment," "in need thereof," "benefit from such treatment," and the like, when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

As used herein, the term "additional anti-inflammatory agent" generally refers to a pharmacologically active drug or composition that may be co-administered with the subject carotenoid analogs or derivatives, and whose primary biological function is to inhibit, reduce or ameliorate at least a subset of symptoms associated with inflammation. Anti-inflammatory drugs may generally be divided into two broad categories; steroidal anti-inflammatory drugs; and non-steroidal anti-inflammatory drugs. A "steroidal anti-inflammatory drug" may generally refer to a naturally-occurring glucocorticoid (e.g., cortisol; hydrocortisone) or one or more synthetic glucocorticoids. Non-limiting examples of glucocorticoids include Prednisone; Prednisolone; Methylprednisolone; Meprednisone; Triamcicolone; Paramethasone; Fluprednisolone; Betamethasone; Dexamethasone; and Fludrocortisone.

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are sometimes also referred to as non-steroidal anti-inflammatory agents/analgesics (NSAIAs). Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyses the formation of prostaglandins and thromboxane from arachidonic acid (itself derived from the cellular phospholipid bilayer by phospholipase $A_2$). Non-limiting examples of some NSAIDS used in certain clinical setting for the treatment or reduction of symptoms associated with inflammation include, though are not limited to, Aspirin; Diclofenac; Diflunisal; Etodolac; Fenoprofen; Floctafenine; Flurbiprofen; Ibuprofen; Indomethacin; Ketorolac; Ketoprofen; Meclofenamate; Mefenamic Acid; Meloxicam; Nabumetone; Naproxen; Nimesulide; Oxaprozin; Phenylbutazone; Piroxicam; Salsalate; Sulindac; Tenoxicam; Tiaprofenic Acid; Tolmetin; Celecoxib; rofecoxib; etoricoxib; and valdecoxib.

By "therapeutically effective amount" is meant an amount of a drug or pharmaceutical composition that will elicit at least one desired biological or physiological response of a cell, a tissue, a system, animal or human that is being sought by a researcher, veterinarian, physician or other caregiver.

By "prophylactically effective amount" is meant an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

Terms such as "pharmaceutically inert," "pharmacologically inert," or the like, as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

As used herein the term "antioxidant" may be generally defined as any of various substances (such as beta-carotene, vitamin C, and -tocopherol) that inhibit oxidation or reactions promoted by Reactive Oxygen Species (ROS) and other radical and non-radical species.

As used herein the term "co-antioxidant" may be generally defined as an antioxidant that is used and that acts in combination with another antioxidant (e.g., two antioxidants that are chemically and/or functionally coupled, or two antioxidants that are combined and function with each another in a pharmaceutical preparation). The effects of co-antioxidants may be additive (i.e., the anti-oxidative potential of one or more anti-oxidants acting additively is approximately the sum of the oxidative potential of each component anti-oxidant) or synergistic (i.e., the anti-oxidative potential of one or more anti-oxidants acting synergistically may be greater than the sum of the oxidative potential of each component anti-oxidant).

The terms "R'''" in a chemical formula refer to hydrogen or a functional group, each independently selected, unless stated otherwise. In some embodiments the functional group may be an organic group. In some embodiments the functional group may be an alkyl group. In some embodiments, the functional group may be a hydrophobic or hydrophilic group.

Compounds described herein embrace isomers mixtures, racemic, optically active, and optically inactive stereoisomers and compounds.

The Complement System and Inflammation in Tissue Injury

The complement system plays an important role in host defense mechanisms against infectious agents and in the inflammatory response. Under normal physiological conditions, complement proteins exist in body fluids in a latent, or inactive state. In the presence of a pathogen or of an activating stimulus, such as for example a localized inflammatory response, or the in the presence of damaged or apoptotic cells, the proteins react with one another and with surrounding molecules to activate the complement system, resulting ultimately in the formation of the membrane attack complex. It is generally known in the art that three biochemical pathways may activate complement: the classical, alternative, and mannose-binding lectin pathways. Complement proteins C1-C9 are the major components of the classical activation cascade, which is most commonly initiated by binding of C1q to initiator molecules. Regardless of the mechanism by which the complement system is activated, all three pathways converge at the formation of complement proteins C3 and C4. Activation of C3 and C4 ultimately results in the recruitment and activation of the terminal complement proteins C5-C9 and formation of the MAC at the site of the response. Together, the C5b-C9 and the MAC are highly pro-inflammatory. It is believed that aberrant activation or function of the complement system might contribute to the pathophysiology of many diseases with an immune component, such as Alzheimer's disease, asthma, systemic lupus erythematosus, diabetes mellitus, glomerulonephritis, Crohn's disease, atherosclerosis, various forms of arthritis (e.g. osteoarthritis and rheumatoid arthritis), autoimmune heart disease, multiple sclerosis and Age-Related Macular degeneration (ARMD). Deficiencies in terminal pathway components predispose patients to certain autoimmune diseases and infections (particularly meningitis).

CRP is known to be a highly sensitive, but nonspecific, marker of inflammation. CRP was initially discovered due to its ability to react with the C-polysaccharide of the pathogen *pneumococcus*. In addition to C-protein, additional ligands such as phosphocholine and other phospholipids, have been shown to target CRP to sites of infection or pathology. In addition to interacting with various phospholipid ligands, CRP associates with numerous polypeptides. For example, it has been demonstrated that CRP can activate the classical complement pathway by binding to complement protein C1q, stimulate phagocytosis, and bind to immunoglobulin receptors (Fc R), through which it is though to affect the humoral response to disease. It is thought that CRP facilitates complement binding to invading foreign pathogens and to the surface of damaged cells and tissues, thus targeting them for clearance by the innate and adaptive immune system. Recent evidence suggests that chronic elevated levels of circulating CRP are correlated with an increased risk of developing cardiovascular disease later in life.

Tissue injury following certain pathological insults such as, for example, induction of an inflammatory response, ischemia-reperfusion injury or other pathological processes that result in localized tissue necrosis and cell damage may result in the deposition of acute phase inflammatory molecules such as CRP and activated complement proteins or the MAC at the site of injury. Deposition of acute inflammatory mediators and complement system proteins, particularly activated C3b and C5b-C9, at these sites may accelerate tissue damage, at least in part by allowing the formation of damaging immune complexes, recruiting leukocytes and other pro-inflammatory cells to the site of injury, and worsening cell membrane damage by promoting MAC formation on the surface of the cell (reviewed in Black et al., 2004, J. Biol. Chem., Vol. 279, pp 48487-48494, which is incorporated herein by reference). Under normal physiological conditions, the CRP phospholipid ligands phosphocholine, phosphatidylcholine, phosphatidylserine, and the like are not exposed on the surface of cells. Following an injurious insult to a tissue, such as for example a localized inflammatory response, damaged or apoptotic cells expose these phospholipids on their surface. The phospholipids ligands may then be accessible to circulating CRP, which itself is expressed at high levels during the acute phase of an inflammatory response, resulting in the recruitment and deposition of ligand-bound CRP at the site of injury. Ligand-bound or aggregated CRP efficiently activates the classical complement pathway by interacting directly with complement protein C1q. Formation of a biochemical complex between ligand-bound CRP and C1q activates the complement cascade, resulting ultimately in the formation of C3 and C4, which assembles in a fashion similar to that initiated by antibody-antigen complexes.

In an embodiment, administering a carotenoid analog or derivative to a subject may reduce the amount of CRP that is deposited in a body tissue during an inflammatory response. Reducing the amount of CRP recruited to inflamed or otherwise damaged tissue by administering the carotenoid analogs or derivatives embodied herein may at least partially inhibit aberrant activation of terminal complement proteins C5b-C9 and/or formation and deposition of the MAC in the damaged tissue. Reducing tissue deposition of CRP and or terminal complement proteins C5b-C9 and the MAC may prevent more severe or irreversible damage to the tissue and may allow the subject's body to begin appropriate regenerative and/or healing processes.

Age-related macular degeneration (ARMD) is thought to be the result of a lifetime of oxidative insult that results in photoreceptor death within the macula. Recent studies have demonstrated the utility of lutein-based supplementation for the clinical improvement of vision, reduction of ultraviolet (UV)-based inflammation, and potentially the inhibition and/or amelioration of age-related macular degeneration (ARMD).

Recent studies have also implicated the involvement of complement system components and their regulator proteins in contributing to the pathophysiology of macular degeneration, including ARMD. Various components of the terminal complement system, including complement proteins C5b-C9, have been identified in deposits in the macula and surrounding tissues of patients with ARMD, where the complexes were observed in Bruch's membrane, the intercapillary pillars, and within drusen. The observation of complement components in drusen and in the macula and in supporting tissues in both humans and mice suggests that aberrant inflammatory responses, including inappropriate activation of complement or its regulatory components, contribute to the pathophysiology and progression of macular degeneration, including ARMD.

CFH binds to numerous proteins in the serum and on the surface of cells or in the interstitium, including C3b, CRP, heparin, and sialic acid-rich polyanions. Under normal physiological conditions, binding of CFH to activated complement proteins, in particular to C3, on the surface of cells and in the circulation serves to negatively regulate the activation and activity of terminal complement components C5-C9. Additionally, CFH is generally thought to attenuate CRP-dependent activation of the classical complement pathway on the surface of ostensibly normal cells or on cells that have not undergone irreversible damage. CFH function, at least in part, by binding to and inhibiting soluble or cell surface-bound complement protein C3b, thus inhibiting MAC formation on the surface cells and preventing their lysis. Aberrant CFH function has been implicated in contributing to the pathophysiology of numerous inflammatory disorders including, but not limited to, type-II diabetes mellitus, Alzheimer's disease, rheumatoid arthritis, atherosclerosis, and human type II membranoproliferative glomerulonephritis (MPGNII) (reviewed in de Cordoba et al., *Molecular Immunology* Vol. 41, 2004, pp. 355-367, which is incorporated herein by reference). More recently, a strong association between the risk of developing ARMD and the presence of a common polymorphism of the CFH gene has been identified. The most prevalent ARMD risk allele identified encodes a CFH variant bearing a Tyr402→His substitution (Klein et al., published online 10 Mar. 2005; 10.1126/science.1109557; Haines et al., published online 10 Mar. 2005; 10.1126/science.1110359; Edwards et al., published online 10 Mar. 2005; 10.1126/science.1110189, all of which are incorporated herein by reference). The amino acid 402 of CFH maps to a region of the protein that interacts with CRP and heparin. Substitution of the neutral amino acid Tyr with a positively charge His residue is thought to affect the ability of CFH to bind to CRP or heparin. Therefore, in subjects carrying the ARMD risk allele, impaired binding of CFH to CRP may result in an inability of CFH to attenuate MAC formation on the surface of damaged tissues of the macular and surrounding areas, resulting in a net increase in the tissue inflammation and damage. Therapeutic agents that affect deposition of CRP or the MAC in tissues of the macula and surrounding areas would therefore be useful to treat patients with macular degeneration, including ARMD.

In an embodiment, administration of the carotenoid analogs or derivatives described herein to a subject who is developing or who is at risk of developing ARMD may reduce inflammation associated with complement activation in the macula. Reducing inflammation in the macula by administering carotenoid analogs or derivatives may be associated with reduced deposition of CRP and/or terminal complement proteins C5b-C9 and the MAC in the macula and in the surrounding tissues of the in Bruch's membrane, the intercapillary pillars, and within drusen. Reducing inflammation in the macula by administering carotenoid analogs or derivatives may be associated with a reduction in tissue damage and may improve visual acuity and/or halt the deterioration of visual acuity.

Reduction in complement activation by administering the carotenoid analogs or derivatives described herein is not limited to that portion of complement that is acting on the surface of cells in body tissues. On the contrary, the carotenoid analogs and derivatives described herein may inhibit or reduce activation of soluble complement components in the blood plasma or in other body fluids of subjects who have been administered the compounds. Such reduction or inhibition of complement system activity in subjects may result in reduced complement-mediated lysis and cellular damage in tissues or in cells suspended in fluids.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations may be parenterally administered, upon which the spontaneous self-assembly is overcome by interactions with serum and/or tissue components in vivo.

Some specific embodiments may include phosphate derivatives, succinate derivatives, co-antioxidant derivatives (e.g., Vitamin C, Vitamin C analogs, Vitamin C derivatives, Vitamin E, Vitamin E analogs, Vitamin E derivatives, flavonoids, flavonoid analogs, or flavonoid derivatives), or combinations thereof derivatives or analogs of carotenoids. Flavonoids may include, for example, quercetin, xanthohumol, isoxanthohumol, or genistein. Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

In some embodiments, one or more co-antioxidants may be coupled to a carotenoid or carotenoid derivative or analog.

The synthesis of water-soluble and/or water-dispersible carotenoids (e.g., C40) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g. cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. The net overall effect is an improvement in potential clinical utility for the lipophilic carotenoid compounds as therapeutic agents.

In some embodiments, the principles of retrometabolic drug design may be utilized to produce novel soft drugs from the asymmetric parent carotenoid scaffold (e.g., RRR-lutein (β,ε-carotene-3,3'-diol)). For example, lutein scaffold for derivatization was obtained commercially as purified natural plant source material, and was primarily the RRR-stereoisomer (one of 8 potential stereoisomers). Lutein (Scheme 1) possesses key characteristics—similar to starting material astaxanthin—which make it an ideal starting platform for retrometabolic syntheses: (1) synthetic handles (hydroxyl groups) for conjugation, and (2) an excellent safety profile for the parent compound. As stated above, lutein is available commercially from multiple sources in bulk as primarily the RRR-stereoisomer, the primary isomer in the human diet and human retinal tissue.

In some embodiments, carotenoid analogs or derivatives may have increased water solubility and/or water dispersibility relative to some or all known naturally occurring carotenoids. Contradictory to previous research, improved results are obtained with derivatized carotenoids relative to the base carotenoid, wherein the base carotenoid is derivatized with substituents including hydrophilic substituents and/or co-antioxidants.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, a chemical compound including a carotenoid derivative or analog may have the general structure (126):

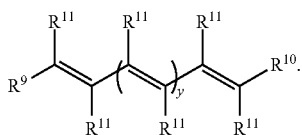
(126)

Each $R^{11}$ may be independently hydrogen or methyl. $R^9$ and $R^{10}$ may be independently H, an acyclic alkene with one or more substituents, or a cyclic ring including one or more substituents. y may be 5 to 12. In some embodiments, y may be 3 to 15. In certain embodiments, the maximum value of y may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be included in a pharmaceutical composition.

In some embodiments, the carotenoid derivatives may include compounds having the structure (128):

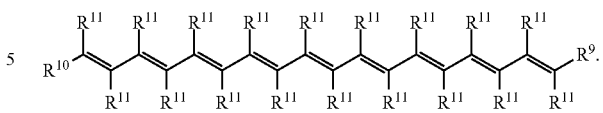
(128)

Each $R^{11}$ may be independently hydrogen, methyl, alkyl, alkenyl, or aromatic substituents. $R^9$ and $R^{10}$ may be independently H, an acyclic alkene with at least one substituent, or a cyclic ring with at least one substituent having general structure (130):

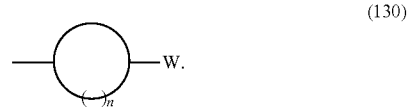
(130)

where n may be between 4 to 10 carbon atoms. W is the substituent.

In some embodiments, each cyclic ring may be independently two or more rings fused together to form a fused ring system (e.g., a bi-cyclic system). Each ring of the fused ring system may independently contain one or more degrees of unsaturation. Each ring of the fused ring system may be independently aromatic. Two or more of the rings forming the fused ring system may form an aromatic system.

In some embodiments, a chemical composition may include a carotenoid derivative having the structure

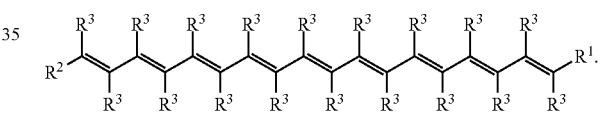

Each $R^3$ may be independently hydrogen or methyl. $R^1$ and $R^2$ may be a cyclic ring including at least one substituent. Each cyclic ring may be independently:

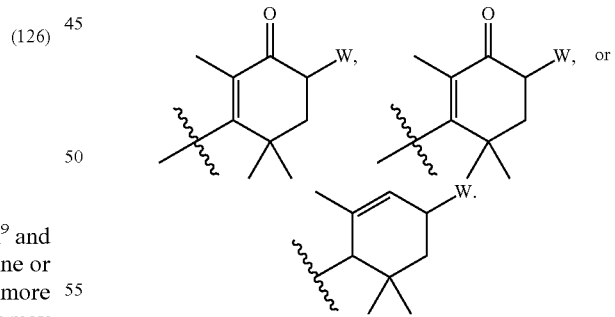

W is the substituent. In some embodiments $R^1$ and $R^2$ may be an acyclic group including at least one substituent. Each acyclic may be:

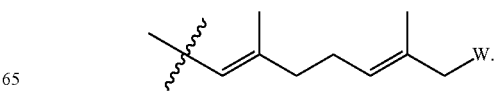

In some embodiments, a chemical composition may include a carotenoid derivative having the structure

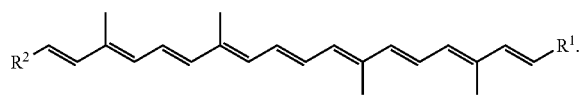

$R^1$ and $R^2$ may be a cyclic ring including at least one substituent. Each cyclic ring may be independently:

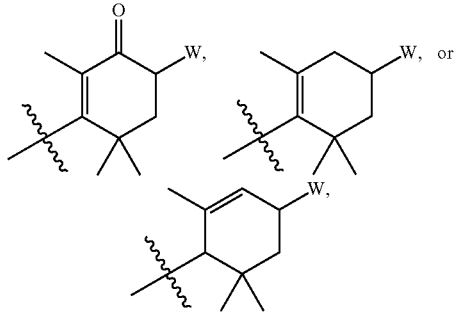

where W is the substituent. In some embodiments $R^1$ and $R^2$ may be an acyclic group including at least one substituent. Each acyclic group may be:

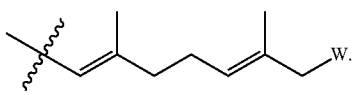

In some embodiments, a method of treating or reducing tissue damage associated with an inflammatory response may include administering to the subject an effective amount of a pharmaceutically acceptable formulation including a synthetic analog or derivative of a carotenoid. The synthetic analog or derivative of the carotenoid may have the structure

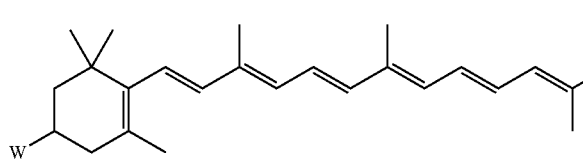

At least one substituent W may independently include

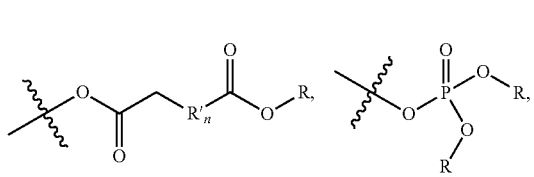

or a co-antioxidant. Each R' may be $CH_2$. n may range from 1 to 9. Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein.

Vitamin E may generally be divided into two categories including tocopherols having a general structure

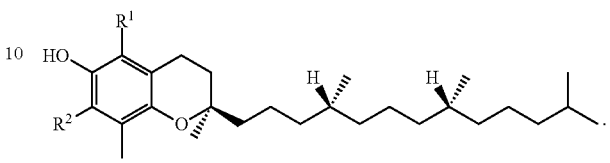

Alpha-tocopherol is used to designate when $R^1=R^2=CH_3$. Beta-tocopherol is used to designate when $R^1=CH_3$ and $R^2=H$. Gamma-tocopherol is used to designate when $R^1=H$ and $R^2=CH_3$. Delta-tocopherol is used to designate when $R^1=R^2=H$.

The second category of Vitamin E may include tocotrienols having a general structure

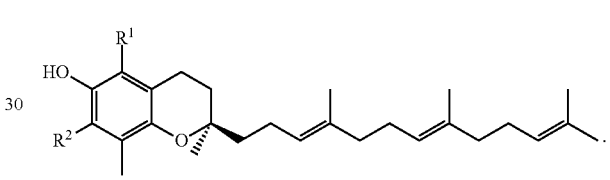

Alpha-tocotrienol is used to designate when $R^1=R^2=CH_3$. Beta-tocotrienol is used to designate when $R^1=CH_3$ and $R^2=H$. Gamma-tocotrienol is used to designate when $R^1=H$ and $R^2=CH_3$. Delta-tocotrienol is used to designate when $R^1=R^2=H$.

Quercetin, a flavonoid, may have the structure

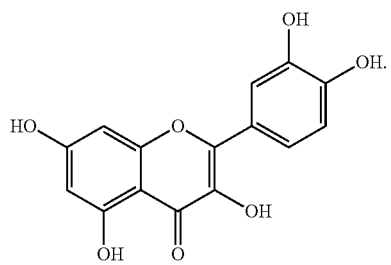 [SMILES: O=c1c(O)c(-c2ccc(O)c(O)c2)oc2cc(O)cc(O)c12]

In some embodiments, the carotenoid analog or derivative may have the structure

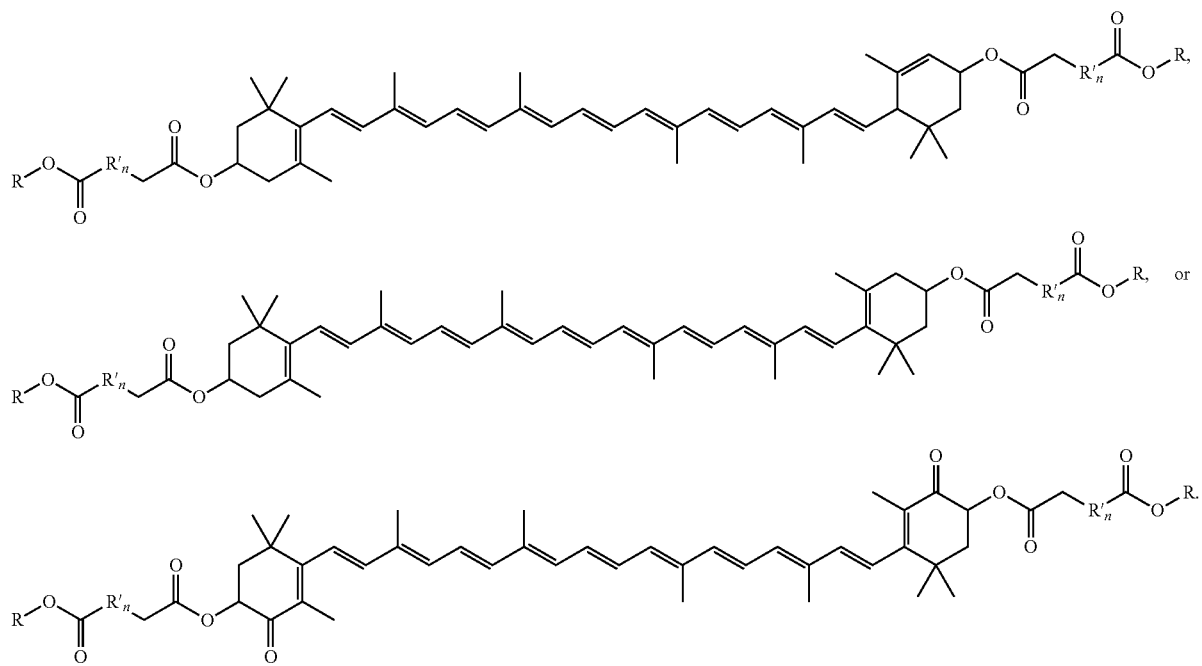

Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives.

Flavonoids may include, for example, quercetin, xanthohumol, isoxanthohumol, or genistein.

In some embodiments, the carotenoid analog or derivative may have the structure

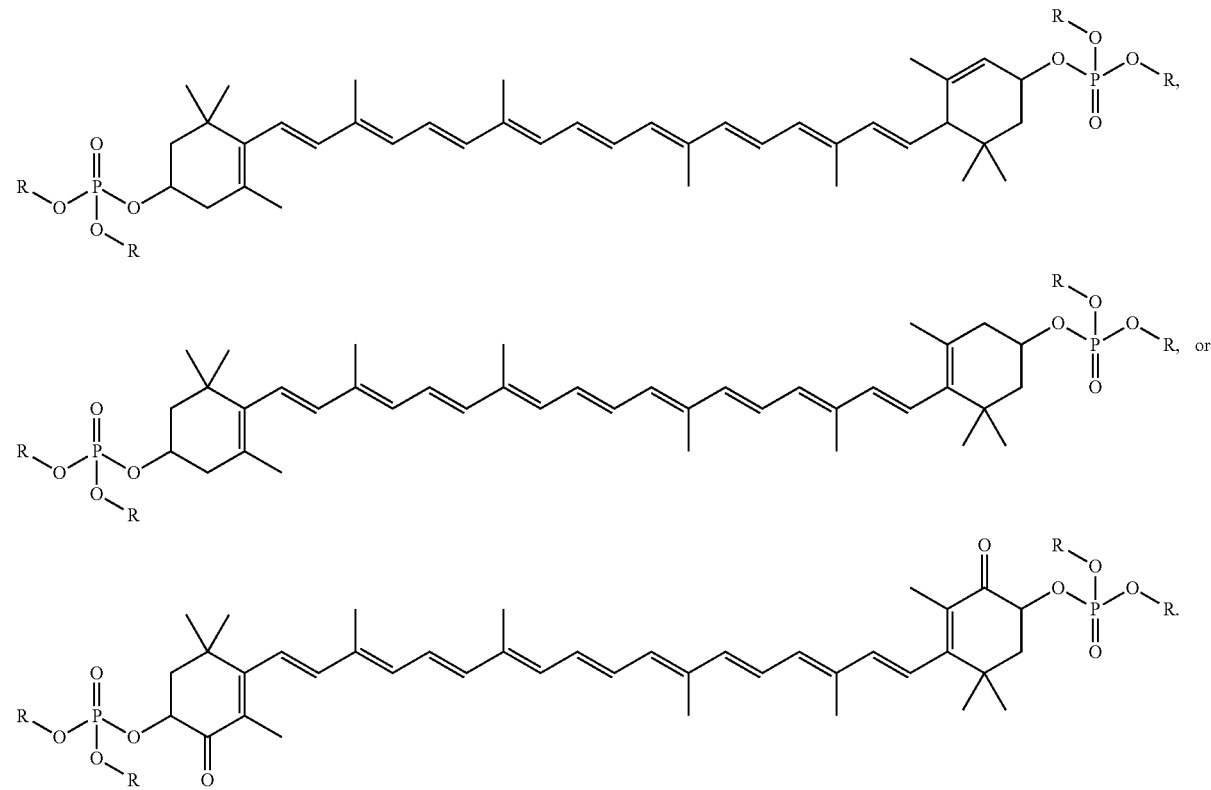

Each R may be independently H, alkyl, aryl, benzyl, Group IA metal (e.g., sodium), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. When R includes Vitamin C, Vitamin C analogs, or Vitamin C derivatives, some embodiments may include carotenoid analogs or derivatives having the structure

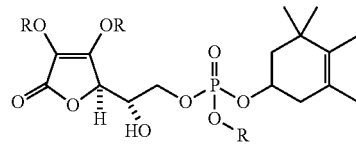

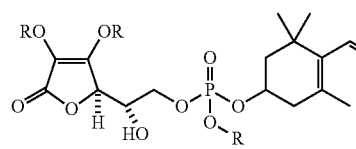

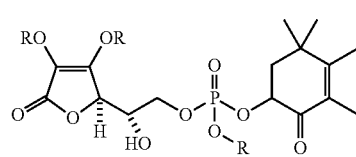

Each R may be independently H, alkyl, aryl, benzyl, or Group IA metal.

In some embodiments, a chemical compound including a carotenoid derivative may have the general structure (132):

(132)

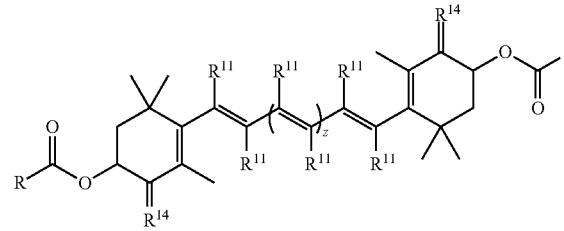

Each $R^{11}$ may be independently hydrogen or methyl. Each $R^{14}$ may be independently O or $H_2$. Each R may be independently $OR^{12}$ or $R^{12}$. Each $R^{12}$ may be independently -alkyl-$NR^{13}_3{}^+$, -aromatic-$NR^{13}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{13}$ may be independently H, alkyl, or aryl. z may range from 5 to 12. In some embodiments, z may range from about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some embodiments, a chemical compound including a carotenoid derivative may have the general structure (134):

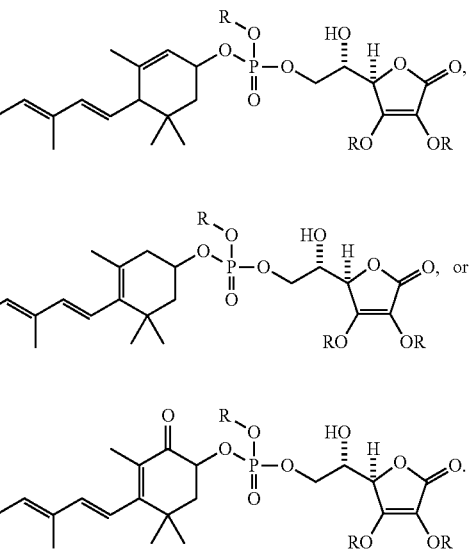

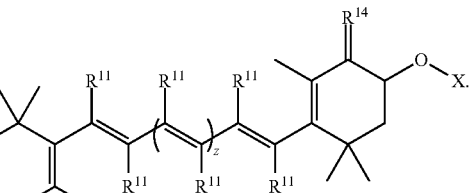

Each $R^{11}$ may be independently hydrogen or methyl. Each $R^{14}$ may be independently O or $H_2$. Each X may be independently

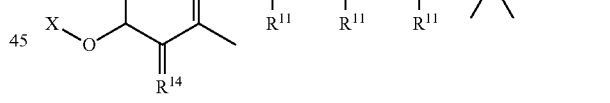

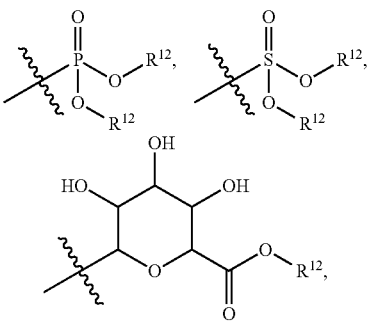

(134)

-alkyl-NR$^{12}_3{}^+$, -aromatic-NR$^{12}_3{}^+$, -alkyl-CO$_2{}^-$, -aromatic-CO$_2{}^-$, -amino acid-NH$_3{}^+$, -phosphorylated amino acid-NH$_3{}^+$, polyethylene glycol, dextran, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each R$^{12}$ is independently -alkyl-NR$^{13}_3{}^+$, -aromatic-NR$^{13}_3{}^+$, -alkyl-CO$_2{}^-$, -aromatic-CO$_2{}^-$, -amino acid-NH$_3{}^+$, -phosphorylated amino acid-NH$_3{}^+$, polyethylene glycol, dextran, H, alkyl, aryl, benzyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or Group IA salt. Each R$^{13}$ may be independently H, alkyl, or aryl. z may range from 5 to 12. In some embodiments, z may range from about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some non-limiting examples, five- and/or six-membered ring carotenoid derivatives may be more easily synthesized. Synthesis may come more easily due to, for example, the natural stability of five- and six-membered rings. Synthesis of carotenoid derivatives including five- and/or six-membered rings may be more easily synthesized due to, for example, the availability of naturally occurring carotenoids including five- and/or six-membered rings. In some embodiments, five-membered rings may decrease steric hindrance associated with rotation of the cyclic ring around the molecular bond connecting the cyclic ring to the polyene chain. Reducing steric hindrance may allow greater overlap of any π oribitals within a cyclic ring with the polyene chain, thereby increasing the degree of conjugation and effective chromophore length of the molecule. This may have the salutatory effect of increasing antioxidant capacity of the carotenoid derivatives.

In some embodiments, a substituent (W) may be at least partially hydrophilic. A hydrophilic substituent may assist in increasing the water solubility of a carotenoid derivative. In some embodiments, a carotenoid derivative may be at least partially water-soluble. The cyclic ring may include at least one chiral center. The acyclic alkene may include at least one chiral center. The cyclic ring may include at least one degree of unsaturation. In some cyclic ring embodiments, the cyclic ring may be aromatic. One or more degrees of unsaturation within the ring may assist in extending the conjugation of the carotenoid derivative. Extending conjugation within the carotenoid derivative may have the salutatory effect of increasing the antioxidant properties of the carotenoid derivatives. In some embodiments, the substituent W may include, for example, a carboxylic acid, an amino acid, an ester, an alkanol, an amine, a phosphate, a succinate, a glycinate, an ether, a glucoside, a sugar, or a carboxylate salt.

In some embodiments, each substituent —W may independently include —XR. Each X may independently include O, N, or S. In some embodiments, each substituent —W may independently comprises amino acids, esters, carbamates, amides, carbonates, alcohol, phosphates, or sulfonates. In some substituent embodiments, the substituent may include, for example (d) through (uu):

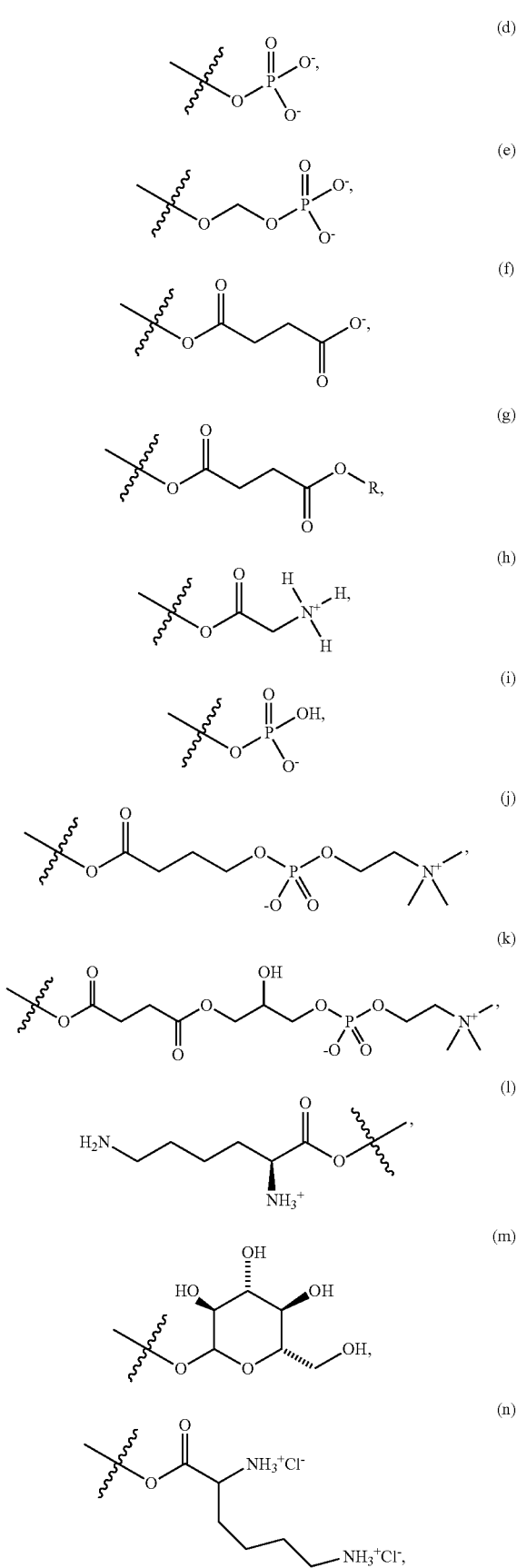

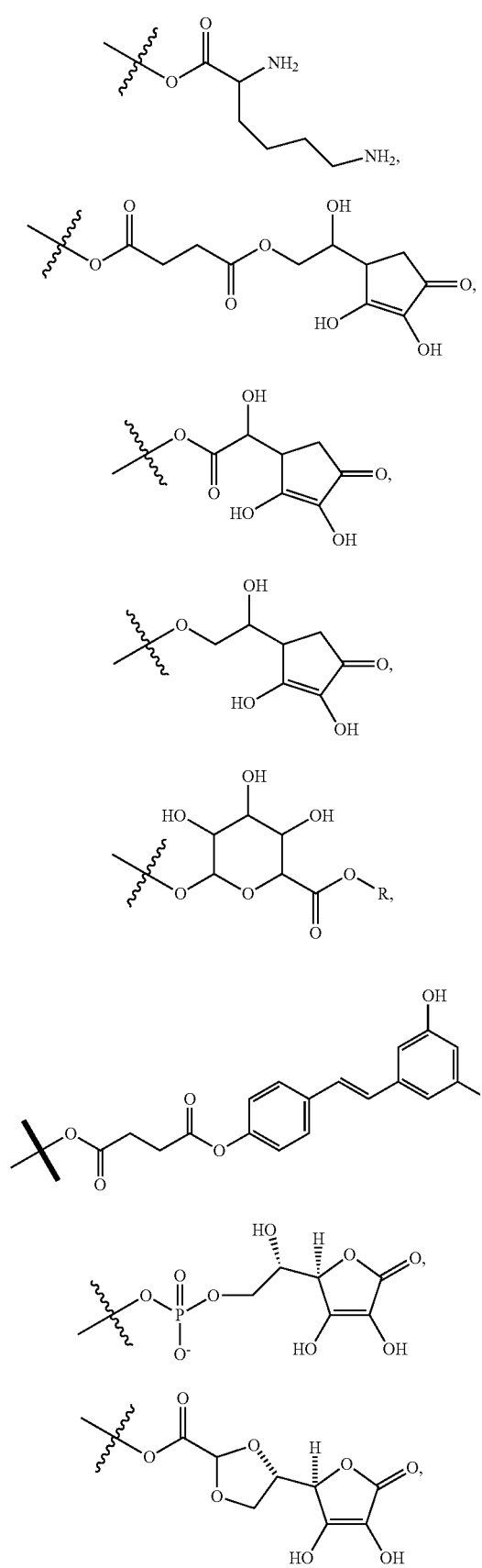
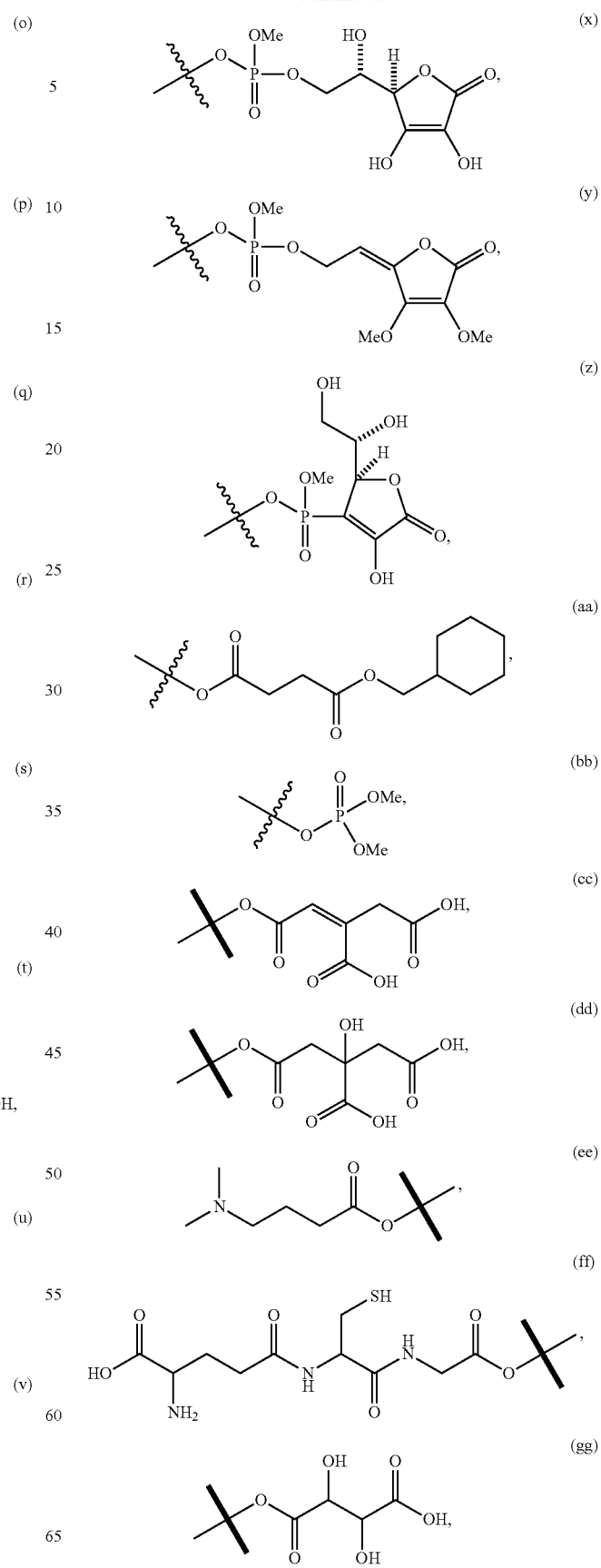

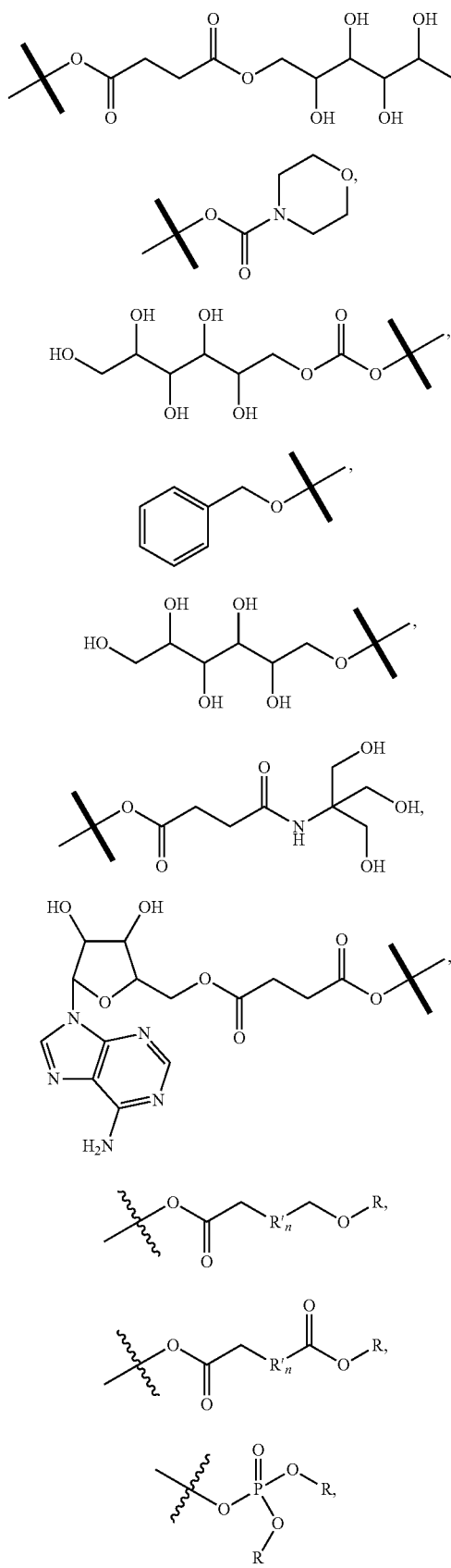
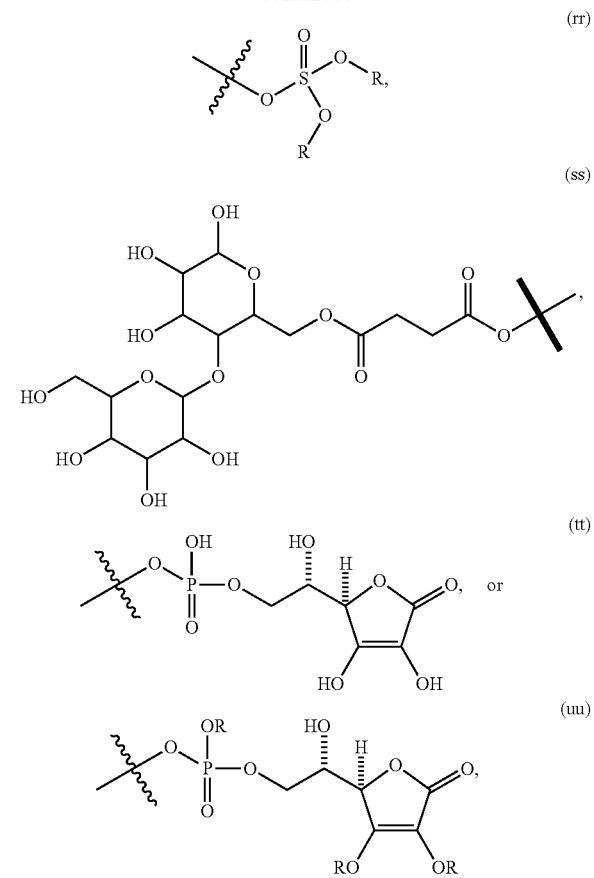

where each R is, for example, independently -alkyl-$NR^{12}_3{}^+$, -aromatic-$NR^{12}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each R' may be $CH_2$. n may range from 1 to 9. In some embodiments, substituents may include any combination of (d) through (uu). In some embodiments, negatively charged substituents may include Group IA metals, one metal or a combination of different Group IA metals in an embodiment with more than one negatively charged substituent, as counter ions. Group IA metals may include, but are not limited to, sodium, potassium, and/or lithium.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/mL. In certain embodiments, water-soluble carotenoid analogs or derivatives may have a water solubility of greater than about 10 mg/mL. In certain embodiments, water-soluble carotenoid analogs or derivatives may have a water solubility of greater than about 20 mg/mL. In some embodiments, water-soluble carotenoid analogs or derivatives may have a water solubility of greater than about 50 mg/mL.

Naturally occurring carotenoids such as xanthophyll carotenoids of the C40 series, which includes commercially important compounds such as lutein, zeaxanthin, and astaxanthin, have poor aqueous solubility in the native state. Varying the chemical structure(s) of the esterified moieties may vastly increase the aqueous solubility and/or dispersibility of derivatized carotenoids.

In some embodiments, highly water-dispersible C40 carotenoid derivatives may include natural source RRR-lutein (β,ε-carotene-3,3'-diol) derivatives. Derivatives may be synthesized by esterification with inorganic phosphate and succinic acid, respectively, and subsequently converted to the sodium salts. Deep orange, evenly colored aqueous suspensions were obtained after addition of these derivatives to USP-purified water. Aqueous dispersibility of the disuccinate sodium salt of natural lutein was 2.85 mg/mL; the diphosphate salt demonstrated a>10-fold increase in dispersibility at 29.27 mg/mL. Aqueous suspensions may be obtained without the addition of heat, detergents, co-solvents, or other additives.

The direct aqueous superoxide scavenging abilities of these derivatives were subsequently evaluated by electron paramagnetic resonance (EPR) spectroscopy in a well-characterized in vitro isolated human neutrophil assay. The derivatives may be potent (millimolar concentration) and nearly identical aqueous-phase scavengers, demonstrating dose-dependent suppression of the superoxide anion signal (as detected by spin-trap adducts of DEPMPO) in the millimolar range. Evidence of card-pack aggregation was obtained for the diphosphate derivative with UV-Vis spectroscopy (discussed herein), whereas limited card-pack and/or head-to-tail aggregation was noted for the disuccinate derivative. These lutein-based soft drugs may find utility in those commercial and clinical applications for which aqueous-phase singlet oxygen quenching and direct radical scavenging may be required.

The absolute size of a carotenoid derivative (in 3 dimensions) is important when considering its use in biological and/or medicinal applications. Some of the largest naturally occurring carotenoids are no greater than about $C_{50}$. This is probably due to size limits imposed on molecules requiring incorporation into and/or interaction with cellular membranes. Cellular membranes may be particularly co-evolved with molecules of a length of approximately 30 nm. In some embodiments, carotenoid derivatives may be greater than or less than about 30 nm in size. In certain embodiments, carotenoid derivatives may be able to change conformation and/or otherwise assume an appropriate shape, which effectively enables the carotenoid derivative to efficiently interact with a cellular membrane.

Although the above structure, and subsequent structures, depict alkenes in the E configuration this should not be seen as limiting. Compounds discussed herein may include embodiments where alkenes are in the Z configuration or include alkenes in a combination of Z and E configurations within the same molecule. The compounds depicted herein may naturally convert between the Z and E configuration and/or exist in equilibrium between the two configurations.

In an embodiment, a chemical compound may include a carotenoid derivative having the structure (136)

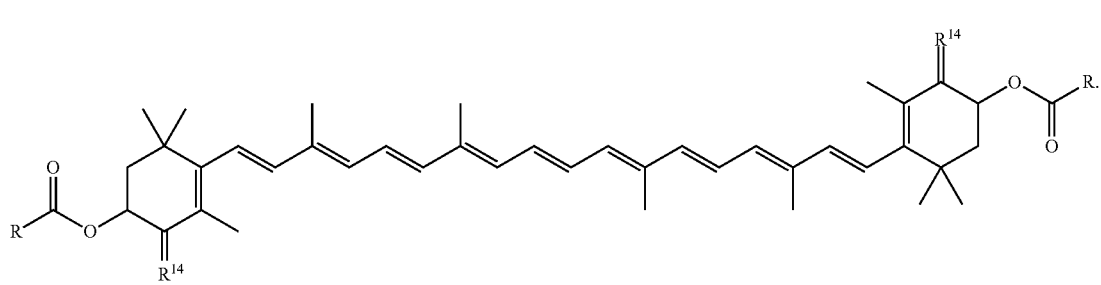

(136)

Each $R^{14}$ may be independently O or $H_2$. Each R may be independently $OR^{12}$ or $R^{12}$. Each $R^{12}$ may be independently -alkyl-$NR^{13}_3{}^+$, -aromatic-$NR^{13}_3{}^+$, -aromatic-$CO_2{}^-$, -amino acid-$NH_3{}^+$, -phosphorylated amino acid-$NH_3{}^+$, polyethylene glycol, dextran, H, alkyl, peptides, poly-lysine, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. In addition, each $R^{13}$ may be independently H, alkyl, or aryl. The carotenoid derivative may include at least one chiral center.

In a specific embodiment where $R^{14}$ is $H_2$, the carotenoid derivative may have the structure (138)

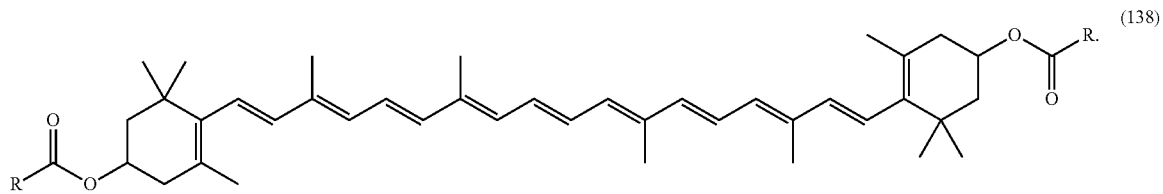

(138)

In a specific embodiment where $R^{14}$ is O, the carotenoid derivative may have the structure (140)

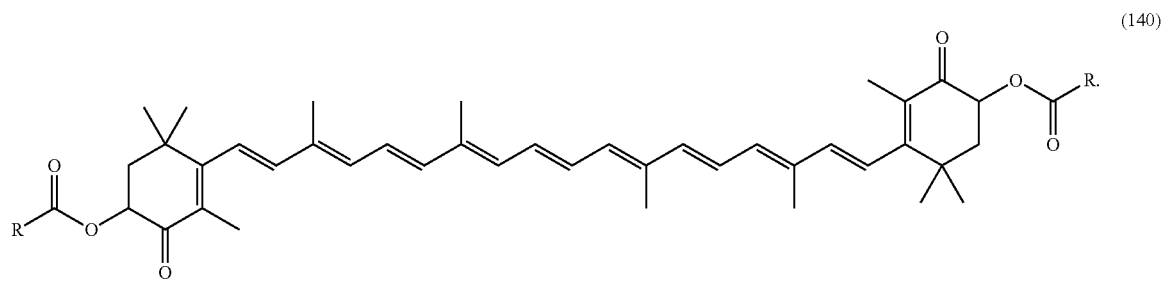
(140)

In an embodiment, a chemical compound may include a carotenoid derivative having the structure (142)

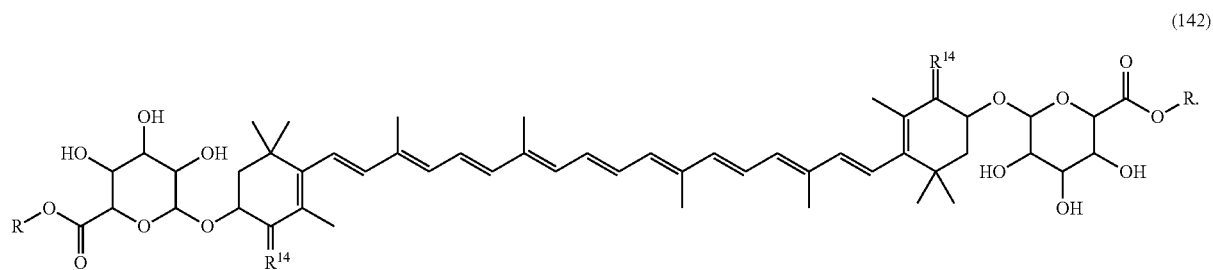
(142)

Each $R^{14}$ may be independently O or $H_2$. Each R may be independently H, alkyl, benzyl, Group IA metal, co-antioxidant, or aryl. The carotenoid derivative may include at least one chiral center. In a specific embodiment $R^{14}$ may be $H_2$, the carotenoid derivative having the structure (144)

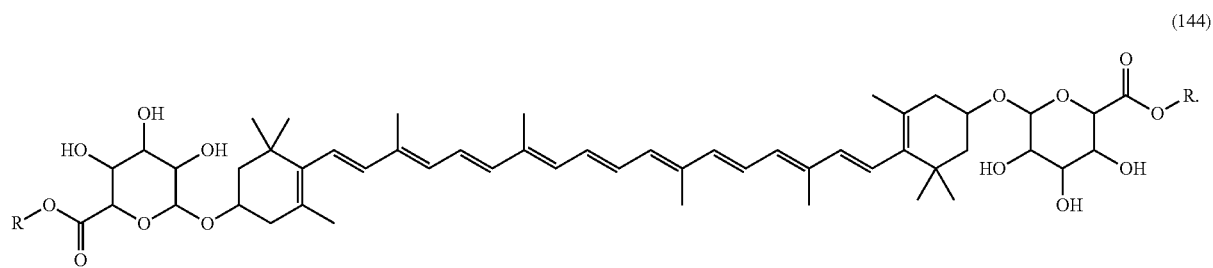
(144)

In a specific embodiment where $R^{14}$ is O, the carotenoid derivative may have the structure (146)

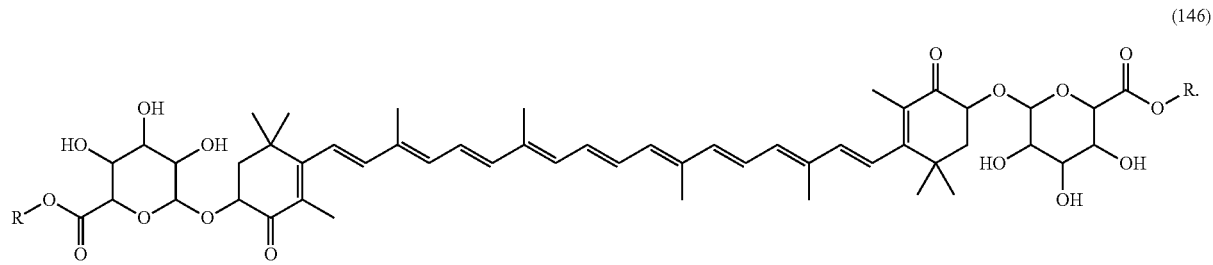
(146)

In an embodiment, a chemical compound may include a carotenoid derivative having the structure (148)

Group IA metal, or co-antioxidant (e.g. Vitamin C, Vitamin C analogs, Vitamin C derivatives, Vitamin E, Vitamin E analogs,

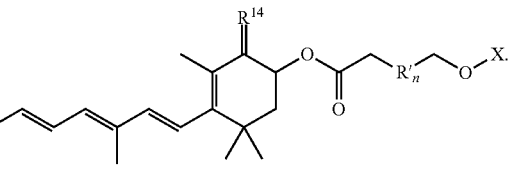
(148)

Each $R^{14}$ may be independently O or $H_2$. Each R' may be $CH_2$. n may range from 1 to 9. Each X may be independently

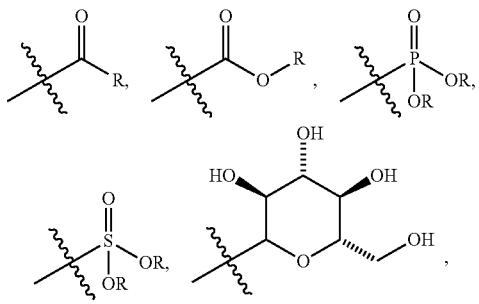

Vitamin E derivatives, flavonoids, flavonoid analogs, or flavonoid derivatives). Each R may be independently -alkyl-$NR^{12}_3{}^+$, -aromatic-$NR^{12}_3{}^+$, -aromatic-$CO_2{}^-$, -amino acid-$NH_3{}^+$, -phosphorylated amino acid-$NH_3{}^+$, polyethylene glycol, dextran, H, alkyl, Group IA metal, benzyl, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{12}$ may be independently H, alkyl, or aryl. The carotenoid derivative may include at least one chiral center.

In a specific embodiment where $R^{14}$ is $H_2$, the carotenoid derivative may have the structure (150)

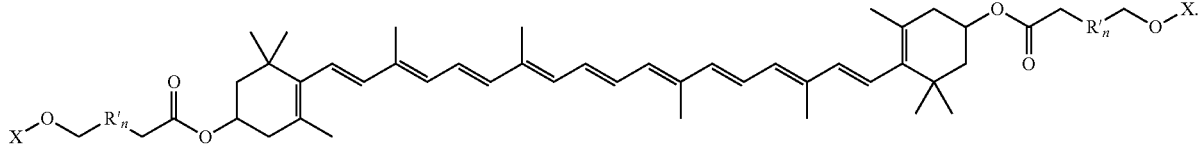
(150)

In a specific embodiment where $R^{14}$ is O, the carotenoid derivative may have the structure (152)

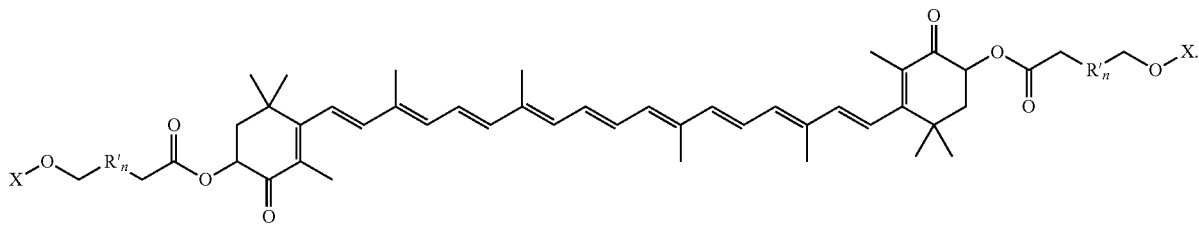
(152)

In an embodiment, a chemical compound may include a carotenoid derivative having the structure (148)

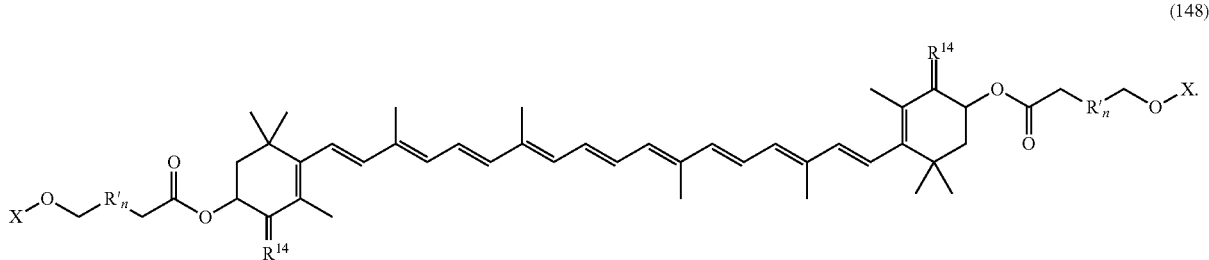

(148)

Each $R^{14}$ may be independently O or $H_2$. Each R' may be $CH_2$. n may range from 1 to 9. Each X may be independently

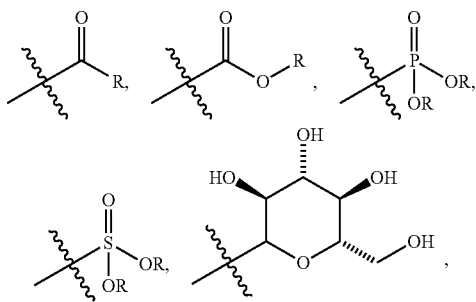

Vitamin E derivatives, flavonoids, flavonoid analogs, or flavonoid derivatives). Each R may be independently -alkyl-$NR^{12}{}_3{}^+$, -aromatic-$NR^{12}{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{12}$ may be independently H, alkyl, or aryl. The carotenoid derivative may include at least one chiral center.

In a specific embodiment where $R^{14}$ is $H_2$, the carotenoid derivative may have the structure (150)

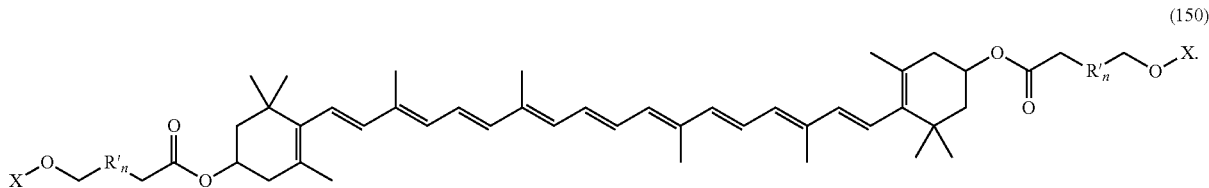

(150)

In a specific embodiment where $R^{14}$ is O, the carotenoid derivative may have the structure (152)

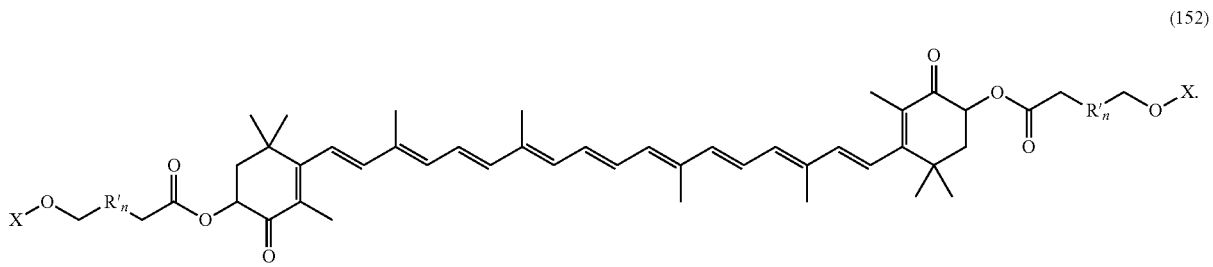

(152)

In an embodiment, a chemical compound may include a carotenoid derivative having the structure (154)

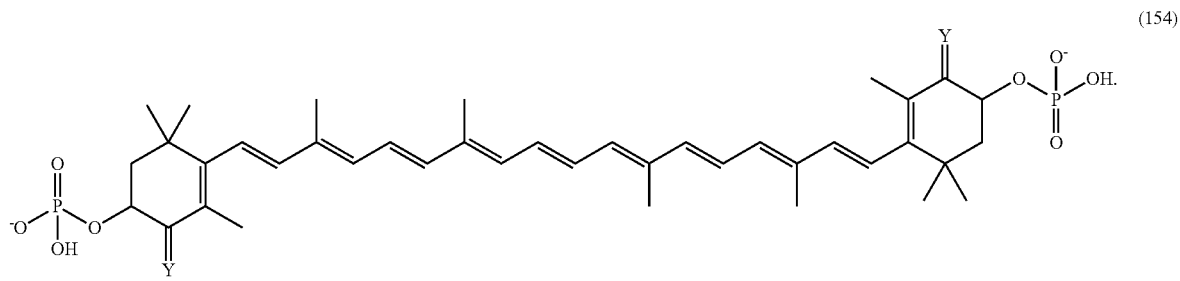

(154)

Each $R^{14}$ may be independently O or $H_2$. The carotenoid derivative may include at least one chiral center. In a specific embodiment $R^{14}$ may be $H_2$, the carotenoid derivative having the structure (156)

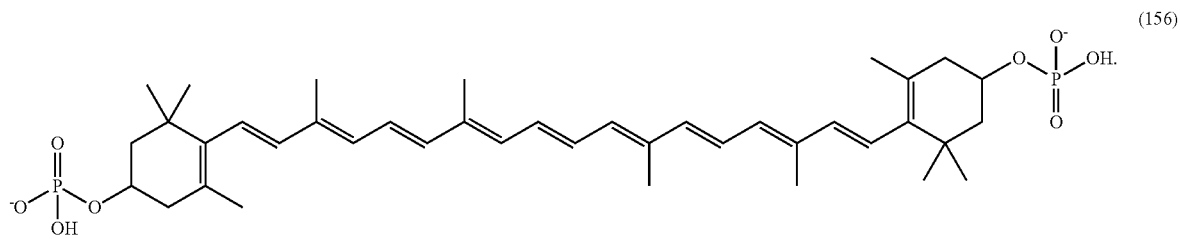

(156)

In a specific embodiment where $R^{14}$ is O, the carotenoid derivative may have the structure (158)

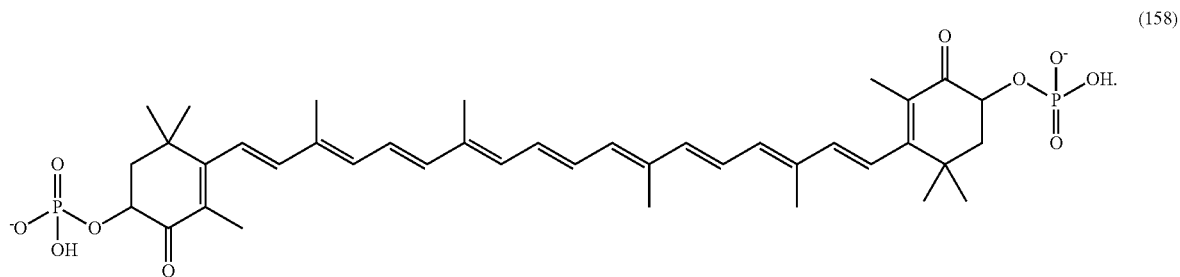

(158)

In some embodiments, a chemical compound may include a disuccinic acid ester carotenoid derivative having the structure (160)

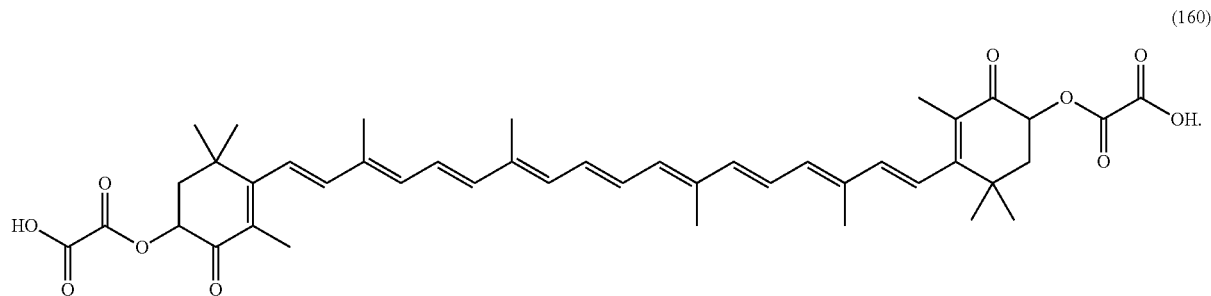 [SMILES: CC1=C(/C=C/C(C)=C/C=C/C(C)=C/C=C/C=C(C)/C=C/C=C(C)/C=C/C2=C(C)C(=O)C(OC(=O)C(=O)O)CC2(C)C)C(C)(C)CC(OC(=O)C(=O)O)C1=O]

(160)

In some embodiments, a chemical compound may include a disodium salt disuccinic acid ester carotenoid derivative having the structure (162)

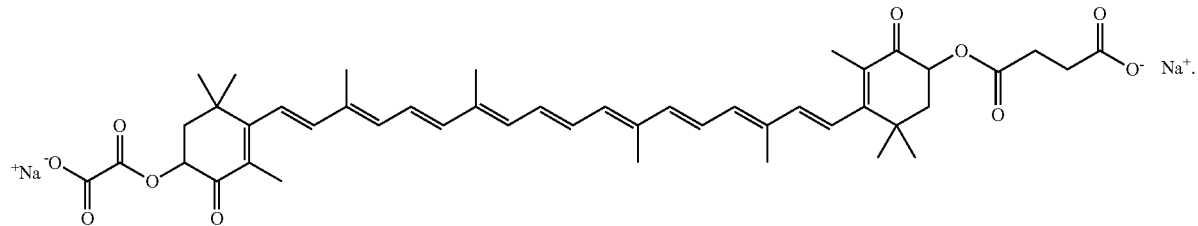

(162)

In some embodiments, a chemical compound may include a carotenoid derivative with a co-antioxidant, in particular one or more analogs or derivatives of vitamin C (i.e., L ascorbic acid) coupled to a carotenoid. Some embodiments may include carboxylic acid and/or carboxylate derivatives of vitamin C coupled to a carotenoid (e.g., structure (164))

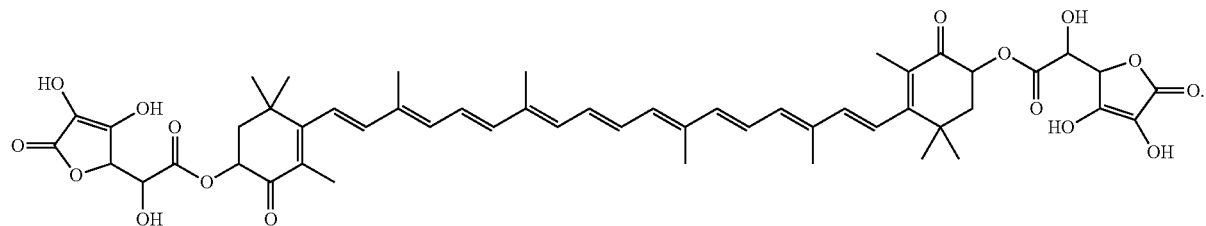

(164)

*Carbohydr. Res.* 1978, 60, 251-258, herein incorporated by reference, discloses oxidation at C-6 of ascorbic acid as depicted in EQN. 5.

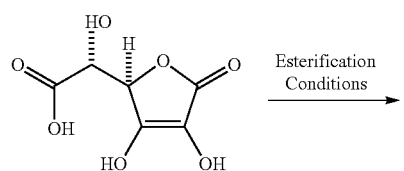

(5)

-continued

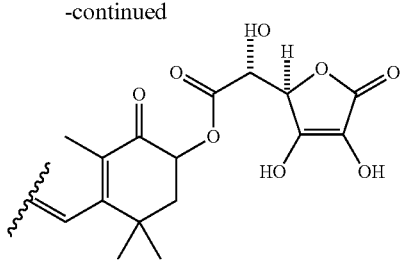

Some embodiments may include vitamin C and/or vitamin C analogs or derivatives coupled to a carotenoid. Vitamin C may be coupled to the carotenoid via an ether linkage (e.g., structure (166))

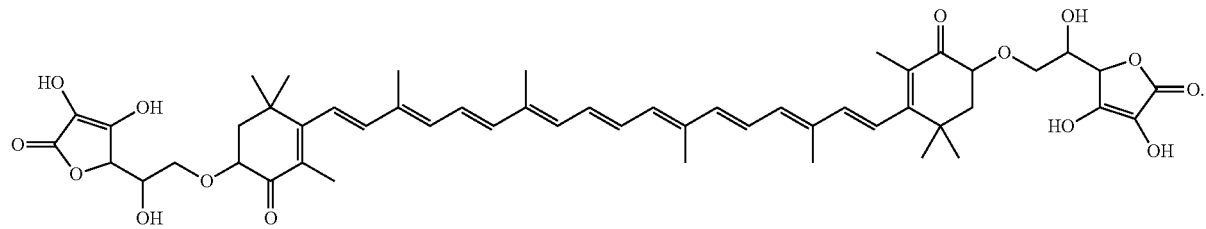

(166)

Some embodiments may include vitamin C disuccinate analogs or derivatives coupled to a carotenoid (e.g., structure (168))

In some embodiments, vitamin C may be selectively esterified. Vitamin C may be selectively esterified at the C-3 position (e.g., EQN. 2). *J. Org. Chem.* 2000, 65, 911-913, herein

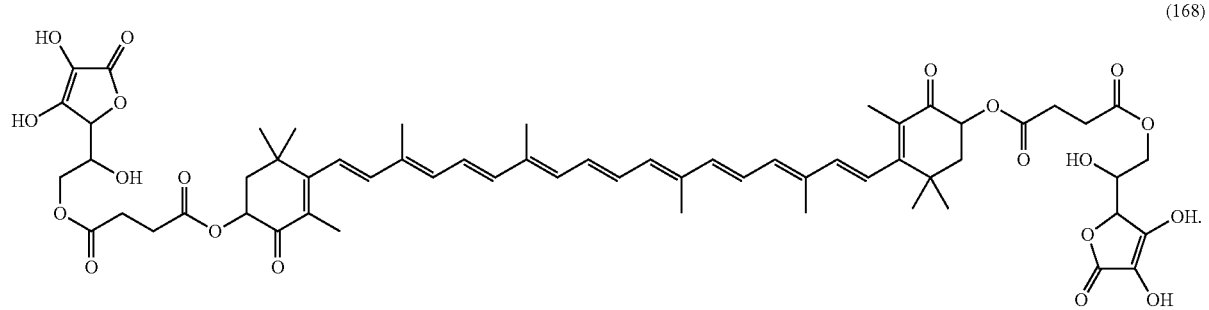 [SMILES: CC1=C(/C=C/C(C)=C/C=C/C(C)=C/C=C/C=C(C)/C=C/C=C(C)/C=C/C2=C(C)C(=O)C(OC(=O)CCC(=O)OCC(O)C3OC(=O)C(O)=C3O)CC2(C)C)C(C)(C)CC(OC(=O)CCC(=O)OCC(O)C2OC(=O)C(O)=C2O)C1=O]

(168)

Some embodiments may include solutions or pharmaceutical preparations of carotenoids and/or carotenoid derivatives combined with co-antioxidants, in particular vitamin C and/or vitamin C analogs or derivatives. Pharmaceutical preparations may include about a 2:1 ratio of vitamin C to carotenoid respectively.

In some embodiments, co-antioxidants (e.g., vitamin C) may increase solubility of the chemical compound. In certain embodiments, co-antioxidants (e.g., vitamin C) may decrease toxicity associated with at least some carotenoid analogs or derivatives. In certain embodiments, co-antioxidants (e.g., vitamin C) may increase the potency of the chemical compound synergistically. Co-antioxidants may be coupled (e.g., a covalent bond) to the carotenoid derivative. Co-antioxidants may be included as a part of a pharmaceutically acceptable formulation.

In some embodiments, a carotenoid (e.g., astaxanthin) may be coupled to vitamin C forming an ether linkage. The ether linkage may be formed using the Mitsunobu reaction as in EQN. 1.

incorporated by reference, discloses selective esterification at C-3 of unprotected ascorbic acid with primary alcohols.

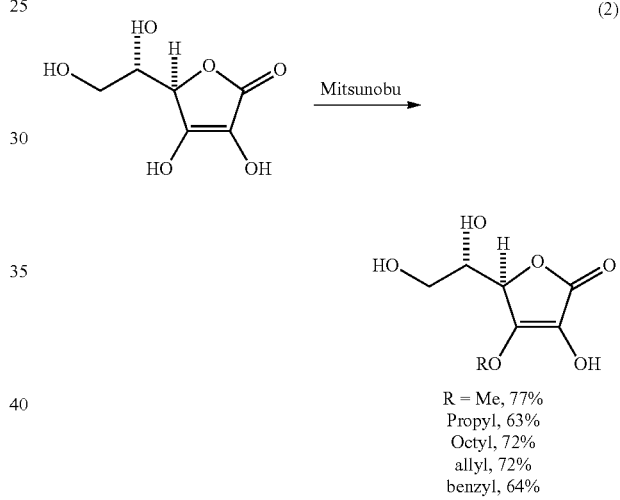

In some embodiments, a carotenoid may be coupled to vitamin C. Vitamin C may be coupled to the carotenoid at the C-6, C-5 diol position as depicted in EQNS. 3 and 4 forming an acetal.

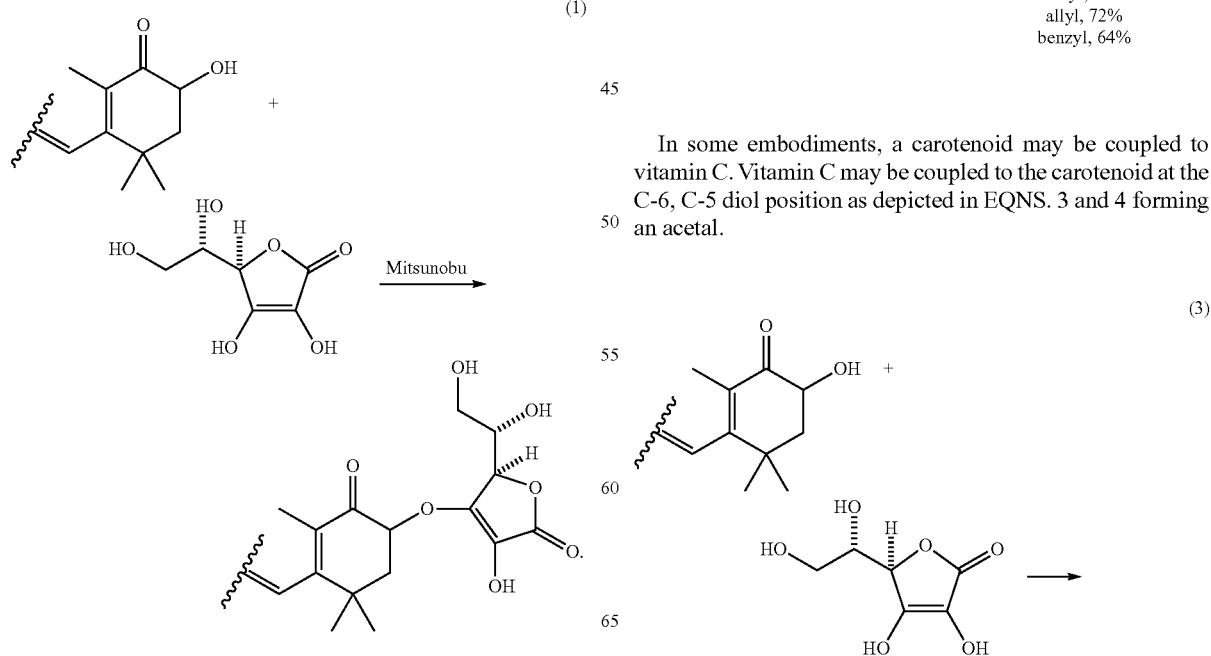

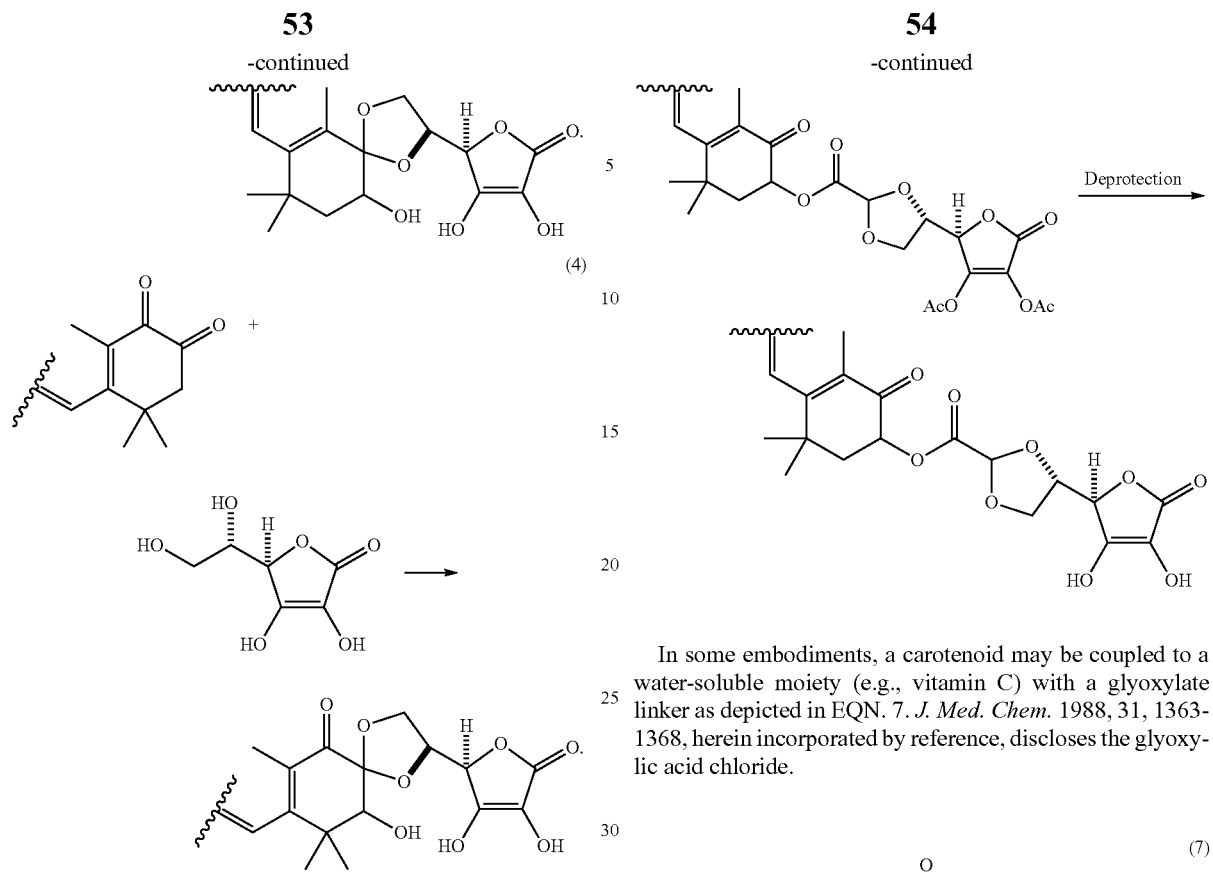

In some embodiments, a carotenoid may be coupled to a water-soluble moiety (e.g., vitamin C) with a glyoxylate linker as depicted in EQN. 6. *Tetrahedron* 1989, 22, 6987-6998, herein incorporated by reference, discloses similar acetal formations.

In some embodiments, a carotenoid may be coupled to a water-soluble moiety (e.g., vitamin C) with a glyoxylate linker as depicted in EQN. 7. *J. Med. Chem.* 1988, 31, 1363-1368, herein incorporated by reference, discloses the glyoxylic acid chloride.

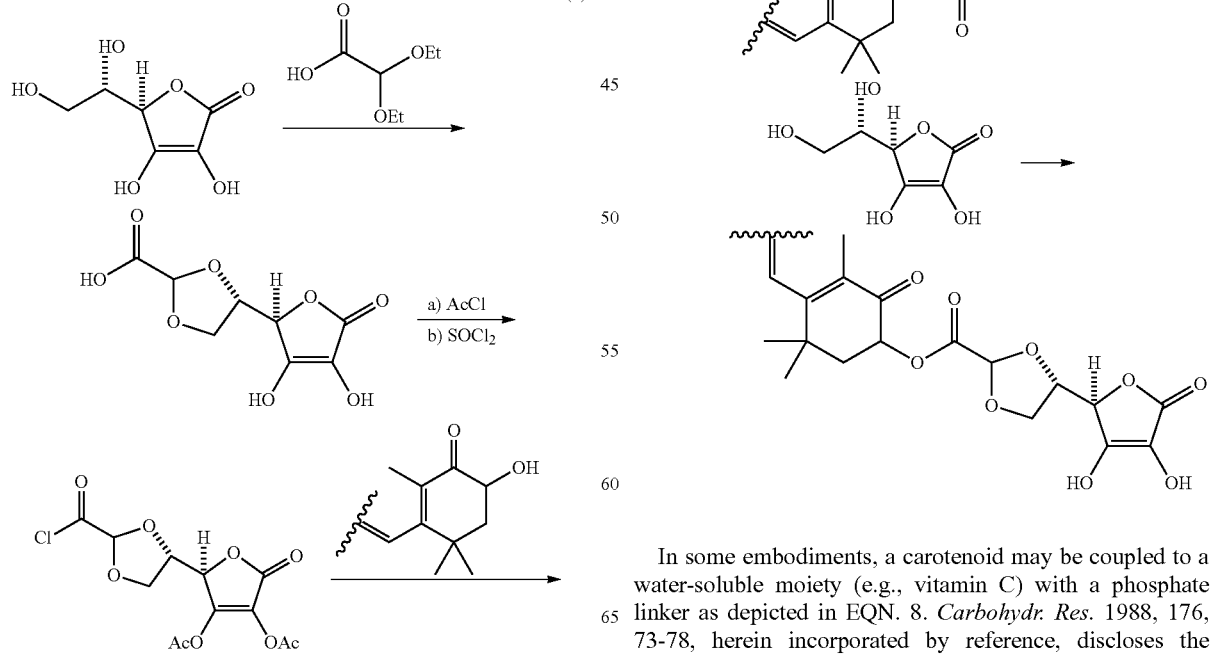

In some embodiments, a carotenoid may be coupled to a water-soluble moiety (e.g., vitamin C) with a phosphate linker as depicted in EQN. 8. *Carbohydr. Res.* 1988, 176, 73-78, herein incorporated by reference, discloses the L-ascorbate 6-phosphate.

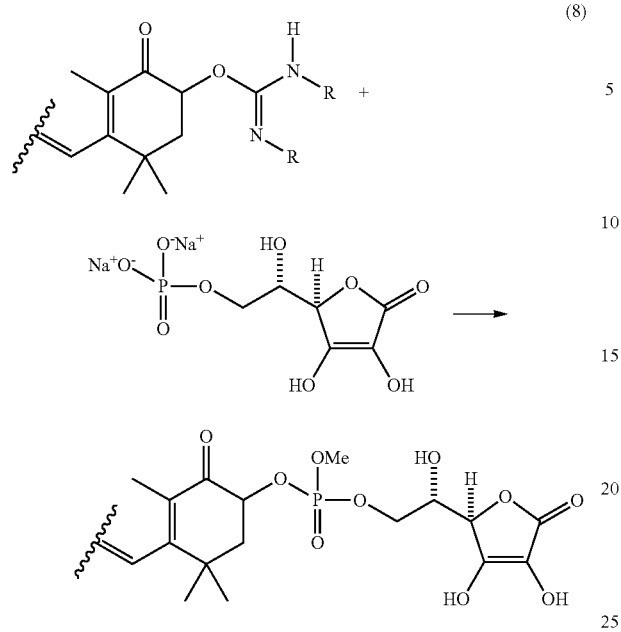

(8)

In some embodiments, a carotenoid may be coupled to a water-soluble moiety (e.g., vitamin C) with a phosphate linker as depicted in EQN. 9. Carbohydr. Res. 1979, 68, 313-319, herein incorporated by reference, discloses the 6-bromo derivative of vitamin C. Carbohydr. Res. 1988, 176, 73-78, herein incorporated by reference, discloses the 6-bromo derivative of vitamin C's reaction with phosphates.

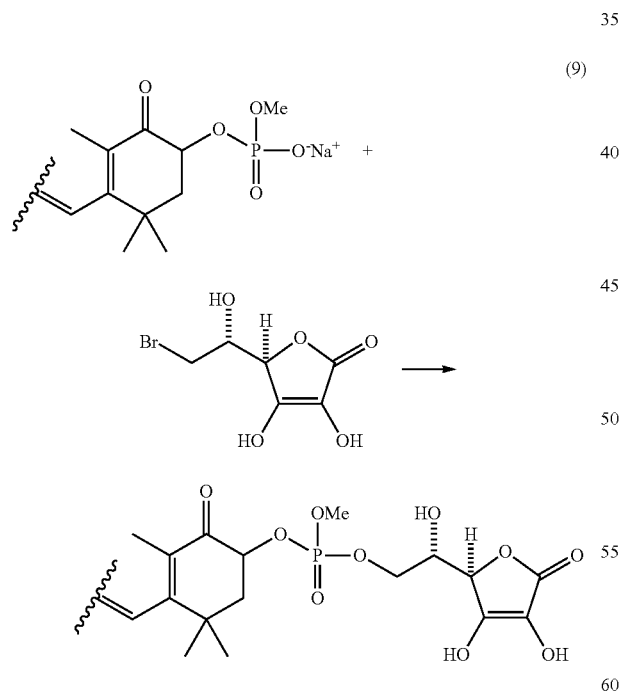

(9)

In some embodiments, a carotenoid may be coupled to a water-soluble moiety (e.g., vitamin C) with a phosphate linker as depicted in EQN. 10. J. Med Chem. 2001, 44, 1749-1757 and J. Med Chem. 2001, 44, 3710-3720, herein incorporated by reference, disclose the allyl chloride derivative and its reaction with nucleophiles, including phosphates, under mild basic conditions.

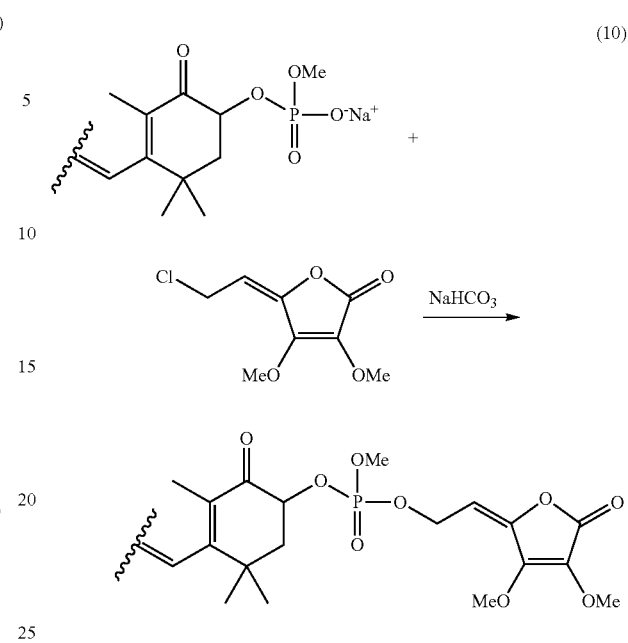

(10)

In some embodiments, a carotenoid may be coupled to a water-soluble moiety (e.g., vitamin C) with a phosphate linker as depicted in EQN. 11. Vitamin C may be coupled to the carotenoid using selective esterification at C-3 of unprotected ascorbic acid with primary alcohols.

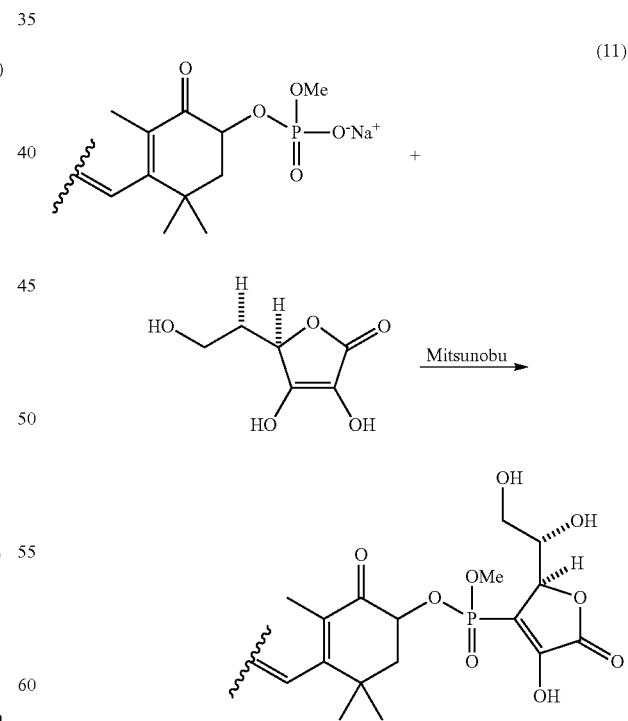

(11)

In some embodiments, a carotenoid may be coupled to a water-soluble moiety (e.g., vitamin C) with a phosphate linker as in 242. Structure 242 may include one or more counterions (e.g., Group IA metals).

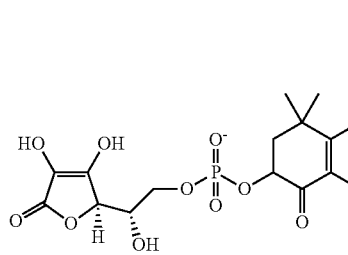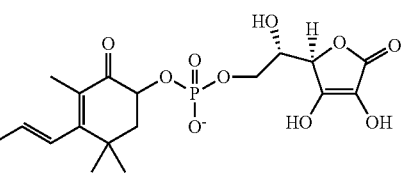

EQN. 12 depicts an example of a synthesis of a protected form of 242.

(12)

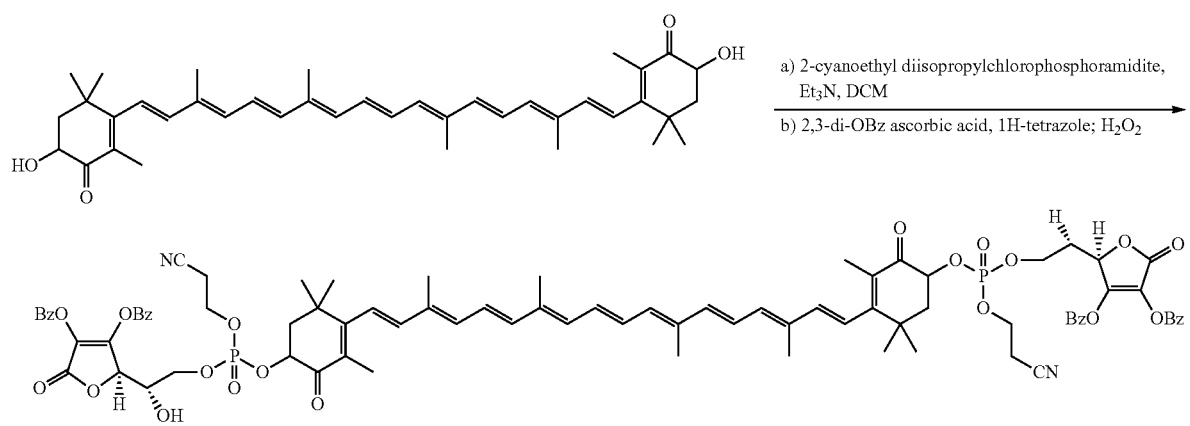

In some embodiments, a chemical compound may include a carotenoid derivative including one or more amino acids (e.g., lysine) and/or amino acid analogs or derivatives (e.g., lysine hydrochloric acid salt) coupled to a carotenoid (e.g., structure (170)).

(170)

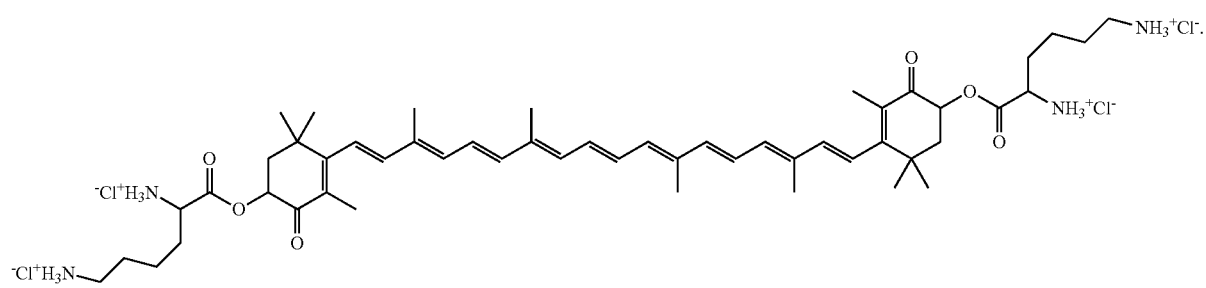

In some embodiments, a carotenoid analog or derivative may include:

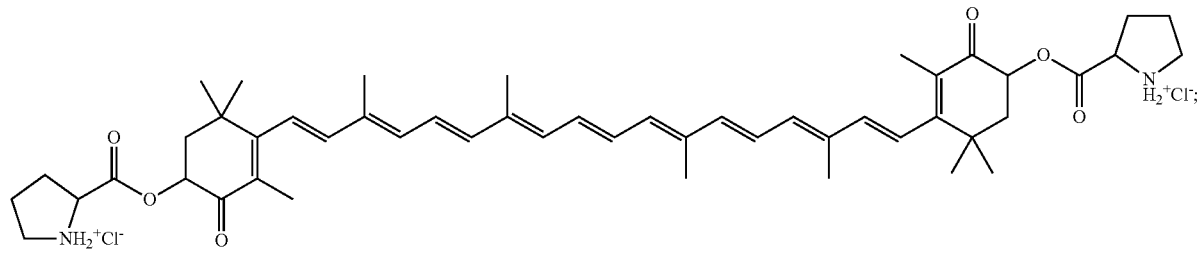

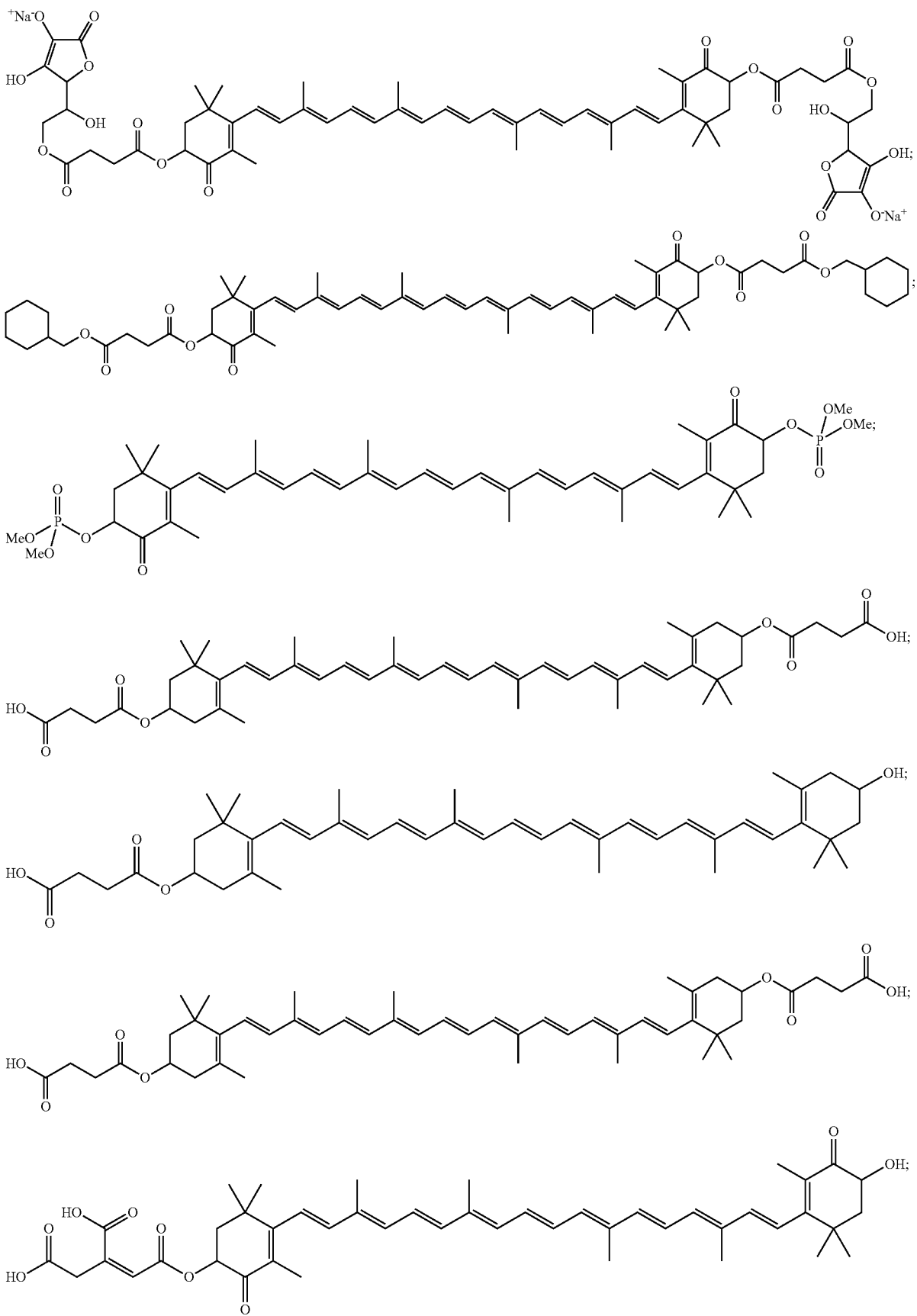

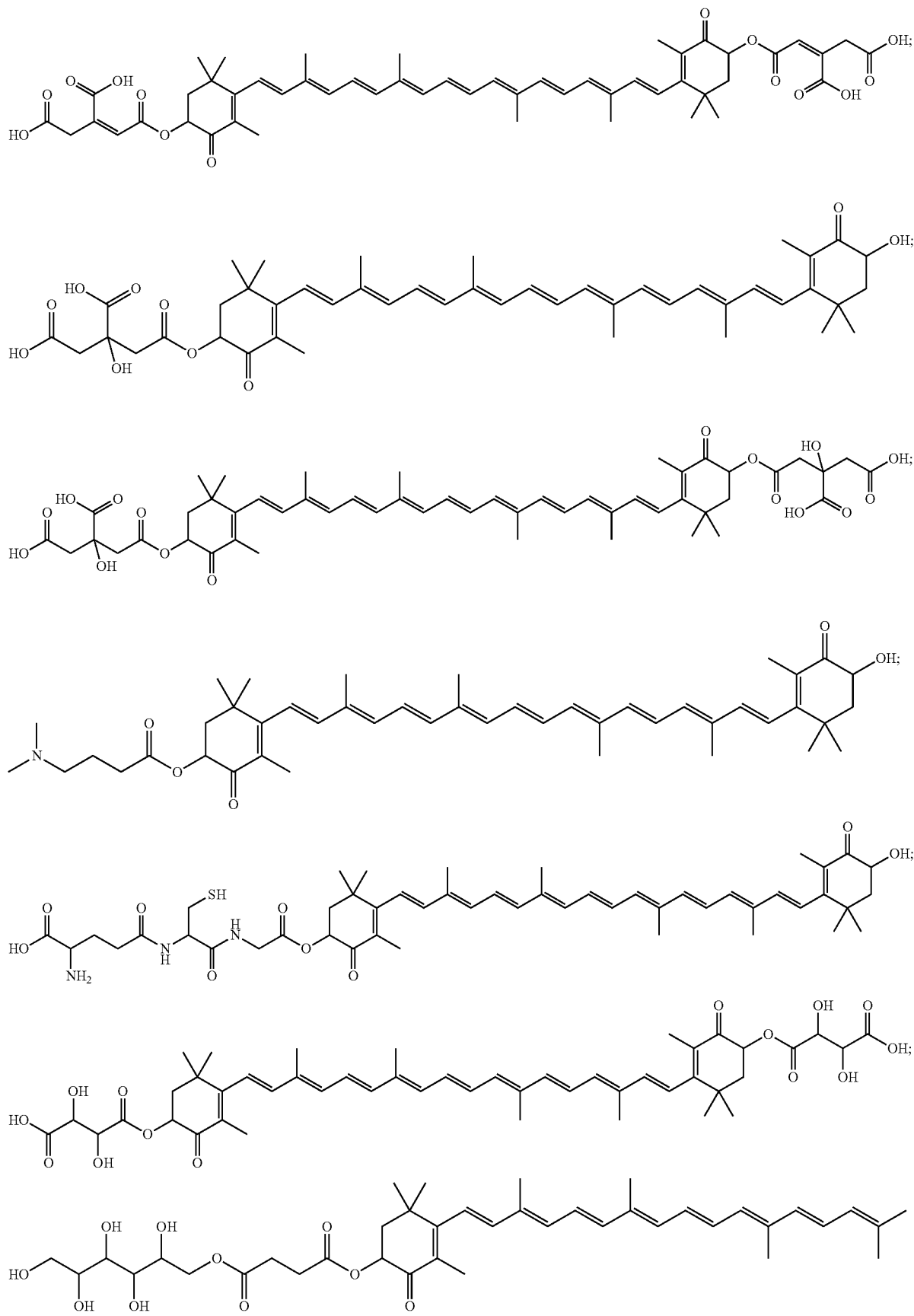

63 64
-continued
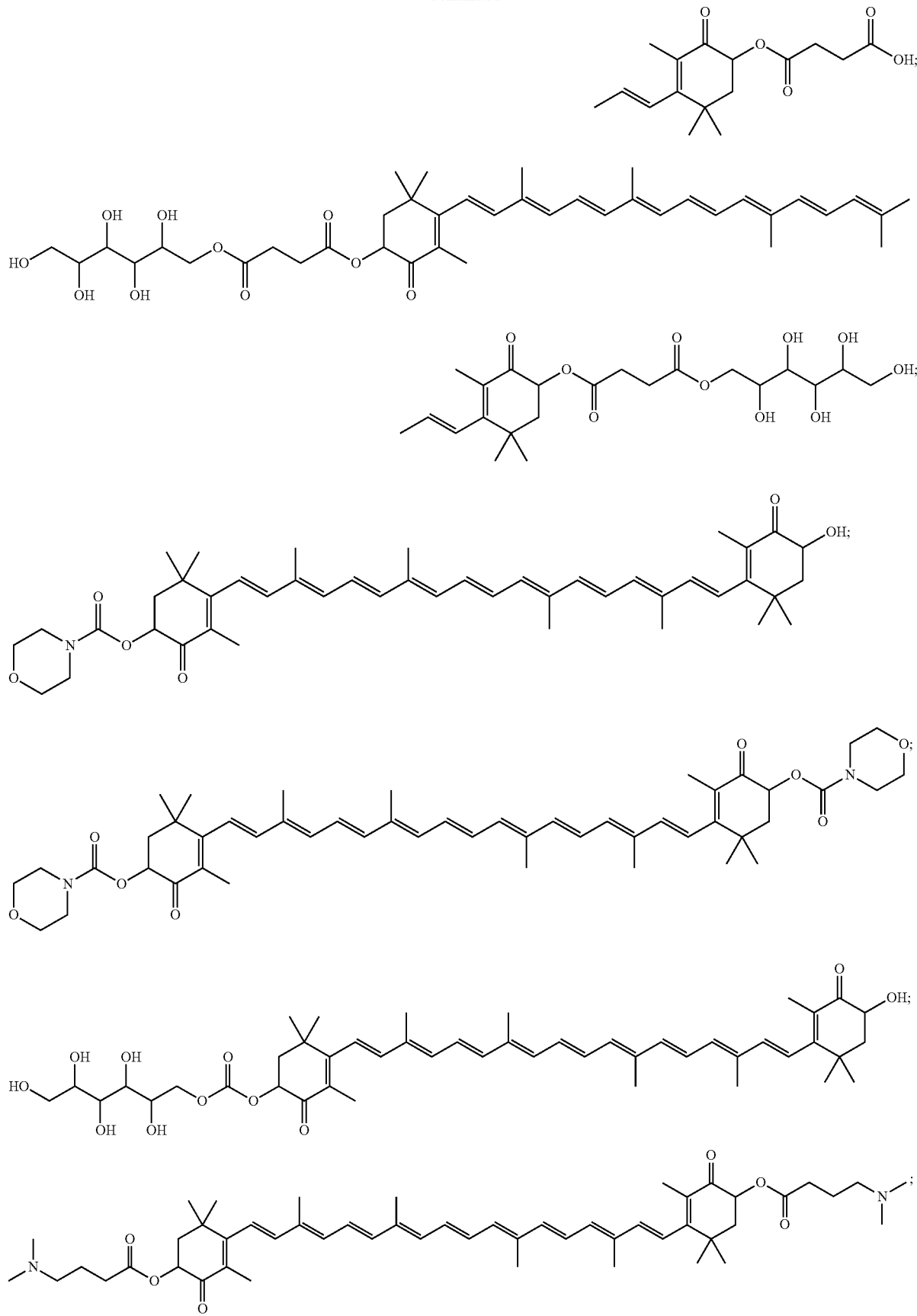

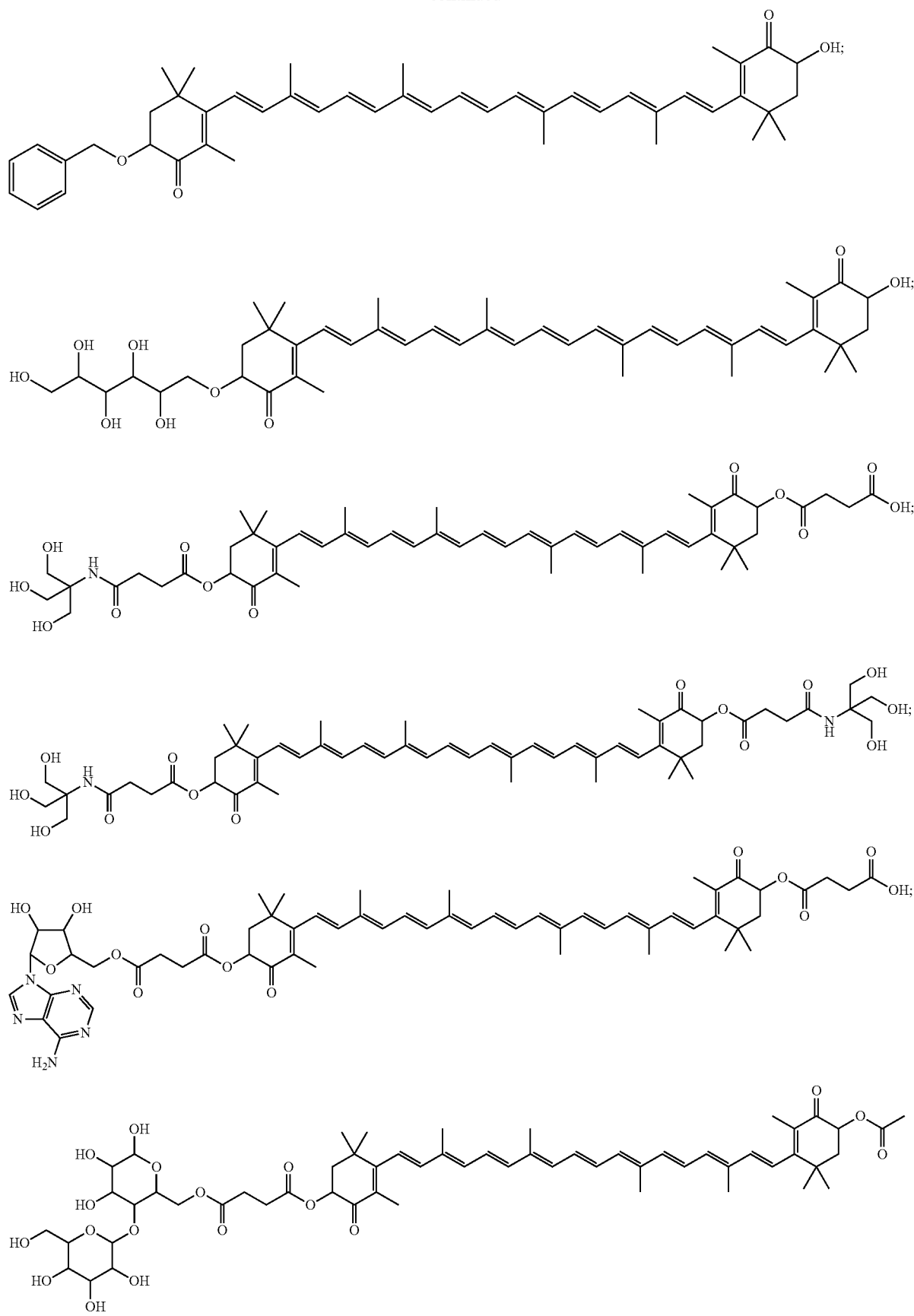

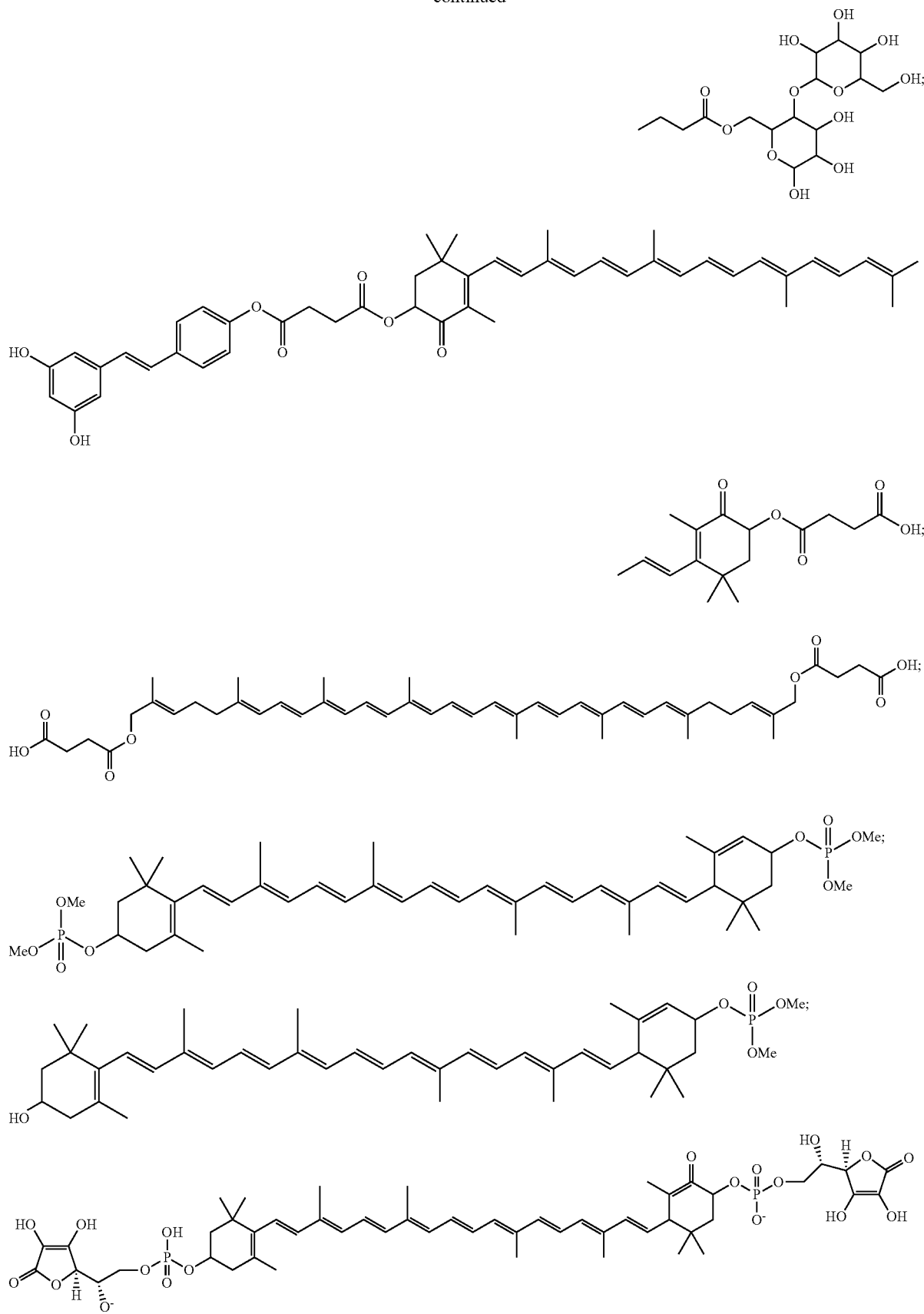

and/or

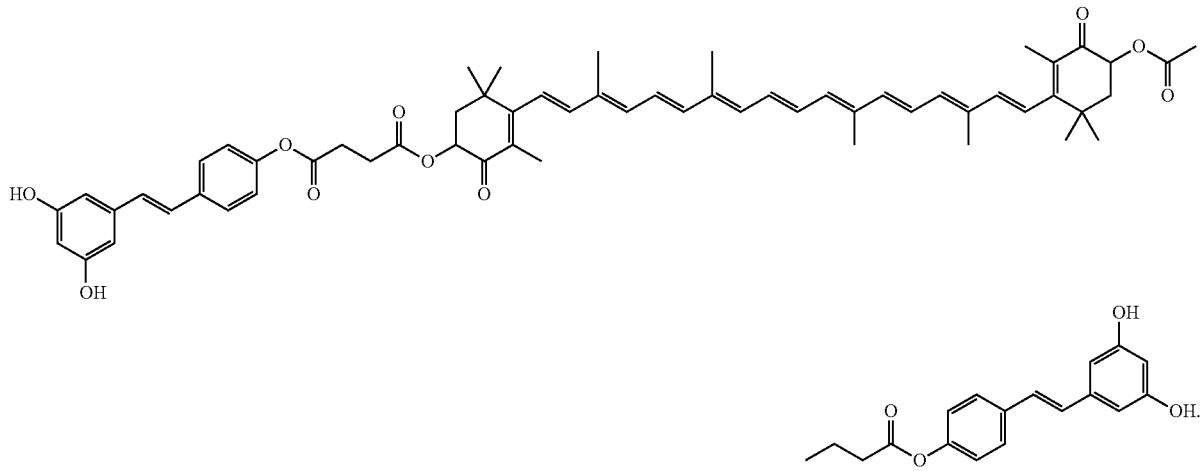

In some embodiments, a chemical compound may include a disuccinic acid ester carotenoid derivative having the structure (160) may be parenterally administered, upon which the spontaneous self-assembly is overcome by interactions with serum and/or tissue components in vivo.

(160)

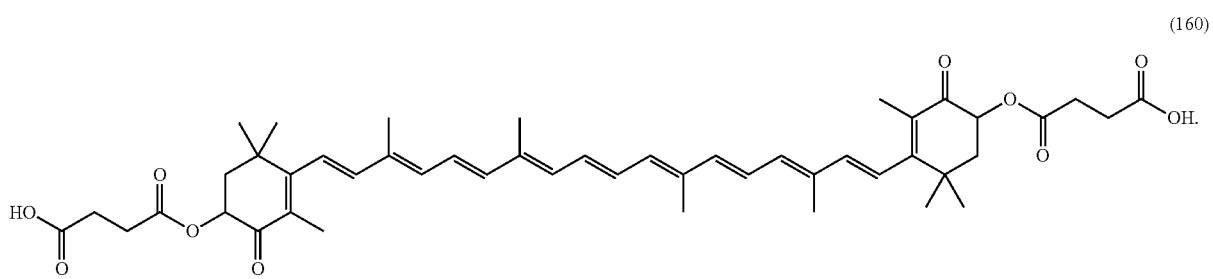 [SMILES: CC1=C(/C=C/C(C)=C/C=C/C(C)=C/C=C/C=C(C)/C=C/C=C(C)/C=C/C2=C(C)C(=O)C(OC(=O)CCC(=O)O)CC2(C)C)C(C)(C)CC(OC(=O)CCC(=O)O)C1=O]

In some embodiments, a chemical compound may include a disodium salt disuccinic acid ester carotenoid derivative having the structure (162)

Some specific embodiments may include phosphate, succinate, co-antioxidant (e.g., Vitamin C, Vitamin C analogs, Vitamin C derivatives, Vitamin E, Vitamin E analogs, Vitamin (162)

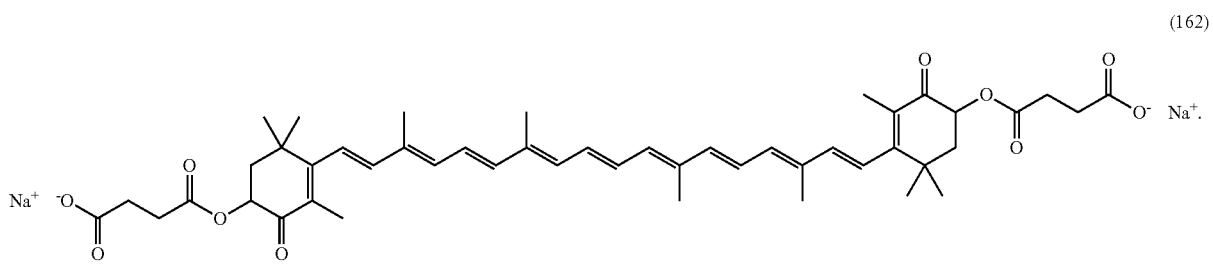

Compounds described herein embrace isomers mixtures, racemic, optically active, and optically inactive stereoisomers and compounds. Carotenoid analogs or derivatives may have increased water solubility and/or water dispersibility relative to some or all known naturally occurring carotenoids. In some embodiments, one or more co-antioxidants may be coupled to a carotenoid or carotenoid derivative or analog.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations E derivatives, or flavonoids), or combinations thereof derivatives or analogs of carotenoids. Flavonoids may include, for example, quercetin, xanthohumol, isoxanthohumol, or genistein. Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

The synthesis of water-soluble and/or water-dispersible carotenoids (e.g., C40) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g. cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. The net overall effect is an improvement in potential clinical utility for the lipophilic carotenoid compounds as therapeutic agents.

In some embodiments, the principles of retrometabolic drug design may be utilized to produce novel soft drugs from the asymmetric parent carotenoid scaffold (e.g., RRR-lutein (β,ε-carotene-3,3'-diol)). For example, lutein scaffold for derivatization was obtained commercially as purified natural plant source material, and was primarily the RRR-stereoisomer (one of 8 potential stereoisomers). Lutein (Scheme 1) possesses key characteristics—similar to starting material astaxanthin—which make it an ideal starting platform for retrometabolic syntheses: (1) synthetic handles (hydroxyl groups) for conjugation, and (2) an excellent safety profile for the parent compound.

In some embodiments, carotenoid analogs or derivatives may have increased water solubility and/or water dispersibility relative to some or all known naturally occurring carotenoids.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, the carotenoid derivatives or analogs may be synthesized from naturally-occurring carotenoids. In some embodiments, the carotenoid derivatives may be synthesized from any naturally-occurring carotenoid including one or more alcohol substituents. In other embodiments, the carotenoid derivatives may be synthesized from a derivative of a naturally-occurring carotenoid including one or more alcohol substituents. The synthesis may result in a single stereoisomer. The synthesis may result in a single geometric isomer of the carotenoid derivative. The synthesis/synthetic sequence may include any prior purification or isolation steps carried out on the parent carotenoid.

In some embodiments, a synthesis may be a total synthesis using methods described herein to synthesize carotenoid derivatives and/or analogs. An example may include, but is not limited to, a 3S,3'S all-E carotenoid derivative, where the parent carotenoid is astaxanthin. The synthetic sequence may include protecting and subsequently deprotecting various functionalities of the carotenoid and/or substituent precursor. When derivates or analogs are prepared from alcohol functionalized carotenoids, a base catalyzed reaction may be used to react the alcohol functional groups with the substituent precursor. Substituent precursors include precursors that include a functional group that may act as a leaving group for a substitution reaction. The base may include any non-nucleophilic base known to one skilled in the art such as, for example, tertiary amines, pyridine, pyrrolidine, etc. The alcohol may act as a nucleophile reacting with the substituent precursor, displacing the leaving group. Leaving groups may include, but are not limited to, I, Cl, Br, tosyl, brosyl, mesyl, or trifyl. These are only a few examples of leaving groups that may be used, many more are known and would be apparent to one skilled in the art. In some embodiments, a base may be used to deprotonate the alcohol. For example, reaction with alkyl lithium bases, alkali metal hydroxide, or alkali metal alcohol salts may deprotonate a hydroxy group of the carotenoid. In other examples the leaving group may be internal and may subsequently be included in the final structure of the carotenoid derivative, a non-limiting example may include anhydrides or strained cyclic ethers. For example, the alcohol may be reacted with succinic anhydride.

In an embodiment, the disuccinic acid ester of astaxanthin may be further converted to the disodium salt. Examples of synthetic sequences for the preparation of some of the specific embodiments depicted are described in the Examples section. The example depicted below is a generic non-limiting example of a synthetic sequence for the preparation of astaxanthin carotenoid derivatives.

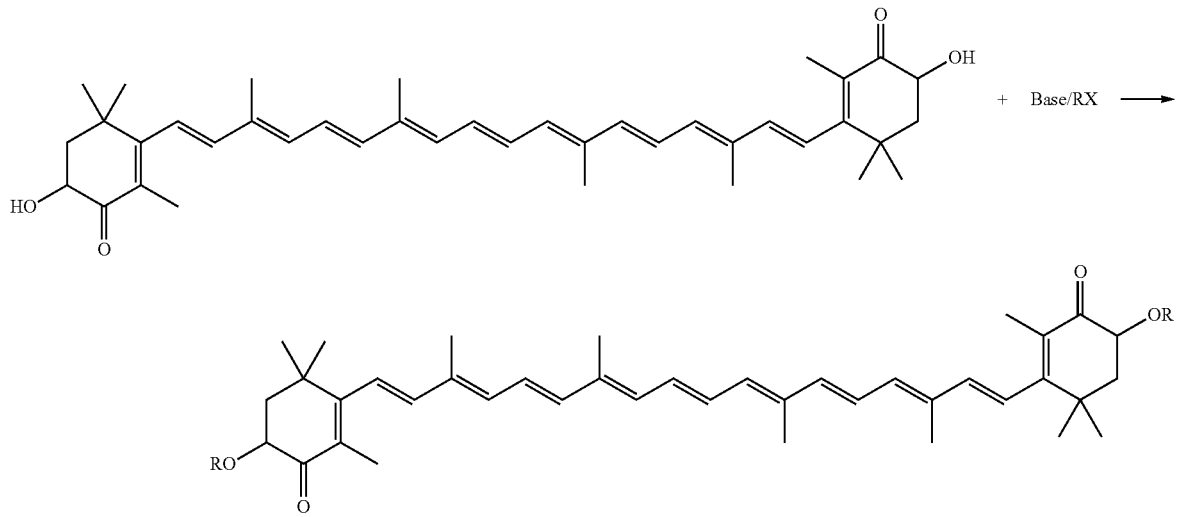

In some embodiments, one or more of the conversions and/or reactions discussed herein may be carried out within one reaction vessel increasing the overall efficiency of the synthesis of the final product. In some embodiments, a product of one reaction during a total synthesis may not be fully worked up before continuing on with the following reaction. In general, fully working up a reaction implies completely isolating and purify the product from a reaction. A reaction may instead only partially be worked up. For example, solid impurities which fall out of solution during the course of a reaction may be filtered off and the filtrate washed with solvent to ensure all of the resulting product is washed through and collected. In such a case the resulting collected product still in solution may not be isolated, but may then be combined with another reagent and further transformed. In some cases multiple transformations may be carried out in a single reaction flask simply by adding reagents one at a time without working up intermediate products. These types of "shortcuts" will improve the overall efficiency of a synthesis, especially when dealing with larger quantity reactions (e.g., along the lines of pilot plant scale and/or plant scale).

In some embodiments, an alcohol-functionalized carotenoid may provide a skeleton with a useful handle with which to appropriately derivatize a carotenoid based water dispersible end product. The example depicted above is a generic nonlimiting example; examples depicted in Schemes 1 and 2 provide more specific examples of the synthesis of water-soluble and/or water-dispersible carotenoid analogs or derivatives. Schemes 1 and 2 depict the syntheses of two water-dispersible lutein derivatives, the sodium salts of lutein disuccinate and lutein diphosphate. Derivatizing hydrophobic carotenoids may impart water-dispersibility.

Scheme 1.

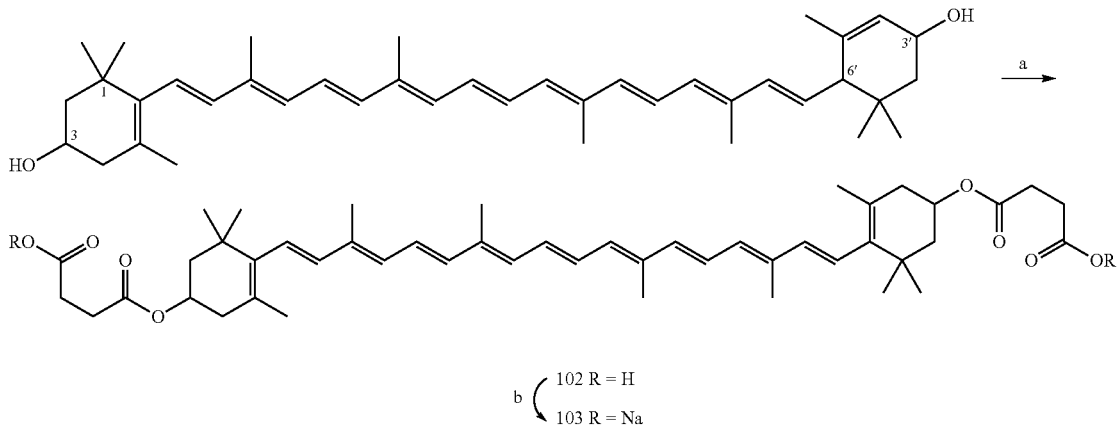

a. succinic anhydride, N,N-diisopropylethylamine, $CH_2Cl_2$ (64%); b. NaOMe, $CH_2Cl_2$/MeOH (5/1) (91%).

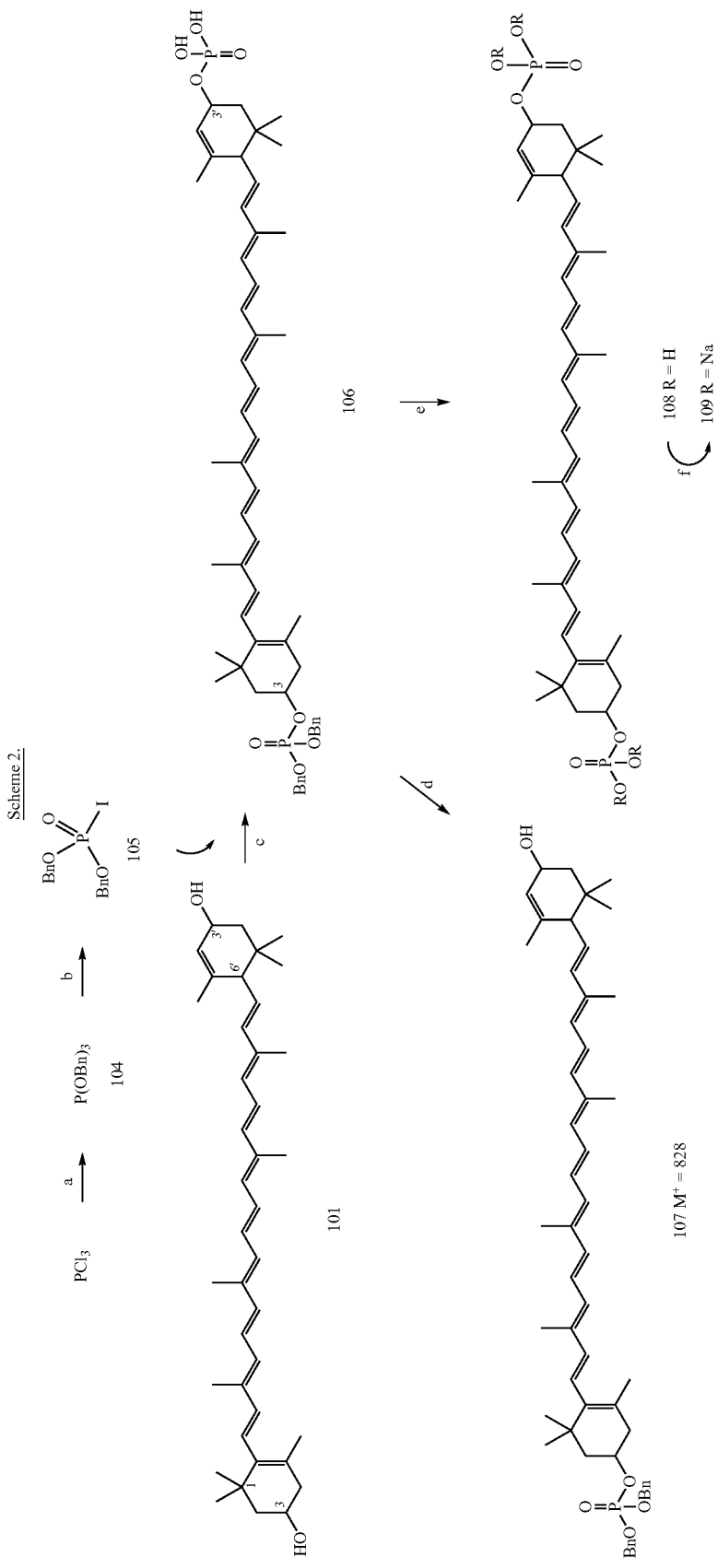

As seen in Scheme 1, the synthesis of disuccinate salt 103 began with succinylation of natural source lutein using succinic anhydride and Hünig base (N,N'-diisopropylethylamine). Reactions may be run in polar organic solvents. Disuccinylation of lutein was optimized by running the reaction in a concentrated fashion and using modest excesses of anhydride and base. Using high concentrations of reagents may allow easier extraction of impurities and side products once the reaction is complete. Aqueous acidic workup yielded disuccinate 102, such that excess reagents and reaction byproducts were removed by copiously extracting the organic layer with dilute HCl. The resulting viscous, red-orange oil was washed or slurried with hexanes to remove non-polar impurities. A successfully functionalized carotenoid may be transformed into an ionic salt derivative or analog in order to increase the water solubility. A carotenoid may be transformed into an ionic salt derivative or analog by reacting the carotenoid with a base. Bases may include alkali metal hydroxides (e.g., sodium hydroxide) or tertiary amines (e.g., triethylamine). In some embodiments, bases, upon deprotonation of one or more moieties of the carotenoid may result in by products which are easily removed (e.g., removed under reduced pressure, extracted). The water-dispersible derivative 103 was generated by treating compound 102 with methanolic sodium methoxide. The reaction was quenched with water and the resulting red-orange aqueous layer was first extracted with $Et_2O$, then lyophilized to provide the sodium salt in good yield.

In some embodiments, a carotenoid may be phosphorylated to increase water solubility and/or dispersibility. In some embodiments, a carotenoid may be diphosphorylated to increase water solubility and/or dispersibility. Successful diphosphorylation of lutein may be achieved using dimethyl phosphoroiodidate. Dimethyl phosphoroiodidate may be formed in situ. Dimethyl phosphoroiodidate may be formed by reacting commercially available trimethyl phosphite with iodine. In some embodiments, a certain degree of success in removing all four diphosphate methyl groups may be realized when using bromotrimethylsilane in the presence of N,O-bis(trimethylsilyl)acetamide. However, this deprotection protocol may not be optimal in that methyl group dealkylation was usually accompanied by the significant decomposition of lutein phosphate.

In some embodiments, a three-step method to provide the tetra-sodium salt of lutein diphosphate 109 may be achieved using benzyl esters as protecting groups for the lutein phosphoric acids (Scheme 2). Lutein (e.g., natural source) may be phosphorylated using dibenzyl phosphoroiodidate. Dibenzyl phosphoroiodidate may be formed in situ. Dibenzyl phosphoroiodidate may be formed by reacting tribenzyl phosphite with iodine. As seen in Scheme 2, tribenzyl phosphite may be prepared by the addition of benzyl alcohol to phosphorus trichloride in the presence of triethylamine. In some embodiments, silica gel chromatography of the crude reaction mixture may yield tribenzyl phosphite in good yield. Compound 106 was formed by treating lutein with freshly prepared dibenzyl phosphoroiodidate in the presence of pyridine. Aqueous workup of the reaction followed by the removal of pyridine by azeotropic distillation using toluene may provide a crude red oil. Contaminations, excess reagents, and reaction byproducts may be removed during work up of the reaction or at a later time (e.g., after a subsequent reaction). Non-polar impurities may be removed from the crude product mixture by alternately washing or slurrying with hexanes and $Et_2O$ to give 106.

In some embodiments, dealkylation of one or more of the four benzyl esters of the phosphoric acid moieties may occur during the phosphorylation reaction. Dealkylation may occur at the more sensitive allylic 3' phosphate positions. As seen in Scheme 2, the attempted removal of the phosphoric acid benzyl esters of 106 using $LiOH-H_2O$ may result in the generation of a less polar product versus compound 106, exhibiting a molecular ion of 828 as noted by LC/MS analysis. Under these reaction conditions, dephosphorylation at one of the two hydroxyls of the lutein derivative may occur rather than the desired debenzylation to give compound 107. Such data indirectly support compound 106's structure and thus the occurrence of bis-dealkylation at one phosphate versus mono-dealkylation at both phosphates as an additional result of the phosphorylation of lutein. If mono-dealkylation at both phosphates occurred during phosphorylation, then treatment of the resulting product with $LiOH-H_2O$ would have produced a lutein derivative possessing one phosphoric acid containing only one benzyl ester, exhibiting a molecular ion of 738 upon LC/MS analysis.

In some embodiments, successful dealkylation of the phosphate protecting groups of 106 may be achieved using bromotrimethylsilane in the presence of N,O-bis(trimethylsilyl) acetamide (see Scheme 2). A significant amount of excess reagents and reaction byproducts may be removed from the resulting red oil by alternately washing or slurrying the crude mixture with ethyl acetate and $CH_2Cl_2$ to provide diphosphate 108 as an orange oil.

In some embodiments, the sodium salt of lutein diphosphate (109) may be generated by treating 108 with methanolic sodium methoxide (see Scheme 2). The resulting crude orange solid may be washed or slurried with methanol and then dissolved in water. The aqueous layer may be extracted first with $CH_2Cl_2$, then with ethyl acetate, and again with $CH_2Cl_2$. Lyophilization of the red-orange aqueous solution may give the sodium salt as an orange, hygroscopic solid. The phosphorylation process may provide the desired water-dispersible lutein derivative 109 in good yield over the three steps.

The synthetic preparation of carotenoid derivatives or analogs such as disodium disuccinate astaxanthin 162 at multi-gram scale (e.g., 200 g to 1 kg) is necessary if one wishes to produce these molecules commercially. Synthetic modifications of carotenoids, with the goal of increasing aqueous solubility and/or dispersibility, have been sparingly reported in the literature. At the time process development began, surveys of the peer-reviewed and patent literature indicated that neither a synthetic sequence nor an efficient process for the synthesis of 160 or 162 had been reported. Therefore, the bench-scale synthetic sequence and later the scale-up to multigram scale were optimized to improve both the yield and purity of the desired compound. Examples of synthetic preparation of carotenoids and carotenoid derivatives or analogs are illustrated in U.S. Patent Application Ser. No. 60/615,032 filed on Oct. 1, 2004, entitled "METHODS FOR SYNTHESIS OF CAROTENOIDS, INCLUDING ANALOGS, DERIVATIVES, AND SYNTHETIC AND BIOLOGICAL INTERMEDIATES" to Lockwood et al. which is incorporated by reference as if fully set forth herein.

The disodium disuccinate derivatives of synthetic astaxanthin were successfully synthesized in gram amounts and at high purity (>90%) area under the curve (AUC) by HPLC. The compound in "racemic" form demonstrated water "dispersibility" of 8.64 mg/mL, a significant improvement over the parent compound astaxanthin, which is insoluble in water. Initial biophysical characterization demonstrated that Cardax™ derivatives (as both the statistical mixture of stereoisomers and as individual stereoisomers) were potent direct scavengers of superoxide anion in the aqueous phase, the first such description in this model system for a C40 carotenoid. Plasma-protein binding studies in vitro revealed that the meso-(3R,3S)-disodium disuccinate astaxanthin derivative bound immediately and preferentially to human serum albumin (HSA) at a binding site, suggesting that beneficial ligand-binding associations might take place in vivo after parenteral administration of the compound. The single- and multiple-dose pharmacokinetics of an oral preparation of the racemic compound (in lipophilic emulsion) were then investigated in a murine model, and significant plasma and tissue levels of nonesterified astaxanthin were achieved. Proof-of-concept studies in ischemia-reperfusion injury performed in rodents subsequently revealed that intravenous pretreatment with Cardax™ was significantly cardioprotective and achieved myocardial salvage in this experimental infarction model (e.g., up to 56% at the highest dose tested). The test material for three of the studies described above was obtained from a single pilot batch of compound (>200 g single batch at >97% purity by HPLC).

In some embodiments, it may be advantageous to be able to efficiently separate out individual stereoisomers of a racemic mixture of a chemical compound. Efficiently separating out individual stereoisomers on a relatively large scale may advantageously increase availability of starting materials.

In some embodiments, chromatographic separation techniques may be used to separate stereoisomers of a racemic mixture. In some embodiments pure optically active stereoisomers may be reacted with a mixture of stereoisomers of a chemical compound to form a mixture of diastereomers. Diastereomers may have different physical properties as opposed to stereoisomers, thus making it easier to separate diastereomers.

For example it may be advantageous to separate out stereoisomers from a racemic mixture of astaxanthin. In some embodiments, astaxanthin may be coupled to an optically active compound (e.g., dicamphanic acid). Coupling astaxanthin to optically active compounds produces diastereomers with different physical properties. The diastereomers produced may be separated using chromatographic separation techniques as described herein.

Bulk chromatographic separation of the diastereomeric dicamphanic acid ester(s) of synthetic astaxanthin at preparative chromatography scale was performed to subsequently make gram-scale quantities of each stereoisomer of disodium disuccinate ester astaxanthin.

As used herein the terms "structural carotenoid analogs or derivatives" may be generally defined as carotenoids and the biologically active structural analogs or derivatives thereof "Derivative" in the context of this application is generally defined as a chemical substance derived from another substance either directly or by modification or partial substitution. "Analog" in the context of this application is generally defined as a compound that resembles another in structure but is not necessarily an isomer. Typical analogs or derivatives include molecules which demonstrate equivalent or improved biologically useful and relevant function, but which differ structurally from the parent compounds. Parent carotenoids are selected from the more than 700 naturally occurring carotenoids described in the literature, and their stereo- and geometric isomers. Such analogs or derivatives may include, but are not limited to, esters, ethers, carbonates, amides, carbamates, phosphate esters and ethers, sulfates, glycoside ethers, with or without spacers (linkers).

As used herein the terms "the synergistic combination of more than one structural analog or derivative or synthetic intermediate of carotenoids" may be generally defined as any composition including one structural carotenoid analog or derivative or synthetic intermediate combined with one or more other structural carotenoid analogs or derivatives or synthetic intermediate or co-antioxidants, either as derivatives or in solutions and/or formulations.

As used herein the terms "subject" may be generally defined as all mammals, in particular humans.

As used herein the terms "administration" may be generally defined as the administration of the pharmaceutical or over-the-counter (OTC) or nutraceutical compositions by any means that achieves the intended purpose. For example, administration may include parenteral, subcutaneous, intravenous, intracoronary, rectal, intramuscular, intra-peritoneal, transdermal, or buccal routes. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired.

In some embodiments, techniques described herein may be applied to the inhibition and/or amelioration of any disease or disease state related to reactive oxygen species ("ROS") and other radical and non-radical species.

In some embodiments, techniques described herein may be applied to the inhibition and/or amelioration of inflammation, including but not limited to ischemic reperfusion injury of a tissue.

An embodiment may include the administration of structural carotenoid analogs or derivatives or synthetic intermediates alone or in combination to a subject such that the occurrence of inflammation is thereby inhibited and/or ameliorated. The structural carotenoid analogs or derivatives or synthetic intermediates may be water-soluble and/or water dispersible derivatives. The carotenoid derivatives may include any substituent that substantially increases the water solubility of the naturally occurring carotenoid. The carotenoid derivatives may retain and/or improve the antioxidant properties of the parent carotenoid. The carotenoid derivatives may retain the non-toxic properties of the parent carotenoid. The carotenoid derivatives may have increased bioavailability, relative to the parent carotenoid, upon administration to a subject. The parent carotenoid may be naturally occurring.

Another embodiments may include the administration of a composition comprised of the synergistic combination of more than one structural analog or derivative or synthetic intermediate of carotenoids to a subject such that the occurrence of tissue damage associated with an inflammatory response is thereby reduced. The composition may be a "racemic" (i.e. mixture of the potential stereoisomeric forms) mixture of carotenoid derivatives. Included as well are pharmaceutical compositions comprised of structural analogs or derivatives or synthetic intermediates of carotenoids in combination with a pharmaceutically acceptable carrier. In one embodiment, a pharmaceutically acceptable carrier may be serum albumin. In one embodiment, structural analogs or derivatives or synthetic intermediates of carotenoids may be complexed with human serum albumin (i.e., HSA) in a solvent. HSA may act as a pharmaceutically acceptable carrier.

In some embodiments, a single stereoisomer of a structural analog or derivative or synthetic intermediate of carotenoids may be administered to a human subject in order to ameliorate a pathological condition. Administering a single stereoisomer of a particular compound (e.g., as part of a pharmaceutical composition) to a human subject may be advantageous (e.g., increasing the potency of the pharmaceutical composition). Administering a single stereoisomer may be advantageous due to the fact that only one isomer of potentially many may be biologically active enough to have the desired effect.

In some embodiments, compounds described herein may be administered in the form of nutraceuticals. "Nutraceuticals" as used herein, generally refers to dietary supplements, foods, or medical foods that: 1. possess health benefits generally defined as reducing the risk of a disease or health condition, including the management of a disease or health condition or the improvement of health; and 2. are safe for human consumption in such quantity, and with such frequency, as required to realize such properties. Generally a nutraceutical is any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It is important to note that this definition applies to all categories of food and parts of food, ranging from dietary supplements such as folic acid, used for the prevention of spina bifida, to chicken soup, taken to lessen the discomfort of the common cold. This definition also includes a bio-engineered designer vegetable food, rich in antioxidant ingredients, and a stimulant functional food or pharmafood. Within the context of the description herein where the composition, use and/or delivery of pharmaceuticals are described nutraceuticals may also be composed, used, and/or delivered in a similar manner where appropriate.

In some embodiments, compositions may include all compositions of 1.0 gram or less of a particular structural carotenoid analog, in combination with 1.0 gram or less of one or more other structural carotenoid analogs or derivatives or synthetic intermediates and/or co-antioxidants, in an amount which is effective to achieve its intended purpose. While individual subject needs vary, determination of optimal ranges of effective amounts of each component is with the skill of the art. Typically, a structural carotenoid analog or derivative or synthetic intermediates may be administered to mammals, in particular humans, orally at a dose of 5 to 100 mg per day referenced to the body weight of the mammal or human being treated for a particular disease. Typically, a structural carotenoid analog or derivative or synthetic intermediate may be administered to mammals, in particular humans, parenterally at a dose of between 5 to 1000 mg per day referenced to the body weight of the mammal or human being treated for a particular disease. In other embodiments, about 100 mg of a structural carotenoid analog or derivative or synthetic intermediate is either orally or parenterally administered to treat or prevent disease.

The unit oral dose may comprise from about 0.25 mg to about 1.0 gram, or about 5 to 25 mg, of a structural carotenoid analog. The unit parenteral dose may include from about 25 mg to 1.0 gram, or between 25 mg and 500 mg, of a structural carotenoid analog. The unit intracoronary dose may include from about 25 mg to 1.0 gram, or between 25 mg and 100 mg, of a structural carotenoid analog. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a structural carotenoid analog or derivative or synthetic intermediate as a raw chemical, the compounds may be administered as part of a pharmaceutical preparation containing suitable pharmaceutically acceptable carriers, preservatives, excipients and auxiliaries which facilitate processing of the structural carotenoid analog or derivative or synthetic intermediates which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Soft gelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or soft gelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

EXAMPLES

Having now described the invention, the same will be more readily understood through reference to the following example(s), which are provided by way of illustration, and are not intended to be limiting of the present invention.

General.

Natural source lutein (90%) was obtained from ChemPacific, Inc. (Baltimore, Md.) as a red-orange solid and was used without further purification. All other reagents and solvents used were purchased from Acros (New Jersey, USA) and were used without further purification. All reactions were performed under $N_2$ atmosphere. All flash chromatographic purifications were performed on Natland International Corporation 230-400 mesh silica gel using the indicated solvents. LC/MS (APCI) and LC/MS (ESI) were recorded on an Agilent 1100 LC/MSD VL system; column. Zorbax Eclipse XDB-C18 Rapid Resolution (4.6×75 mm, 3.5 μm, USUT002736); temperature: 25° C.; starting pressure: 105 bar; flow rate: 1.0 mL/min; mobile phase (% A=0.025% trifluoroacetic acid in $H_2O$, % B=0.025% trifluoroacetic acid in acetonitrile) Gradient program: 70% A/30% B (start), step gradient to 50% B over 5 min, step gradient to 98% B over 8.30 min, hold at 98% B over 25.20 min, step gradient to 30% B over 25.40 min; PDA Detector: 470 nm. The presence of trifluoroacetic acid in the LC eluents acts to protonate synthesized lutein disuccinate and diphosphate salts to give the free di-acid forms, yielding $M^+$=768 for the disuccinate salt sample and $M^+$=728 for the diphosphate salt sample in MS analyses. LRMS: + mode; ESI: electrospray chemical ionization, ion collection using quadrapole; APCI: atmospheric pressure chemical ionization, ion collection using quadrapole. MS (ESI-IT) was recorded on a HCT plus Bruker Daltonics Mass Spectrometer system, LRMS: + mode; ESI-IT: electrospray chemical ionization, ion collection using ion trap. $^1$H NMR analyses were attempted on Varian spectrometers (300 and 500 MHz). NMR analyses of natural source lutein as well as synthesized lutein derivatives yielded only partially discernable spectra, perhaps due to the presence of interfering impurities (natural source lutein), or due to aggregation (natural source lutein and derivatives). In attempts to circumvent the problems associated with NMR analyses, samples were prepared using mixtures of deuterated solvents including methanol/chloroform, methanol/water, methyl sulfoxide/water, and chloroform/methanol/water. However, such attempts failed to give useful data.

Natural source lutein (β,ε-carotene-3,3'-diol), 1. LC/MS (ESI): 9.95 min (2.78%), $\lambda_{max}$ 226 nm (17%), 425 nm (100%); 10.58 min (3.03%), $\lambda_{max}$ 225 nm (21%), 400 nm (100%); 11.10 min (4.17%), $\lambda_{max}$ 225 nm (16%), 447 nm (100%); 12.41 min (90.02%), $\lambda_{max}$ 269 nm (14%), 447 nm (100%), m/z 568 $M^+$ (69%), 551 $[M-H_2O+H]^+$ (100%), 533 $[M-2H_2O+H]^+$ (8%)

β,ε-carotenyl 3,3'-disuccinate, 2. To a solution of natural source lutein (1) (0.50 g, 0.879 mmol) in $CH_2Cl_2$ (8 mL) was added N,N-diisopropylethylamine (3.1 mL, 17.58 mmol) and succinic anhydride (0.88 g, 8.79 mmol). The solution was stirred at RT overnight and then diluted with $CH_2Cl_2$ and quenched with water/1 M HCl (5/1). The aqueous layer was extracted two times with $CH_2Cl_2$ and the combined organic layer was washed three times with cold water/1 M HCl (5/1), dried over $Na_2SO_4$, and concentrated. The resulting red-orange oil was washed (slurried) three times with hexanes to yield disuccinate 2 (0.433 g, 64%) as a red-orange solid; LC/MS (APCI): 10.37 min (4.42%), $\lambda_{max}$ 227 nm (56%), 448 nm (100%), m/z 769 $[M+H]^+$ (8%), 668 $[M-C_4O_3H_4]^+$ (9%), 637 (36%), 138 (100%); 11.50 min (92.40%), $\lambda_{max}$ 269 nm (18%), 447 nm (100%), m/z 769 $[M+H]^+$ (7%), 668 $[M-C_4O_3H_4]^+$ (9%), 651 (100%); 12.03 min (3.18%) $\lambda_{max}$ 227 nm (55%), 446 nm (100%), m/z 668 $[M-C_4O_3H_4]^+$ (15%), 550 (10%), 138 (100%)

β,ε-carotenyl 3,3'-disuccinate sodium salt, 3. To a solution of disuccinate 2 (0.32 g, 0.416 mmol) in $CH_2Cl_2$/methanol (5 mL/1 mL) at 0° C. was added drop-wise sodium methoxide (25% wt in methanol; 0.170 mL, 0.748 mmol). The solution was stirred at RT overnight and then quenched with water and stirred for 5 min. The solution was then concentrated and the aqueous layer was washed four times with $Et_2O$. Lyophilization of the clear, red-orange aqueous solution yielded 3 (0.278 g, 91%) as an orange, hygroscopic solid; LC/MS (APCI): 11.71 min (94.29%), $\lambda_{max}$ 269 nm (18%), 446 nm (100%), m/z 769 $[M-2Na+3H]^+$ (8%), 668 $[M-2Na+2H-C_4O_3H_4]^+$ (6%), 651 (100%); 12.74 min (5.71%), $\lambda_{max}$ 227 nm (30%), 269 nm (18%), 332 nm (39%), 444 nm (100%), m/z 768 $[M-2Na+2H]^+$ (2%), 668 $[M-2Na+2H-C_4O_3H_4]^+$ (3%), 651 (12%), 138 (100%)

Tribenzyl phosphite, 4. To a well-stirred solution of phosphorus trichloride (1.7 mL, 19.4 mmol) in $Et_2O$ (430 mL) at 0° C. was added dropwise a solution of triethylamine (8.4 mL, 60.3 mmol) in Et$_2$O (20 mL), followed by a solution of benzyl alcohol (8.1 mL, 77.8 mmol) in Et$_2$O (20 mL). The mixture was stirred at 0° C. for 30 min and then at RT overnight. The mixture was filtered and the filtrate concentrated to give a colorless oil. Silica chromatography (hexanes/Et$_2$O/triethylamine, 4/1/1%) of the crude product yielded 4 (5.68 g, 83%) as a clear, colorless oil that was stored under N$_2$ at −20° C.; $^1$H NMR: δ 7.38 (15H, m), 4.90 (6H, d)

Dibenzyl phosphoroiodidate, 5. To a solution of tribenzyl phosphite (5.43 g, 15.4 mmol) in CH$_2$Cl$_2$ (8 mL) at 0° C. was added I$_2$ (3.76 g, 14.8 mmol). The mixture was stirred at 0° C. for 10 min or until the solution became clear and colorless. The solution was then stirred at RT for 10 min and used directly in the next step.

3-(Bis benzyl-phosphoryloxy)-3'-(phosphoryloxy)-β,ε-carotene, 6. To a solution of natural source lutein (1) (0.842 g, 1.48 mmol) in CH$_2$Cl$_2$ (8 mL) was added pyridine (4.8 mL, 59.2 mmol). The solution was stirred at 0° C. for 5 min and then freshly prepared 5 (14.8 mmol) in CH$_2$Cl$_2$ (8 mL) was added drop-wise to the mixture at 0° C. The solution was stirred at 0° C. for 1 h and then diluted with CH$_2$Cl$_2$ and quenched with brine. The aqueous layer was extracted twice with CH$_2$Cl$_2$ and the combined organic layer was washed once with brine, then dried over Na$_2$SO$_4$ and concentrated. Pyridine was removed from the crude red oil by azeotropic distillation using toluene. The crude product was alternately washed (slurried) twice with hexanes and Et$_2$O to yield 6 as a red oil, used in the next step without further purification; LC/MS (ESI): 9.93 min (44.78%), $\lambda_{max}$ 267 nm (33%), 444 nm (100%), m/z 890 [M−H$_2$O]$^+$ (8%), 811 [M−PO$_3$H—H$_2$O+H]$^+$ (73%), 533 (100%); 9.99 min (29.0%), $\lambda_{max}$ 268 nm (24%), 446 nm (100%), m/z 890 [M−H$_2$O]$^+$ (6%), 811 [M−PO$_3$H−H$_2$O+H]$^+$ (72%), 533 (100%); 10.06 min (26.23%), λmax 266 nm (15%), 332 nm (22%), 444 nm (100%), m/z 890 [M−H$_2$O]$^+$ (5%), 811 [M−PO$_3$H—H$_2$O+H]$^+$ (90%), 533 (100%)

3-(Bis benzyl-phosphoryloxy)-3'-hydroxy-β,ε-carotene, 7. To a solution of 6 (0.033 mmol) in tetrahydrofuran/water (1 mL/0.5 mL) at 0° C. was added LiOH—H$_2$O (0.003 g, 0.073 mmol). The solution was stirred at RT for 1 h and then quenched with methanol. The crude reaction mixture was analyzed by LC/MS; LC/MS (ESI): 10.02 min (40.60%), $\lambda_{max}$ 266 nm (12%), 333 nm (25%), 445 nm (100%), m/z 890 [M−H$_2$O]$^+$ (33%), 811 [M−PO$_3$H—H$_2$O+H]$^+$ (50%), 533 (100%); 16.37 min (49.56%), $\lambda_{max}$ 267 nm (16%), 332 nm (27%), 446 nm (100%), m/z 828 M$^+$ (55%), 550 (44%)

3,3'-Diphosphoryloxy-β,ε-carotene, 8. To a solution of 6 (1.48 mmol) in CH$_2$Cl$_2$ (10 mL) at 0° C. was added drop-wise N,O-bis(trimethylsilyl)acetamide (3.7 mL, 14.8 mmol) and then bromotrimethylsilane (1.56 mL, 11.8 mmol). The solution was stirred at 0° C. for 1 h, quenched with methanol, diluted with CH$_2$Cl$_2$, and then concentrated. The resulting red oil was alternately washed (slurried) three times with ethyl acetate and CH$_2$Cl$_2$ to yield crude phosphate 8 (2.23 g) as a dark orange oil, used in the next step without further purification; LC/MS (ESI): 8.55 min (45.67%), $\lambda_{max}$ 214 nm (25%), 268 nm (28%), 447 nm (100%), m/z 631 [M−PO$_3$H—H$_2$O+H]$^+$ (30%), 533 (18%), 279 (13%), 138 (87%); 8.95 min (35.0%), $\lambda_{max}$ 217 nm (14%), 268 nm (23%), 448 nm (100%), m/z 631 [M−PO$_3$H—H$_2$O+H]$^+$ (26%), 533 (32%), 279 (18%), 138 (100%); 9.41 min (9.70%), $\lambda_{max}$ 225 nm (37%), 269 nm (23%), 335 nm (19%), 447 nm (100%), m/z 631 [M−PO$_3$H—H$_2$O+H]$^+$ (6%), 533 (18%), 279 (13%), 138 (100%) 3,3'-Diphosphoryloxy-β,ε-carotene sodium salt, 9. To a solution of crude 8 (ca 50%; 2.23 g, 3.06 mmol) in methanol (20 mL) at 0° C. was added drop-wise sodium methoxide (25%; 3.5 mL, 15.3 mmol). The solution was stirred at RT for 2 h and the resulting orange solid was washed (slurried) three times with methanol. Water was added to the moist solid and the resulting aqueous layer was extracted with CH$_2$Cl$_2$, ethyl acetate, and again with CH$_2$Cl$_2$. Lyophilization of the clear, red-orange aqueous solution yielded 9 (0.956 g, 80% over 3 steps) as an orange, hygroscopic solid; LC/MS (ESI): 7.81 min (22.34%), $\lambda_{max}$ 215 nm (34%), 268 nm (30%), 448 nm (100%), m/z 711 [M−4Na—H$_2$O+5H]$^+$ (9%), 533 (13%), 306 (100%); 8.33 min (39.56%), $\lambda_{max}$ 217 nm (14%), 268 nm (20%), 448 nm (100%), m/z 711 [M−4Na—H$_2$O+5H]$^+$ (10%), 533 (11%), 306 (100%); 8.90 min (38.09%), $\lambda_{max}$ 223 nm (45%), 269 nm (30%), 336 nm (26%), 448 nm (100%), m/z 711 [M−4Na—H$_2$O+5H]$^+$ (8%), 631 [M−4Na—PO$_3$H—H$_2$O+5H]$^+$ (18%), 533 (20%), 306 (100%); MS (ESI-IT): m/z 816 M$^+$ (55%), 772 [M−2Na+2H]$^+$ (37%), 728 [M−4Na+4H]$^+$ (74%)

UV/Visible Spectroscopy.

Figure 5:
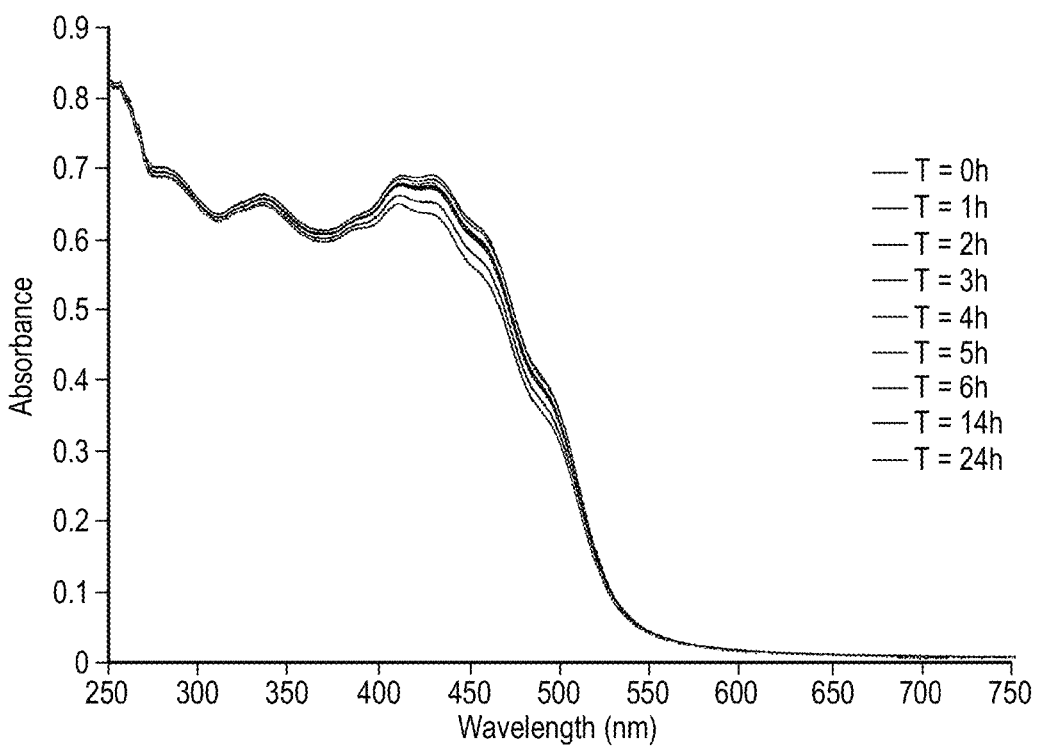
FIG. 5 depicts a time series of the UV/Vis absorption spectra of the disodium diphosphate derivative of natural source lutein in water.
Figure 6:
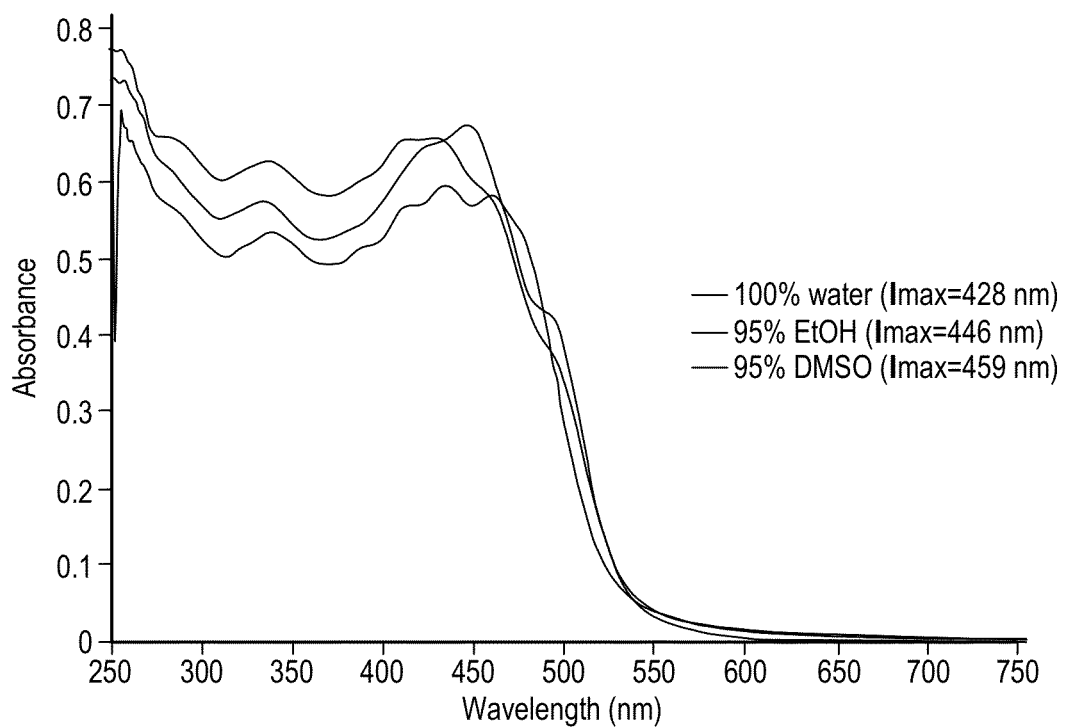
FIG. 6 depicts a UV/Vis absorption spectra of the disodium diphosphate derivative of natural source lutein in 95% ethanol ($\lambda_{max}$=446 nm), 95% DMSO ($\lambda_{max}$=459 nm), and water ($\lambda_{max}$=428 nm).
Figure 7:
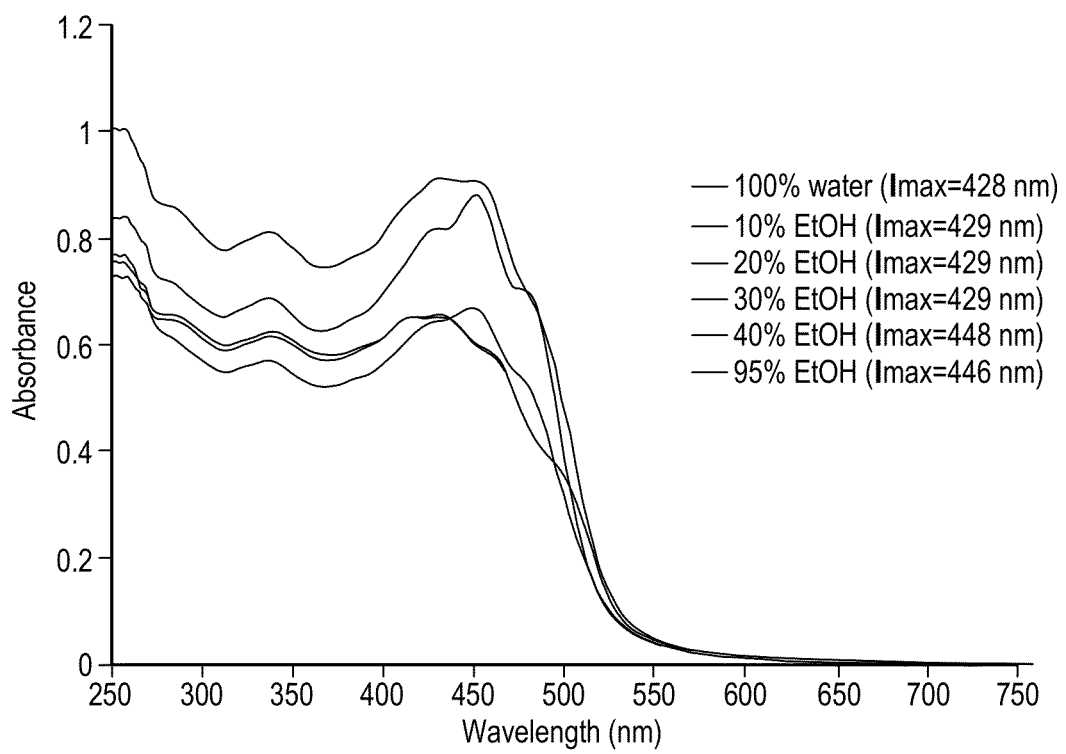
FIG. 7 depicts a UV/Vis absorption spectra of the disodium diphosphate derivative of natural source lutein in water ($\lambda_{max}$=428 nm) with increasing concentrations of ethanol.

For spectroscopic sample preparations, 3 and 9 were dissolved in the appropriate solvent to yield final concentrations of approximately 0.01 mM and 0.2 mM, respectively. The solutions were then added to a rectangular cuvette with 1 cm path length fitted with a glass stopper. The absorption spectrum was subsequently registered between 250 and 750 nm. All spectra were accumulated one time with a bandwidth of 1.0 nm at a scan speed of 370 nm/min. For the aggregation time-series measurements, spectra were obtained at baseline (immediately after solvation; time zero) and then at the same intervals up to and including 24 hours post-solvation (see FIG. 2-FIG. 7). Concentration was held constant in the ethanolic titration of the diphosphate lutein sodium salt, for which evidence of card-pack aggregation was obtained (FIG. 5-FIG. 7).

Determination of Aqueous Solubility/Dispersibility.

30.13 mg of 3 was added to 1 mL of USP-purified water. The sample was rotated for 2 hours, then centrifuged for 5 minutes. After centrifuging, solid was visible in the bottom of the tube. A 125-µL aliquot of the solution was then diluted to 25 mL. The sample was analyzed by UV/Vis spectroscopy at 436 nm, and the absorbance was compared to a standard curve compiled from 4 standards of known concentration. The concentration of the original supernatant was calculated to be 2.85 mg/mL and the absorptivity was 36.94 AU*mL/cm*mg. Slight error may have been introduced by the small size of the original aliquot.

Next, 30.80 mg of 9 was added to 1 mL of USP-purified water. The sample was rotated for 2 hours, then centrifuged for 5 minutes. After centrifuging, solid was visible in the bottom of the tube. A 125-µL aliquot of the solution was then diluted to 25 mL. The sample was analyzed by UV/Vis spectroscopy at 411 nm, and the absorbance was compared to a standard curve compiled from 4 standards of known concentration. The concentration of the original supernatant was calculated to be 29.27 mg/mL and the absorptivity was 2.90 AU*mL/cm*mg. Slight error may have been introduced by the small size of the original aliquot.

Leukocyte Isolation and Preparation.

Human polymorphonuclear leukocytes (PMNs) were isolated from freshly sampled venous blood of a single volunteer (S.F.L.) by Percoll density gradient centrifugation as described previously. Briefly, each 10 mL of whole blood was mixed with 0.8 mL of 0.1 M EDTA and 25 mL of saline. The diluted blood was then layered over 9 mL of Percoll at a specific density of 1.080 g/mL. After centrifugation at 400×g for 20 min at 20° C., the plasma, mononuclear cell, and Percoll layers were removed. Erythrocytes were subsequently lysed by addition of 18 mL of ice-cold water for 30 s, followed by 2 mL of 10×PIPES buffer (25 mM PIPES, 110 mM NaCl, and 5 mM KCl, titrated to pH 7.4 with NaOH). Cells were then pelleted at 4° C., the supernatant was decanted, and the procedure was repeated. After the second hypotonic cell lysis, cells were washed twice with PAG buffer [PIPES buffer containing 0.003% human serum albumin (HSA) and 0.1% glucose]. Afterward, PMNs were counted by light microscopy on a hemocytometer. The isolation yielded PMNs with a purity of >95%. The final pellet was then suspended in PAG-CM buffer (PAG buffer with 1 mM $CaCl_2$ and 1 mM $MgCl_2$). EPR Measurements. All EPR measurements were performed using a Bruker ER 300 EPR spectrometer operating at X-band with a $TM_{110}$ cavity as previously described. The microwave frequency was measured with a Model 575 microwave counter (EIP Microwave, Inc., San Jose, Calif.). To measure superoxide anion ($O^T_2$) generation from phorbol-ester (PMA)-stimulated PMNs, EPR spin-trapping studies were performed using the spin trap DEPMPO (Oxis, Portland, Oreg.) at 10 mM. $1\times10^6$ PMNs were stimulated with PMA (1 ng/mL) and loaded into capillary tubes for EPR measurements. To determine the radical scavenging ability of 3 and 9 in aqueous and ethanolic formulations, PMNs were pre-incubated for 5 minutes with test compound, followed by PMA stimulation.

Instrument settings used in the spin-trapping experiments were as follows: modulation amplitude, 0.32 G; time constant, 0.16 s; scan time, 60 s; modulation frequency, 100 kHz; microwave power, 20 milliwatts; and microwave frequency, 9.76 GHz. The samples were placed in a quartz EPR flat cell, and spectra were recorded. The component signals in the spectra were identified and quantified as reported previously. UV/Vis Spectral Properties in Organic and Aqueous Solvents.

Figure 2:
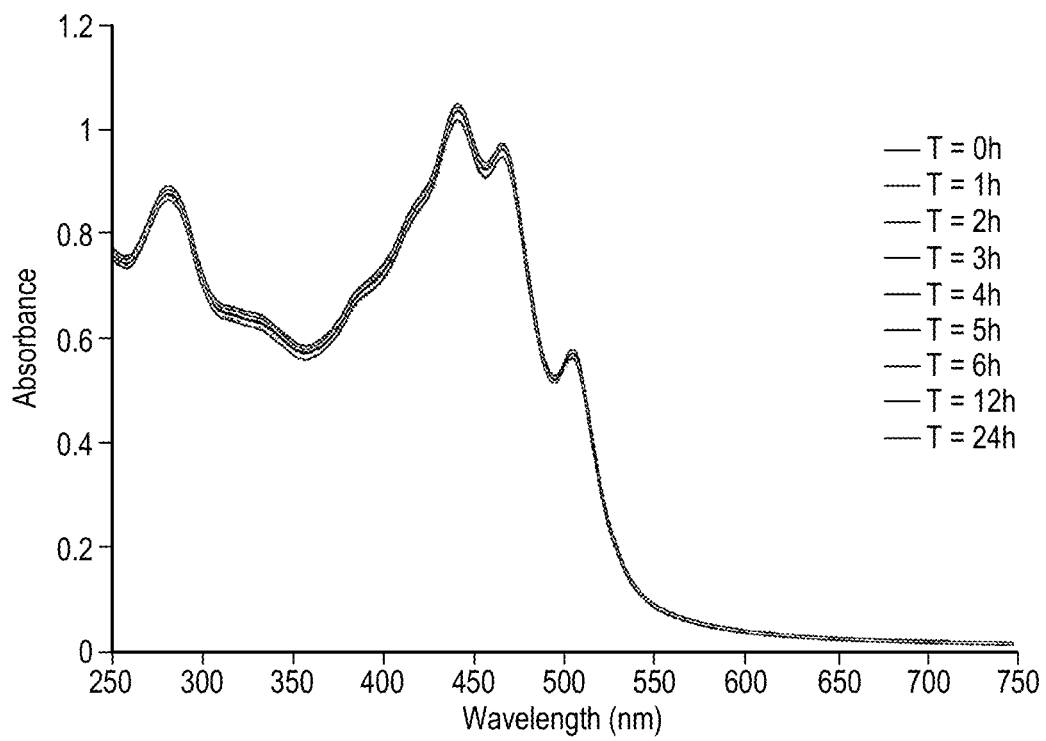
FIG. 2 depicts a time series of the UV/Vis absorption spectra of the disodium disuccinate derivative of natural source lutein in water.
Figure 3:
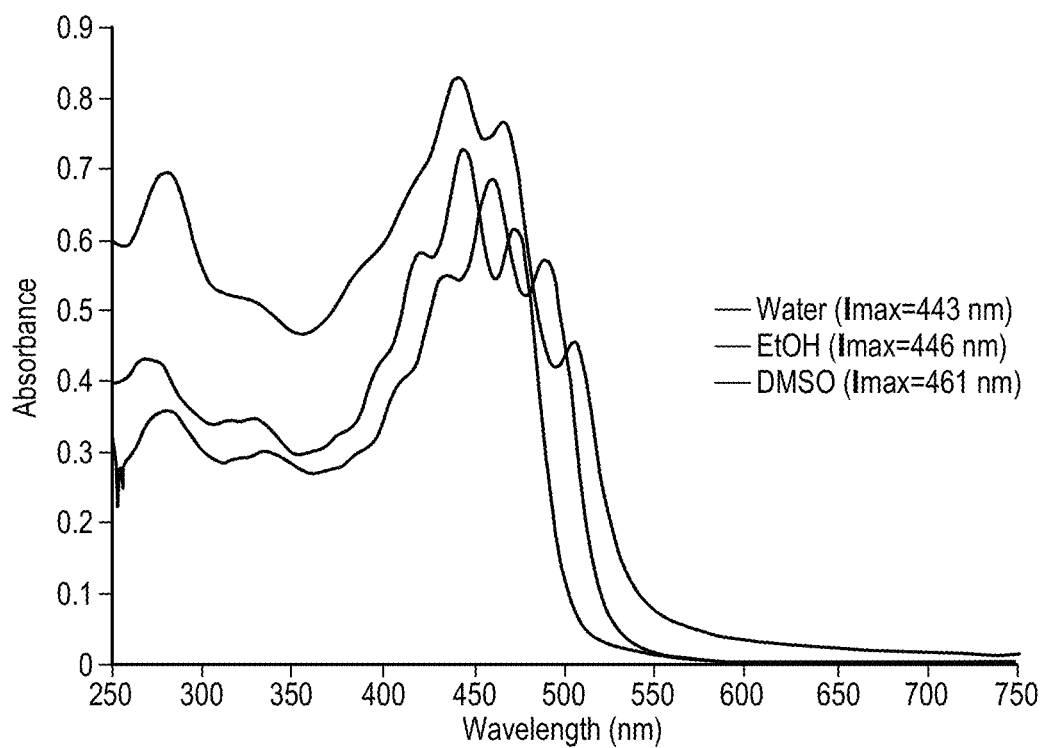
FIG. 3 depicts a UV/Vis absorption spectra of the disodium disuccinate derivative of natural source lutein in water ($\lambda_{max}$=443 nm), ethanol ($\lambda_{max}$=446 nm), and DMSO ($\lambda_{max}$=461 nm).
Figure 4:
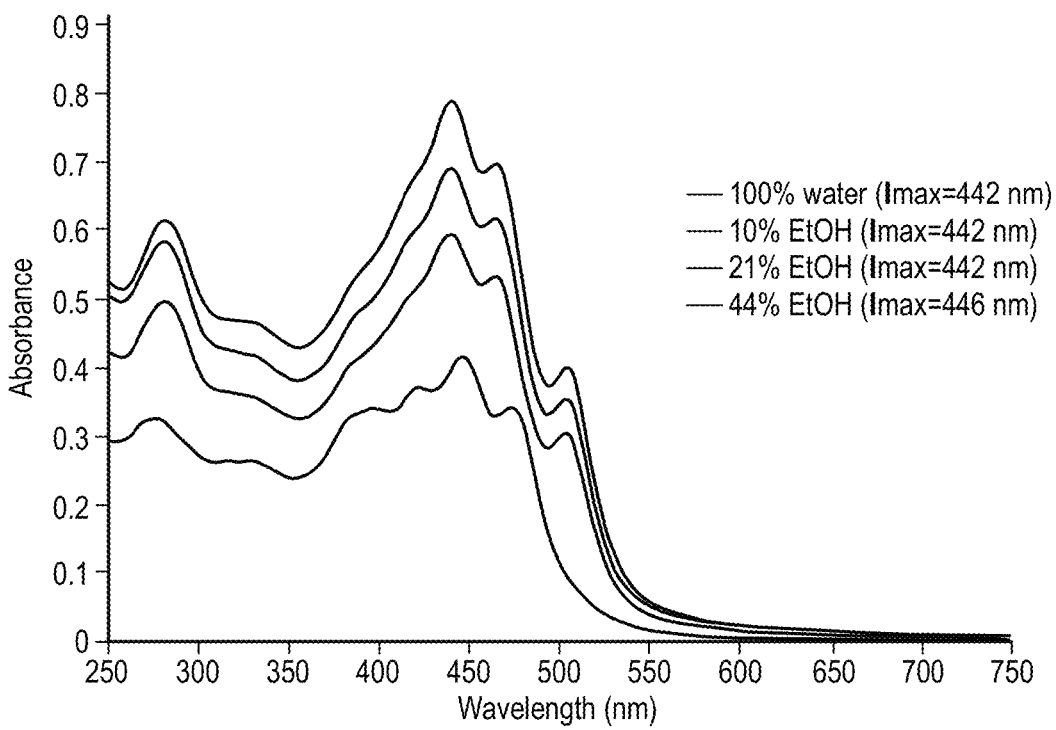
FIG. 4 depicts a UV/Vis absorption spectra of the disodium disuccinate derivative of natural source lutein in water ($\lambda_{max}$=442 nm) with increasing concentrations of ethanol.

UV-Vis spectral evaluation of the disuccinate lutein sodium salt is depicted in FIG. 2-FIG. 4. FIG. 2 depicts a time series of the UV/Vis absorption spectra of the disodium disuccinate derivative of natural source lutein in water. The $_{max}$ (443 nm) obtained at time zero did not appreciably blue-shift over the course of 24 hours, vibrational fine structure was maintained (% III/II=35%), and the spectra became only slightly hypochromic (i.e. decreased in absorbance intensity) over time, indicating minimal time-dependent supramolecular assembly (aggregation) of the card-pack type during this time period. Existence of head-to-tail (J-type) aggregation in solution cannot be ruled out.

FIG. 3 depicts a UV/Vis absorption spectra of the disodium disuccinate derivative of natural source lutein in water ($\lambda_{max}$=443 nm), ethanol ($\lambda_{max}$=446 nm), and DMSO ($\lambda_{max}$=461 nm). Spectra were obtained at time zero. A prominent cis peak is seen with a maximum at 282 nm in water. The expected bathochromic shift of the spectrum in the more polarizable solvent (DMSO) is seen (461 nm). Only a slight hypsochromic shift is seen between the spectrum in water and that in ethanol, reflecting minimal card-pack aggregation in aqueous solution. Replacement of the main visible absorption band observed in EtOH by an intense peak in the near UV region—narrow and displaying no vibrational fine structure—is not observed in the aqueous solution of this highly water-dispersible derivative, in comparison to the spectrum of pure lutein in an organic/water mixture.

FIG. 4 depicts a UV/Vis absorption spectra of the disodium disuccinate derivative of natural source lutein in water ($\lambda_{max}$=442 nm) with increasing concentrations of ethanol. The $\lambda_{max}$ increases to 446 nm at an EtOH concentration of 44%, at which point no further shift of the absorption maximum occurs (i.e. a molecular solution has been achieved), identical to that obtained in 100% EtOH (See FIG. 3).

UV-Vis spectral evaluation of the diphosphate lutein sodium salt is depicted in FIG. 5-FIG. 7. FIG. 5 depicts a time series of the UV/Vis absorption spectra of the disodium diphosphate derivative of natural source lutein in water. Loss of vibrational fine structure (spectral distribution beginning to approach unimodality) and the blue-shifted lambda max relative to the lutein chromophore in EtOH suggested that card-pack aggregation was present immediately upon solvation. The $_{max}$ (428 nm) obtained at time zero did not appreciably blue-shift over the course of 24 hours, and the spectra became slightly more hypochromic over time (i.e. decreased in absorbance intensity), indicating additional time-dependent supramolecular assembly (aggregation) of the card-pack type during this time period. This spectrum was essentially maintained over the course of 24 hours (compare with FIG. 2, disuccinate lutein sodium salt).

FIG. 6 depicts a UV/Vis absorption spectra of the disodium diphosphate derivative of natural source lutein in 95% ethanol ($\lambda_{max}$=446 nm), 95% DMSO ($\lambda_{max}$=459 nm), and water ($\lambda_{max}$=428 nm). A red-shift was observed ($\lambda_{max}$ to 446 nm), as was observed with the disuccinate derivate. Wetting of the diphosphate lutein derivative with a small amount of water was required to obtain appreciable solubility in organic solvent (e.g. EtOH and DMSO). Spectra were obtained at time zero. The expected bathochromic shift (in this case to 459 nm) of the spectrum in the more polarizable solvent (95% DMSO) is seen. Increased vibrational fine structure and red-shifting of the spectra were observed in the organic solvents.

FIG. 7 depicts a UV/Vis absorption spectra of the disodium diphosphate derivative of natural source lutein in water ($\lambda_{max}$=428 nm) with increasing concentrations of ethanol. Concentration of the derivative was held constant for each increased concentration of EtOH in solution. The $\lambda_{max}$ increases to 448 nm at an EtOH concentration of 40%, at which no further shift of the absorption maximum occurs (i.e. a molecular solution is reached).

Direct Superoxide Anion Scavenging by EPR Spectroscopy

Figure 8:
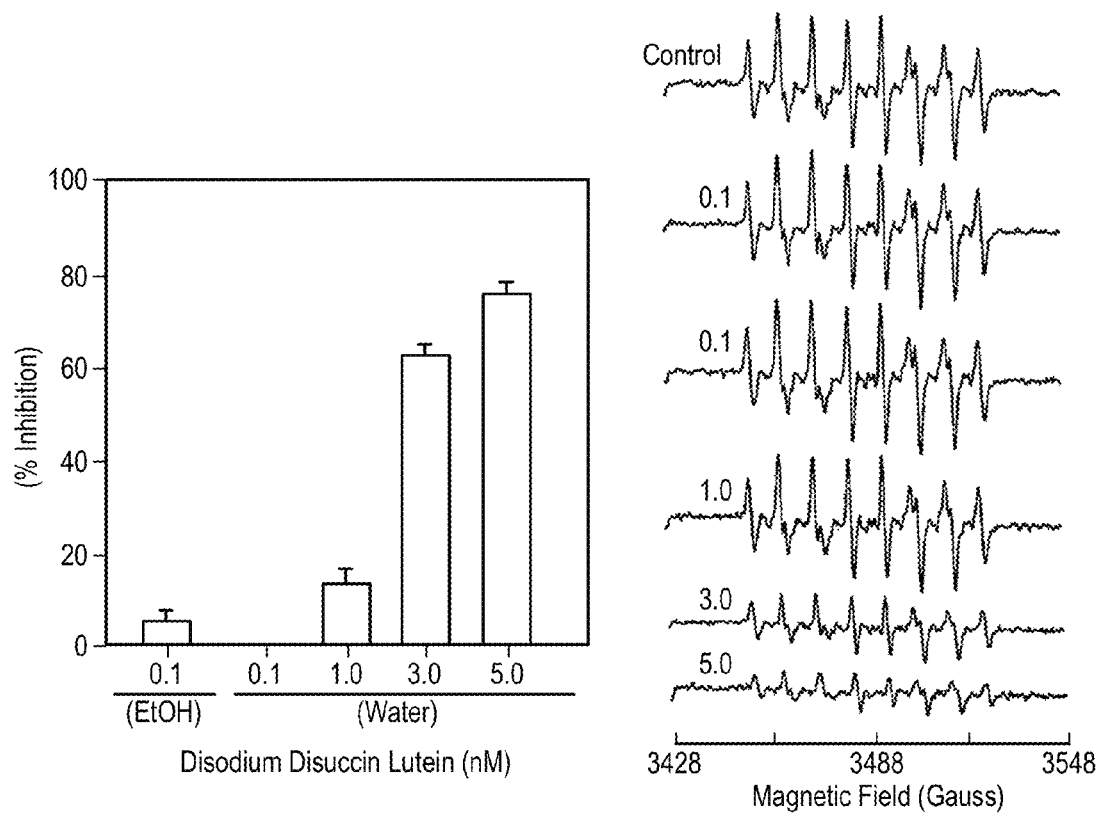
FIG. 8 depicts a mean percent inhibition (±SEM) of superoxide anion signal as detected by DEPMPO spin-trap by the disodium disuccinate derivative of natural source lutein (tested in water).

The mean percent inhibition of superoxide anion signal (±SEM) as detected by DEPMPO spin-trap by the disodium disuccinate derivative of natural source lutein (tested in water) is shown in FIG. 8. A 100 µM formulation (0.1 mM) was also tested in 40% EtOH, a concentration shown to produce a molecular (i.e. non-aggregated) solution. As the concentration of the derivative increased, inhibition of superoxide anion signal increased in a dose-dependent manner. At 5 mM, approximately ¾ (75%) of the superoxide anion signal was inhibited. No significant scavenging (0% inhibition) was observed at 0.1 mM in water. Addition of 40% EtOH to the derivative solution at 0.1 mM did not significantly increase scavenging over that provided by the EtOH vehicle alone (5% inhibition). The millimolar concentration scavenging by the derivative was accomplished in water alone, without the addition of organic co-solvent (e.g., acetone, EtOH), heat, detergents, or other additives. This data suggested that card-pack aggregation for this derivative was not occurring in aqueous solution (and thus limiting the interaction of the aggregated carotenoid derivative with aqueous superoxide anion).

Figure 9:
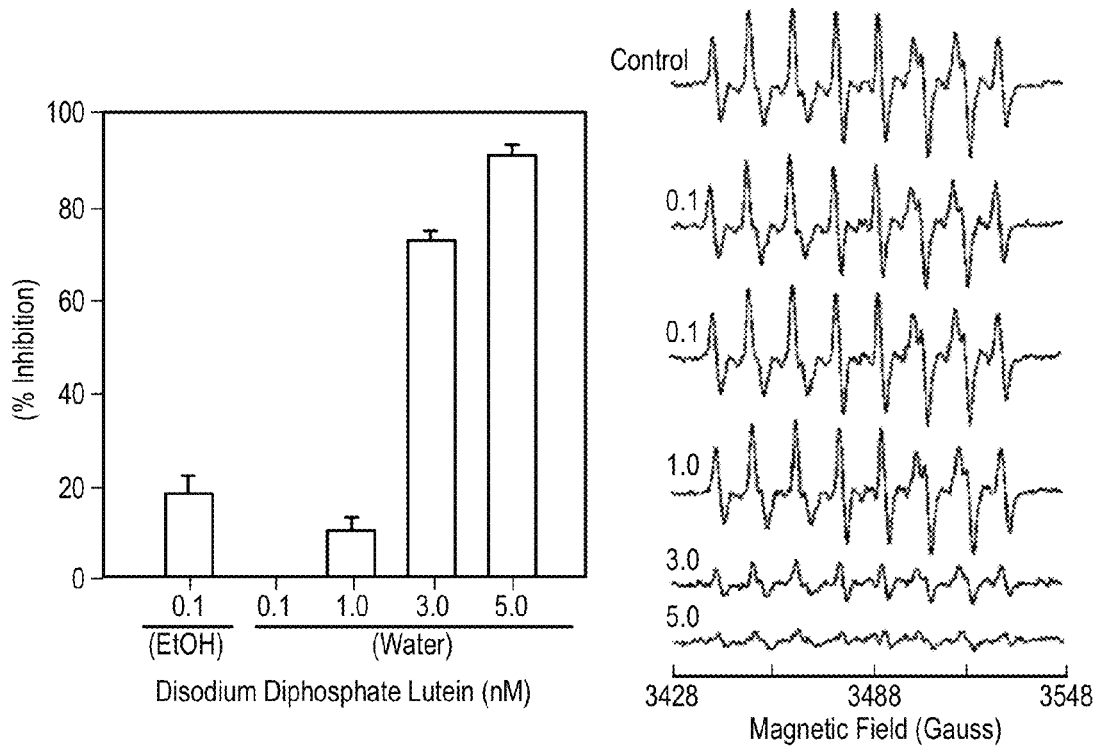
FIG. 9 depicts a mean percent inhibition (±SEM) of superoxide anion signal as detected by DEPMPO spin-trap by the disodium diphosphate derivative of natural source lutein (tested in water).

The mean percent inhibition of superoxide anion signal (±SEM) as detected by DEPMPO spin-trap by the disodium diphosphate derivative of natural source lutein (tested in water) is shown in FIG. 9. A 100 µM formulation (0.1 mM) was also tested in 40% EtOH, a concentration also shown to produce a molecular (i.e. non-aggregated) solution of this derivative. As the concentration of the derivative increased, inhibition of the superoxide anion signal increased in a dose-dependent manner. At 5 mM, slightly more than 90% of the superoxide anion signal was inhibited (versus 75% for the disuccinate lutein sodium salt). As for the disuccinate lutein sodium salt, no apparent scavenging (0% inhibition) was observed at 0.1 mM in water. However, a significant increase over background scavenging by the EtOH vehicle (5%) was observed after the addition of 40% EtOH, resulting in a mean 18% inhibition of superoxide anion signal. This suggested that disaggregation of the compound lead to an increase in scavenging ability by this derivative, pointing to slightly increased scavenging ability of molecular solutions of the more water-dispersible diphosphate derivative relative to the disuccinate derivative. Again, the millimolar concentration scavenging by the derivative was accomplished in water alone, without the addition of organic co-solvent (e.g., acetone, EtOH), heat, detergents, or other additives.

TABLE 1

Descriptive statistics of mean % inhibition of superoxide anion signal for aqueous and ethanolic (40%) formulations of disodium disuccinate derivatives of natural source lutein tested in the current study. Sample sizes of 3 were evaluated for each formulation, with the exception of natural source lutein in 40% EtOH stock solution (N = 1). Mean % inhibition did not increase over background levels until sample concentration reached 1 mM in water; likewise, addition of 40% EtOH at the 0.1 mM concentration did not increase scavenging over background levels attributable to the EtOH vehicle (mean = 5% inhibition).

| Sample | Solvent | Concentration | N | Mean (% inhibition) | S.D. | SEM | Min | Max | Range |
|---|---|---|---|---|---|---|---|---|---|
| Lutein Disuccinate Sodium Salt | 40% EtOH | 0.1 mM | 3 | 5.0 | 4.4 | 2.5 | 0 | 8 | 8 |
| Lutein Disuccinate Sodium Salt | Water | 0.1 mM | 1 | 0.0 | ND | ND | 0 | 0 | 0 |
| Lutein Disuccinate Sodium Salt | Water | 1.0 mM | 3 | 13.0 | 5.6 | 3.2 | 8 | 19 | 11 |
| Lutein Disuccinate Sodium Salt | Water | 3.0 mM | 3 | 61.7 | 4.0 | 2.3 | 58 | 66 | 8 |
| Lutein Disuccinate Sodium Salt | Water | 5.0 mM | 3 | 74.7 | 4.5 | 2.6 | 70 | 79 | 9 |

TABLE 2

Descriptive statistics of mean % inhibition of superoxide anion signal for aqueous and ethanolic (40%) formulations of disodium diphosphate derivatives of natural source lutein tested in the current study. Sample sizes of 3 were evaluated for each formulation, with the exception of lutein diphosphate in water at 100 µM (0.1 mM) where N = 1. Mean % inhibition of superoxide anion signal increased in a dose-dependent manner as the concentration of lutein diphosphate was increased in the test assay. At 100 µM in water, no inhibition of scavenging was seen. The molecular solution in 40% EtOH (mean % inhibition = 18%) was increased above background scavenging (5%) by the ethanolic vehicle, suggesting that disaggregation increased scavenging at that concentration. Slightly increased scavenging (on a molar basis) may have been obtained with the diphosphate derivative in comparison to disuccinate derivative (see Table 1 and FIG. 8).

| Sample | Solvent | Concentration | N | Mean (% inhibition) | S.D. | SEM | Min | Max | Range |
|---|---|---|---|---|---|---|---|---|---|
| Lutein $(PO_4)_2$ Na Salt | 40% EtOH | 0.1 mM | 3 | 18.0 | 7.0 | 4.0 | 11 | 25 | 14 |
| Lutein $(PO_4)_2$ Na Salt | Water | 0.1 mM | 1 | 0.0 | ND | ND | 0 | 0 | 0 |
| Lutein $(PO_4)_2$ Na Salt | Water | 1.0 mM | 3 | 9.3 | 3.5 | 2.0 | 6 | 13 | 7 |
| Lutein $(PO_4)_2$ Na Salt | Water | 3.0 mM | 3 | 72.3 | 3.1 | 1.8 | 69 | 75 | 6 |
| Lutein $(PO_4)_2$ Na Salt | Water | 5.0 mM | 3 | 91.0 | 2.6 | 1.5 | 88 | 93 | 5 |

In the current study, facile preparations of the disodium disuccinate and tetrasodium phosphate esters of natural source (RRR) lutein are described. These asymmetric C40 carotenoid derivatives exhibited aqueous dispersibility of 2.85 and 29.27 mg/mL, respectively. Evidence for both cardpack (H-type) and head-to-tail (J-type) supramolecular assembly was obtained with UV-Vis spectroscopy for the aqueous solutions of these compounds. Electronic paramagnetic spectroscopy of direct aqueous superoxide scavenging by these derivatives demonstrated nearly identical dose-dependent scavenging profiles, with slightly increased scavenging noted for the diphosphate derivative. In each case, scavenging in the millimolar range was observed. These results show that as parenteral soft drugs with aqueous radical scavenging activity, both compounds are useful in those clinical applications in which rapid and/or intravenous delivery is desired for the desired therapeutic effect(s).

Experimental Methods

Preparation of Stock Solutions of Cardax™ (DDA) and Placebo for Injection.

DDA was from a lot previously characterized in detail (Frey et al. 2004). The crystalline material was dissolved directly in sterile-filtered (0.2 micron Millipore® filter) deionized water. The maximum aqueous dispersibility of DDA is slightly greater than 10 mM (8.64 mg/ml). Sterile sodium chloride solution (0.9%) for injection was used as the treatment (placebo) for the control group. DDA or placebo solution was administered by slow ear vein injection using an infusion pump set at 1 ml/min.

Dosing Schedule.

Male New Zealand white rabbits (2.3-2.6 kg) were assigned randomly to two separate groups. Each animal received DDA aqueous formulation (50 mg/kg), or an equal volume of sterile NaCl solution, once per day intravenously. The dose of DDA was selected based on the findings of previous investigations in which it was determined that a dosing regimen over four days produced statistically significant myocardial salvage in Sprague-Dawley rats (41% mean salvage at 50 mg/kg) and mongrel canines (68% mean salvage at 50 mg/kg) after ischemia and reperfusion (Gross and Lockwood, 2004; Gross and Lockwood, In Press). The animals in each group received the respective treatments on each of four consecutive days, with the experimental protocol being initiated on fifth day.

Surgical Preparation and Experimental Occlusion.

One day after the last treatment (DDA or placebo), rabbits were anesthetized with a combination of xylazine (3.0 mg/kg) and ketamine (35 mg/kg) administered intramuscularly, followed by an intravenous injection of sodium pentobarbital (15 mg/kg). An endotracheal tube was inserted and the animals were placed on a positive pressure ventilator (Harvard Apparatus, Cambridge, Mass.). The right jugular vein was cannulated for blood sampling and the right carotid artery was instrumented with a Millar catheter micro-tip pressure transducer (Millar Instruments Inc., Houston, Tex.). The Millar catheter transducer was positioned immediately above the aortic valves to monitor aortic blood pressure. The lead II electrocardiogram was monitored throughout the protocol. A left thoracotomy and pericardiotomy were performed, followed by identification of the left anterior descending coronary artery. A silk suture (3-0; Genzyme Corporation, Fall River, Mass.) was passed under the artery and around a short length of polyethylene tubing. Simultaneous downward displacement of the polyethylene tubing while applying upward traction on the suture resulted in occlusion of the coronary artery and cessation of regional blood flow. Coronary artery occlusion was maintained for 30 min after which time reperfusion was initiated by withdrawing the polyethylene tubing. Regional myocardial ischemia was verified by the presence of a zone of cyanosis in the area of distribution of the occluded vessel and by changes in the electrocardiogram consistent with the presence of transmural regional myocardial ischemia (ST-segment elevation).

Experimental Protocol.

The animals were allowed to stabilize for 15 min before beginning the protocol that involved both a vehicle control and a DDA-treated group. Cessation of coronary blood flow was maintained for 30 minutes after which the ligature was removed and the heart was allowed to reperfuse for a period of three hours before terminating the study.

Tetrazolium Method to Determine Infarct Size.

At the completion of the 3 hr reperfusion period, the hearts were removed, the aorta was cannulated, and the coronary vascular bed was perfused on a Langendorff apparatus with Krebs-Henseleit buffer at a constant flow of 30 to 32 ml/min. The hearts were perfused with buffer for 10 min to clear the vascular compartment of plasma and blood cellular elements. Fifty milliliters of a 1% solution of triphenyltetrazolium chloride (TTC, Sigma, St. Louis, Mo.) in phosphate buffer (pH 7.4, 37° C.) was perfused through the heart. TTC demarcates the non-infarcted myocardium within the area at risk with a brick red color, indicating the presence of a formazan precipitate resulting from reduction of TTC by dehydrogenases present in viable myocardial tissue. Irreversibly injured tissue, lacking cytosolic dehydrogenases, is unable to form the formazan precipitate and appears pale yellow. Upon completion of the TTC infusion, the left anterior descending coronary artery was ligated at the site identical to that ligated during the induction of regional myocardial ischemia. The perfusion pump was stopped, and 3 ml of a 0.25% solution of Evan's Blue was injected slowly through a side-arm port connected to the aortic cannula. The dye was passed through the heart for 15 sec to ensure its uniform tissue distribution. The presence of Evan's Blue was used to demarcate the left ventricular tissue that was not subjected to regional ischemia, as opposed to the risk region. The heart was removed from the perfusion apparatus and cut into transverse sections at right angles to the vertical axis. The right ventricle, apex, and atrial tissue were discarded. Both surfaces of each tissue section were traced onto clear acetate sheets. The images were photocopied and enlarged, then digitized using a flatbed scanner. The areas of the normal left ventricle non-risk region, area at risk, and infarct region were determined by calculating the number of pixels occupying each area using Adobe PhotoShop software (Adobe Systems, Seattle, Wash.). Total area at risk is expressed as the percentage of the left ventricle. Infarct size is expressed as the percentage of the area at risk.

Plasma and Tissue Concentrations of Non-Esterified Free Astaxanthin.

To determine the plasma and tissue concentrations of non-esterified, free astaxanthin in blood and organs, samples were taken at the end of reperfusion in selected rabbits (n=5) treated with DDA, and determined by methods previously described (Osterlie et al., 2000). Non-esterified, free astaxanthin, in vivo, is generated after cleavage of the water-dispersible disuccinate diester to monosuccinate, and subsequently to non-esterified, free astaxanthin by the intrinsic esterase activity of serum albumin (Curry et al., 1999), or by non-specific esterase activity in plasma and solid organs (Jensen et al., 1999). Non-esterified, free astaxanthin then accumulates in myocardium and other tissues after plasma clearance in a dose-dependent manner after both oral (Showalter et al., 2004) and intravenous administration (Gross and Lockwood 2004a,b).

Measurement of Cardiac-Specific Troponin I.

Whole blood was drawn at baseline (pre-ischemia) and at the end of reperfusion for the determination of cardiac-specific troponin I (cTnI). Serum levels of the proteins were measured using a commercially available ELISA kit. Collected plasma samples were prepared from whole blood and were snap frozen in liquid nitrogen. The samples were stored at −80° C. until the day of the assay when they were thawed over ice and diluted appropriately with the sample diluent supplied with each assay kit. Determination of the target protein using a protein standard curve was performed according to standard procedure in the art.

Analysis of MAC and CRP Deposition in Tissues by Indirect Immunofluorescence.

The immunofluorescent method for detection of CRP was performed essentially as described previously (Lauver et al., 2005). Briefly, tissue samples used for infarct size determination were fixed in 10% buffered formalin immediately after the completion of the experimental protocol. The tissue samples were embedded in paraffin blocks and cut into sections of 2 μm in thickness, which were then mounted on glass slides. Two consecutive sections (mirror images) from a single heart slice were mounted on each slide. The slides were deparaffinized and subjected to antigen unmasking using a commercially available kit for this purpose (Vector Laboratories, Burlingame, Calif.). After blocking for 30 minutes, primary antibodies were incubated at room temperature in a humidity chamber for 45 minutes. One section per slide was incubated with a chicken anti-rabbit CRP antibody (5 μg/ml final concentration, Strategic BioSolutions, Newark, Del.) and the other section was incubated with a chicken anti-rabbit MAC antibody (1:2500 final dilution, developed in conjunction with Lampire Biological Laboratories, Pipersville, Pa.). Both sections were incubated with a biotinylated goat anti-chicken secondary antibody (1.5 μg/ml final concentration, Vector Laboratories) for 30 minutes. The slides were incubated with Fluorescein and Texas Red (CRP and MAC sections, respectively)-labeled streptavidin (Fluorescent Streptavidin Kit, Vector Laboratories) to visualize the proteins. ProLong Gold antifade mounting medium (Molecular Probes, Eugene, Oreg.) and coverslips were used to preserve the sections. For comparison, digital images were captured using a digital camera (Sony DKC5000; Sony Corporation of America, New York, N.Y.) connected to a Leica fluorescent stereoscope (Leica MZ FUJI) and the accompanying software (Leica Microsystems Inc., Bannockburn, Ill.). Images were analyzed using IP Lab (Scanalytics, Inc., Fairfax, Va.) software to determine mean fluorescence intensity per heart section. The sections were normalized to the amount of background on each slide. The mean intensities for three hearts in each treatment group were averaged and compared.

Assessment of Complement Inhibition.

A red blood cell (RBC) lysis assay was used to determine whether the pretreatment with DDA compared to placebo-treated animals was able to inhibit the rabbit complement system. The ex vivo analysis of complement activity is based on the C5b-9-dependent lysis of human red blood cells upon exposure to rabbit plasma. Complement-mediated RBC hemolysis was assessed by a turbidometric method described previously (Pascual et al., 1990). The hemolysis assay is an accepted method of assessing the complement titer of plasma or serum samples (Whaley, 1985). Rabbit plasma was obtained from whole blood samples drawn from rabbits that were pretreated with DDA (50 mg/kg, 4 days, n=5) or sterile 0.9% sodium chloride solution (4 days, n=5). After obtaining informed consent, human whole blood for the isolation of red blood cells was obtained by venipuncture of the forearm vein of a healthy, male donor who had not been exposed to any medication for the past seven days. The cells were washed three times in 10 ml phosphate buffered saline (PBS, pH 7.4) and diluted in PBS to achieve a final RBC concentration of $1 \times 10^8$ cells/ml. The assay was initiated by the addition of 15 μl of diluted human RBCs to 185 μl of rabbit plasma, and the light transmittance was monitored for 5 min. The final assay volume was 200 μl. One hundred percent light transmittance was set with RBCs lysed with a 1:1 mixture of rabbit plasma and deionized $H_2O$.

Statistical Analysis.

Results are expressed as the mean values±S.E.M. Parameters between the two groups were compared using the Student's t test for unpaired comparisons. P values of <0.05 and <0.01 are regarded as significant and denoted by an asterisk and double asterisk, respectively.

Example 1

Determination of Test Animal Vital Signs

Figure 11:
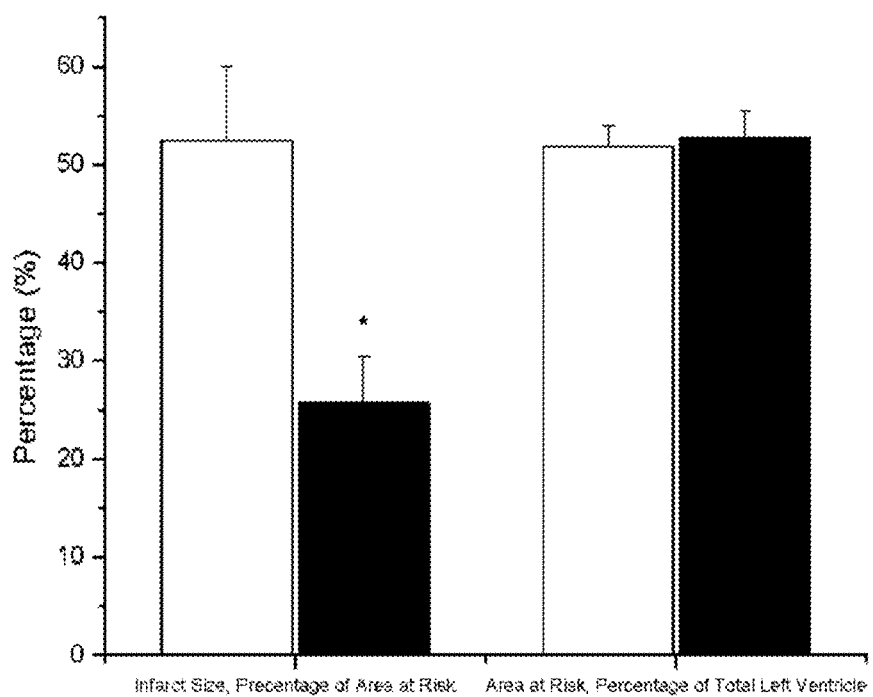
FIG. 11 depicts the effects of DDA (also known as "Cardax™") or saline on myocardial infarct size after 30 min of left anterior descending coronary artery occlusion followed by 3 h of reperfusion.

No differences in heart rate, blood pressure, or blood gases at baseline or throughout the experimental protocol performed on day 5 between the two groups was observed (data not shown). Turning to FIG. 11, no significant differences in areas at risk were observed between the animals treated with DDA or with saline, indicating that both groups were subjected to similar degrees of ischemia.

Example 2

Effect of DDA on Myocardial Infarct Size

Remaining with FIG. 11, each treatment group consisted of 9 animals in which either DDA or saline placebo was administered for 4 days before commencing the experimental protocol involving myocardial ischemia/reperfusion. The mean size of the area at risk expressed as a percentage of the total left ventricle was similar in both groups. Rabbits treated with DDA (50 mg/kg/day) exhibited significantly smaller mean infarcts expressed as a percentage of the area at risk (25.8±4.2%) compared with rabbits treated with placebo (52.5±7.5%, **p<0.01). This represented mean myocardial salvage of 51%. These results therefore demonstrate that disodium disuccinate astaxanthin treatment can significantly reduce the size of an infarct relative to the area of myocardium at risk in rabbits subjected to 30 minutes of coronary artery occlusion followed by a three hour period of reperfusion. DDA produced a mean myocardial salvage of approximately 51% when the rabbits were dosed with 50 mg/kg daily for four consecutive days. This level of salvage at the 50 mg/kg subchronic intravenous dose is intermediate between that obtained in rats (41% salvage) and mongrel dogs (68%), demonstrating appropriate pharmacokinetic scaling across several species of mammals (Gross and Lockwood, 2004); Gross and Lockwood 2004b).

Example 3

Plasma and Tissue Levels of Non-Esterified, Free Astaxanthin

Figure 12:
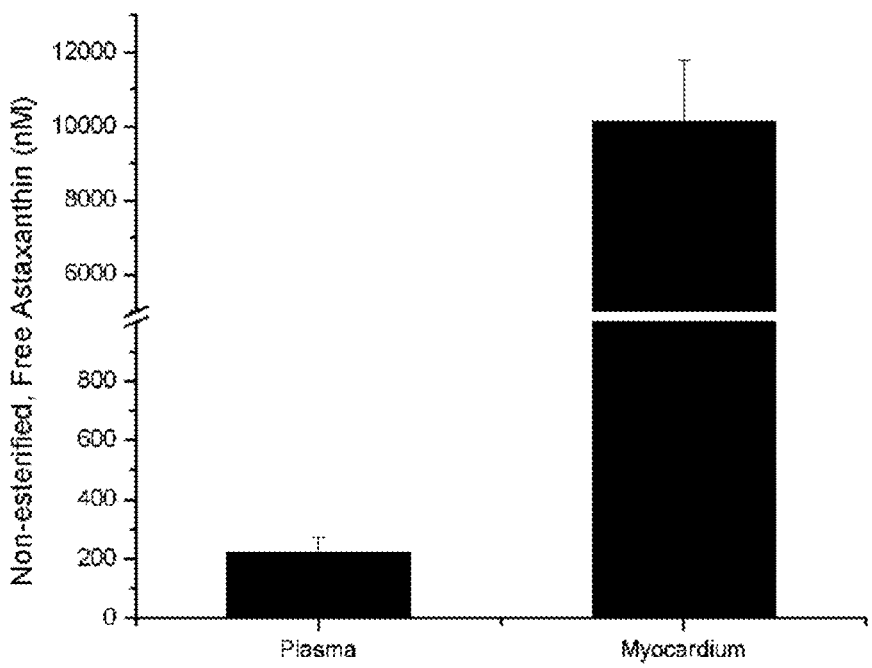
FIG. 12 Depicts the mean plasma and myocardial tissue concentrations of non-esterified, free astaxanthin (nM) in rabbits subjected to 30 min of left anterior descending coronary artery occlusion and 3 h of reperfusion, following 4 daily intravenous doses of DDA (50 mg/kg).

Turning to FIG. 12, the mean plasma concentration of non-esterified, free astaxanthin at the end of 3 hours of reperfusion is presented. Pretreatment with DDA at 50 mg/kg for 4 days resulted in a mean plasma concentration of 222±51 nM. However, the mean myocardial tissue concentration of DDA was several orders of magnitude greater than that observed in the plasma (FIG. 12), revealing highly favorable mean myocardium/serum ratios in the rabbit after intravenous subchronic administration. We were able to achieve plasma concentrations of non-esterified astaxanthin that were roughly equal to those previously found in other species using the same intravenous dosage regimen (Gross and Lockwood, 2004; Gross and Lockwood, In Press). We also observed a marked accumulation of non-esterified astaxanthin in the myocardium (mean>10 µM) in the rabbits utilized in this study. Rapid plasma clearance of free astaxanthin, and excellent myocardium- and hepatic/serum ratios had previously been demonstrated after oral administration of this compound to black mice (Showalter et al. 2004). The current results further demonstrate the favorable pharmacokinetic profile of DDA in mammals.

Example 4

Serum Levels of Cardiac-Specific Troponin I

Figure 13:
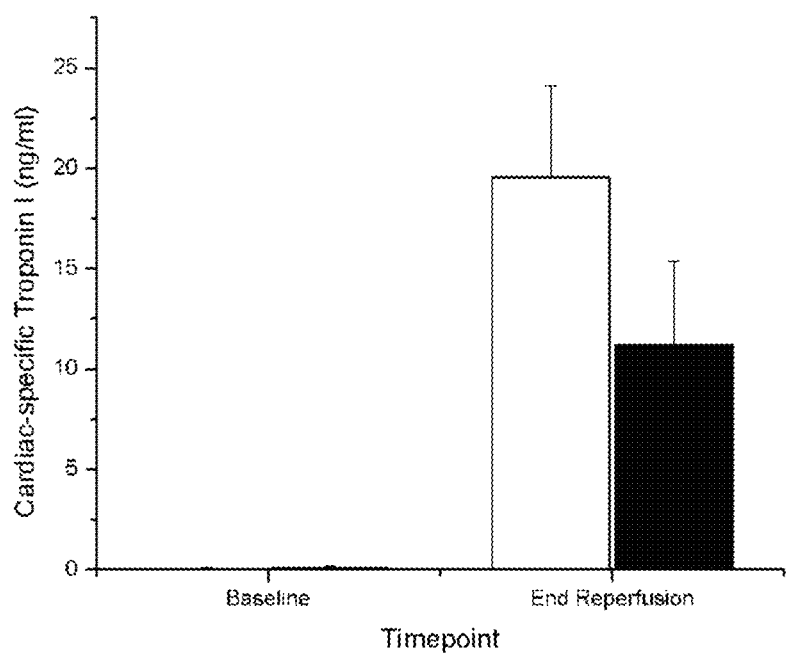
FIG. 13 Depicts the effect of DDA administration on serum levels of a molecular marker of cardiac damage.

Turning to FIG. 13, the mean serum concentrations of cTnI were similar at baseline (pre-ischemia) in both treatment groups. DDA treated rabbits exhibited a lower mean cTnI concentration at the end of reperfusion as compared with vehicle controls. These results therefore demonstrate that treatment of a subject with disodium disuccinate astaxanthin can result in a mean reduction in the circulating concentration of the biochemical injury marker, cardiac-specific troponin I. Although the results did not achieve statistical significance, clear evidence of a downward trend in this serum marker of irreversible myocardial tissue injury was obtained. The reduced statistical power observed in this study versus those obtained in prior studies for this marker (Lauver et al. 2005) may have been due to the curtailed period of reperfusion in the current study. In other words, it is likely that statistically significant differences in peak plasma cTnI may be achieved by prolonging cardiac reperfusion time.

Example 5

Immunofluorescence

Along with the generation of reactive oxygen species, the activation of the complement system serves an integral role in myocardial reperfusion injury (Lucchesi, 1994). Therefore we sought to investigate the effects of DDA on the tissue deposition of CRP and the terminal complex (C5b-9; MAC), both of which are recruited to an deposited on tissue undergoing ischemia/reperfusion-associated inflammation.

Figure 14:
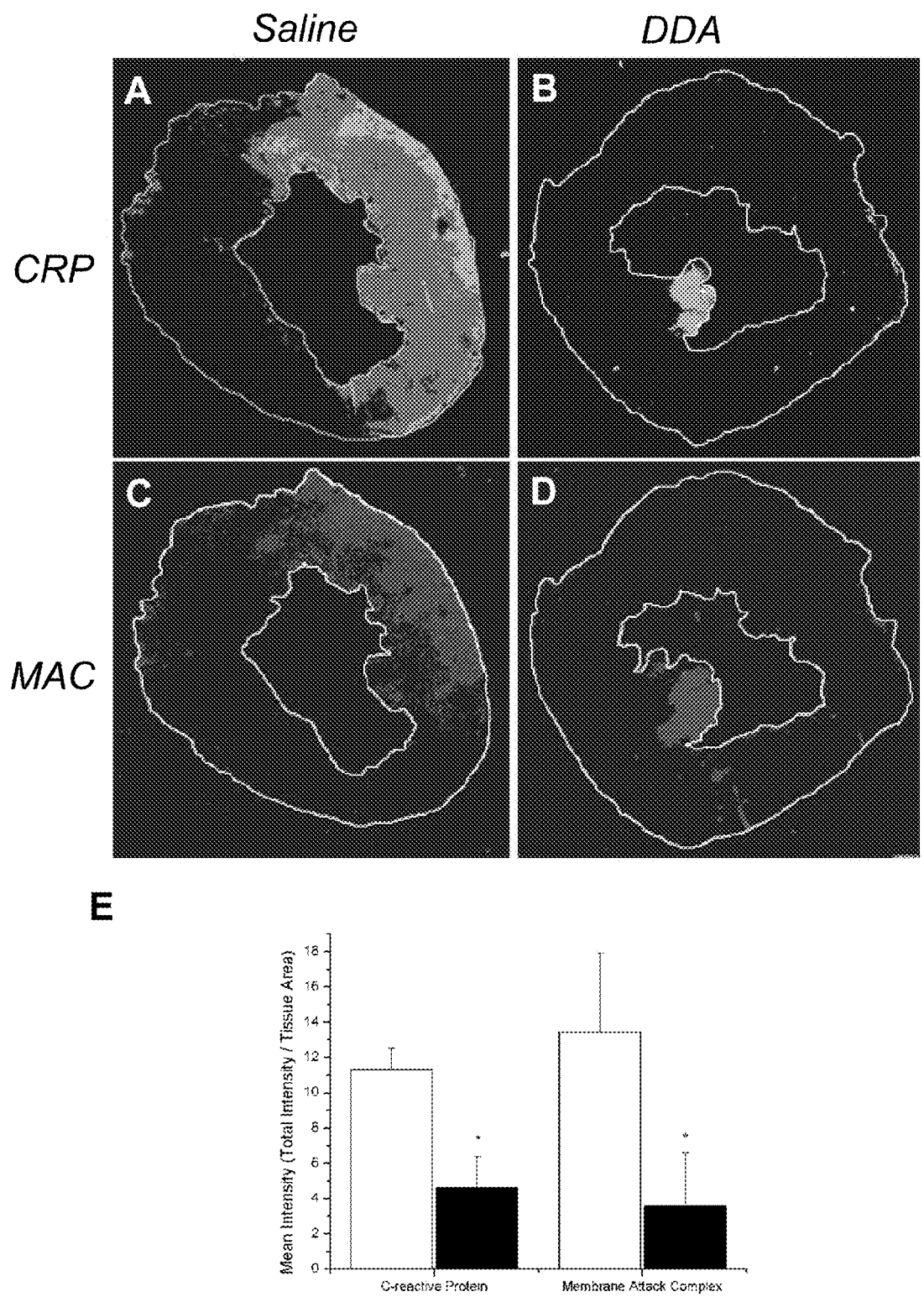
FIG. 14 shows representative fluorescent images of a heart from a saline control rabbit (A and C) and a rabbit treated with DDA (B and D) after 30 min of ischemia and 3 h of reperfusion.

Left ventricular tissue sections obtained from hearts that had been treated with saline or with DDA, then subjected to 30 min of regional ischemia, followed by 3 h of reperfusion were subjected to indirect immunofluorescence analysis to the detect tissue deposition of CRP and the MAC. Turning to FIG. 14, heart sections taken from the infarct region in animals treated with saline (panels A and C, respectively) demonstrated bright fluorescence with both anti-CRP (green) and anti-MAC (red) antibodies, indicating the deposition of both proteins in the area of infarction. Conversely, hearts treated with DDA (panels B and D, respectively) exhibited significantly reduced fluorescence, indicative of a reduction in the deposition of CRP and MAC in the infarct region. The mean intensity of fluorescence (panel E) in heart sections obtained after treatment with DDA was significantly (*$p<0.05$) lower in tissue sections stained for either CRP or MAC. These results therefore demonstrate that treatment of a subject with disodium disuccinate astaxanthin can significantly reduce the deposition of CRP and the MAC in damaged tissue.

Example 5

Inhibition of Complement Activation

Figure 15:
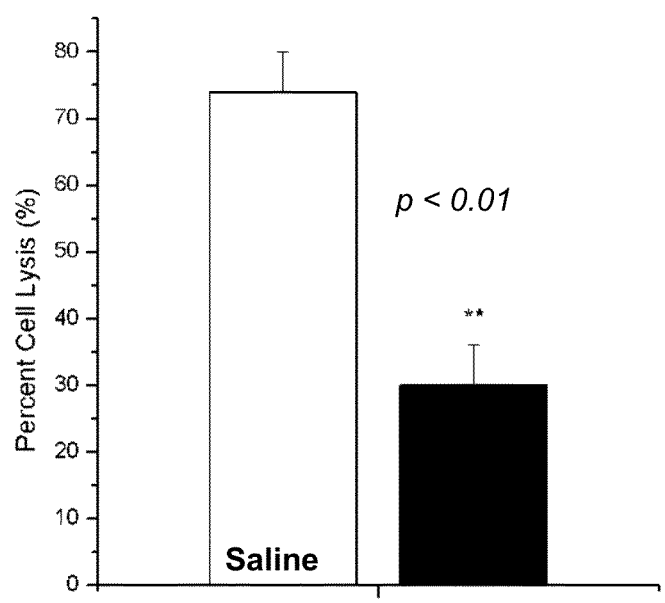
FIG. 15 shows a complement-mediated red blood cell (RBC) hemolysis assay conducted after DDA administration using human erythrocytes as the target cell and rabbit plasma drawn after reperfusion as the source of complement proteins.

The erythrocyte hemolysis assay was used to determine the ability of DDA to inhibit the activation of the complement system (FIG. 15). DDA significantly attenuated complement-mediated erythrocyte lysis after the 3 h reperfusion period. The hemolytic response was followed for 300 seconds. Values are expressed as mean±S.E.M.; saline group, n=5 (white bars); DDA group, n=5 (black bars);  $p<0.01$ versus saline. Pretreatment with DDA (50 mg/kg, 4 days) significantly reduced ($p<0.01$) mean rabbit plasma-induced human erythrocyte hemolysis compared to plasma from placebo treated rabbits.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

REFERENCES

Black et al., "C-Reactive Protein", *Journal of Biological Chemistry*, Vol. 279, 2004, pp 48487-48494

Bolli R, Jeroudi M O, Patel B S, Aruoma O I, Halliwell B, Lai E K and McCay P B (1989) Marked reduction of free radical generation and contractile dysfunction by antioxidant therapy begun at the time of reperfusion. Evidence that myocardial "stunning" is a manifestation of reperfusion injury. *Circ Res* 65:607-622.

Britton G (1995) Structure and properties of carotenoids in relation to function. *Faseb J* 9:1551-1558.

Cantrell A, McGarvey D J, Truscott T G, Rancan F and Bohm F (2003) Singlet oxygen quenching by dietary carotenoids in a model membrane environment. *Arch Biochem Biophys* 412:47-54.

Cardounel A J, Dumitrescu C, Zweier J L and Lockwood S F (2003) Direct superoxide anion scavenging by a disodium disuccinate astaxanthin derivative: Relative efficacy of individual stereoisomers versus the statistical mixture of stereoisomers by electron paramagnetic resonance imaging. *Biochem Biophys Res Commun* 307:704-712.

de Córdoba et al., "The Human Complement Factor H: Functional Roles, Genetic Variations and Disease Associations" *Molecular Immunology* Vol. 41, 2004, pp. 355-367

Curry S, Brick P and Franks N P (1999) Fatty acid binding to human serum albumin: new insights from crystallographic studies. *Biochim Biophys Acta* 1441:131-140.

de Beer F C, Hind C R, Fox K M, Allan R M, Maseri A and Pepys M B (1982) Measurement of serum C-reactive protein concentration in myocardial ischaemia and infarction. *Br Heart J* 47:239-243.

Devasagayam T P, Werner T, Ippendorf H, Martin H D and Sies H (1992) Synthetic carotenoids, novel polyene polyketones and new capsorubin isomers as efficient quenchers of singlet molecular oxygen. *Photochem Photobiol* 55:511-514.

Diaz Padilla N, Bleeker W K, Lubbers Y, Rigter G M, Van Mierlo G J, Daha M R and Hack C E (2003) Rat C-reactive protein activates the autologous complement system. *Immunology* 109:564-571.

Edwards et al., "Complement Factor H Polymorphism and Age-Related Macular Degeneration" published online 10 Mar. 2005; 10.1126/science.1110189

Funkhouser T A and Vik D P (1999) Complement receptor type 1 gene regulation: retinoic acid and cytosine arabinoside increase CR1 expression. *Scand J Immunol* 49:21-28.

Gross G J and Lockwood S "Acute and chronic administration of disodium disuccinate astaxanthin (Cardax™) produces marked cardioprotection in dog hearts" *Molecular and Cellular Biochemistry*, Vol. 272, 2006, pp. 221-227.

Gross G J and Lockwood S F (2004) Cardioprotection and myocardial salvage by a disodium disuccinate astaxanthin derivative (Cardax). *Life Sci* 75:215-224.

Gross G J et al. "Seven day oral supplementation with Cardax™ (disodium disuccinate astaxanthin) provides significant cardioprotection and reduces oxidative stress in rats" *Molecular and Cellular Biochemistry* Vol. 283, 2006, pp. 23-30.

Haines et al., "Complement Factor H Variant Increases the Risk of Age-Related Macular Degeneration" published online 10 Mar. 2005; 10.1126/science.1110359

Jensen S K, Engberg R M and Hedemann M S (1999) All-rac-alpha-tocopherol acetate is a better vitamin E source than all-rac-alpha-tocopherol succinate for broilers. *J Nutr* 129:1355-1360.

Jolly S R, Kane W J, Bailie M B, Abrams G D and Lucchesi B R (1984) Canine myocardial reperfusion injury. Its reduction by the combined administration of superoxide dismutase and catalase. *Circ Res* 54:277-285.

Kilgore K S, Friedrichs G S, Johnson C R, Schasteen C S, Riley D P, Weiss R H, Ryan U and Lucchesi B R (1994) Protective effects of the SOD-mimetic SC-52608 against ischemia/reperfusion damage in the rabbit isolated heart. *J Mol Cell Cardiol* 26:995-1006

Klein et al., "Complement Factor H Polymorphism in Age-Related Macular Degeneration" published online 10 Mar. 2005; 10.1126/science.1109557

Lauver D A, Booth E A, White A J, Poradosu E and Lucchesi B R (2005) Sulodexide Attenuates Myocardial Ischemia/Reperfusion Injury and the Deposition of C-Reactive Protein in Areas of Infarction without Affecting Hemostasis. *J Pharmacol Exp Ther* 312:794-800.

Lucchesi B R (1994) Complement, neutrophils and free radicals: mediators of reperfusion injury. *Arzneimittelforschung* 44:420-432.

Nijmeijer R, Lagrand W K, Lubbers Y T, Visser C A, Meijer C J, Niessen H W and Hack C E (2003) C-reactive protein activates complement in infarcted human myocardium. *Am J Pathol* 163:269-275.

Osterlie M, Bjerkeng B and Liaaen-Jensen S (2000) Plasma appearance and distribution of astaxanthin E/Z and R/S isomers in plasma lipoproteins of men after single dose administration of astaxanthin(1). *J Nutr Biochem* 11:482-490.

Park J L and Lucchesi B R (1999) Mechanisms of myocardial reperfusion injury. *Ann Thorac Surg* 68:1905-1912.

Pascual M, Catana E, Spertini F, Macon K, Volanakis J E and Schifferli J A (1990) A monoclonal antibody which blocks the function of factor D of human complement. *J Immunol Methods* 127:263-269.

Ridker et al. "C-Reactive Protein Levels and Outcomes after Statin Therapy" *The New England Journal of Medicine*, 2005, 352, pp 20-28.

Ridker "C-Reactive Protein, Inflammation and Cardiovascular Disease—Clinical Update" Current Issues in Cardiologuy, Vol. 32(3), 2005, pp. 384-386.

Showalter L A, Weinman S A, Osterlie M and Lockwood S F (2004) Plasma appearance and tissue accumulation of non-esterified, free astaxanthin in C57BL/6 mice after oral dosing of a disodium disuccinate diester of astaxanthin (Heptax). *Comp Biochem Physiol C Toxicol Pharmacol* 137: 227-236.

Simonyi M, Bikadi Z, Zsila F and Deli J (2003) Supramolecular exciton chirality of carotenoid aggregates. *Chirality* 15:680-698.

Tanhehco E J, Yasojima K, McGeer P L, Washington R A and Lucchesi B R (2000) Free radicals upregulate complement expression in rabbit isolated heart. *Am J Physiol Heart Circ Physiol* 279:H195-201.

Venugopal et al. "Macrophage Conditioned Medium Induces the Expression of C-Reactive Protein in Human Aortic Endothelial Cells: Potential for Paracrine/Autocrine Effects" American Journal of Pathology, 2005, 166(4), pp 1265-1271.

Volanakis J E (1982) Complement activation by C-reactive protein complexes. *Ann N Y Acad Sci* 389:235-250.

Whaley K (1985) *Methods in Complement for Clinical Immunologists.* Churchill Livingstone, New York.

Yasojima K, Schwab C, McGeer E G and McGeer P L (1998) Human heart generates complement proteins that are upregulated and activated after myocardial infarction. *Circ Res* 83:860-869.

Yeh E T, Anderson H V, Pasceri V and Willerson J T (2001) C-reactive protein: linking inflammation to cardiovascular complications. *Circulation* 104:974-975.

Ytrehus K, Myklebust R, Olsen R and Mjos O D (1987) Ultrastructural changes induced in the isolated rat heart by enzymatically generated oxygen radicals. *J Mol Cell Cardiol* 19:379-389.

Zsila F, Simonyi M and Lockwood S F (2003) Interaction of the disodium disuccinate derivative of meso-astaxanthin with human serum albumin: from chiral complexation to self-assembly. *Bioorg Med Chem Lett* 13:4093-4100.

What is claimed is:

1. A method of reducing tissue damage associated with an inflammatory response in a subject comprising administering to a subject who would benefit from such treatment a therapeutically effective amount of a pharmaceutically acceptable formulation comprising a synthetic carotenoid analog or a carotenoid derivative having the structure;

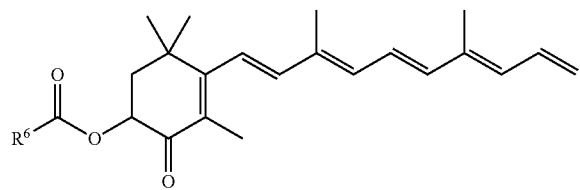

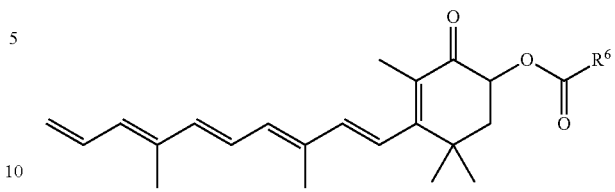

wherein each $R^6$ is independently:
-alkyl-$N(R^7)_2$; -aryl-$N(R^7)_2$; -alkyl-$N^+(R^7)_3$; -aryl-$N^+(R^7)_3$; -alkyl-$CO_2R^8$; -aryl-$CO_2R^8$, -alkyl-$CO_2^-$; -aryl-$CO_2^-$; or a peptide; where $R^7$ is hydrogen, alkyl, or aryl;
where $R^8$ is hydrogen.

2. The method of claim 1, further comprising administering to the subject at least one anti-inflammatory drug.

3. The method of claim 2, wherein at least one of the anti-inflammatory drugs are selected from the list consisting of cortisol; hydrocortisone; prednisone;

prednisolone; methylprednisolone; meprednisone; triamcicolone; paramethasone;

fluprednisolone; betamethasone; dexamethasone; fludrocortisone; aspirin; diclofenac; diflunisal;

etodolac; fenoprofen; floctafenine; flurbiprofen; ibuprofen; indomethacin; ketorolac; ketoprofen;

meclofenamate; mefenamic acid; meloxicam; nabumetone; naproxen; nimesulide; oxaprozin;

phenylbutazone; piroxicam; salsalate; sulindac; tenoxicam; tiaprofenic acid; tolmetin; celecoxib;

rofecoxib; etoricoxib; and valdecoxib.

4. The method of claim 1, wherein the formulation is administered prior to the onset of an inflammatory response.

5. The method of claim 1, wherein the composition is administered orally.

6. The method of claim 1, wherein the composition is administered parenterally.

7. The method of claim 1, wherein the composition is administered as an aqueous solution.

8. The method of claim 1, wherein the composition is administered as an aqueous dispersion.

9. The method of claim 1, wherein the composition is administered intravenously.

10. The method of claim 1, wherein the composition is administered intravascularly.

11. The method of claim 1, wherein the composition is administered by intramuscular injection.

12. The method of claim 1, wherein the composition is administered subcutaneously.

13. The method of claim 1, wherein the composition is administered transdermally.

14. The method of claim 1, wherein the composition comprises one or more carotenoid derivatives or analogs having the structure:

101 102
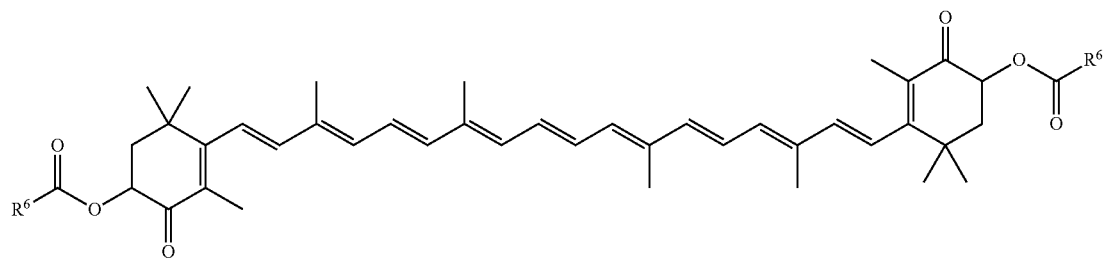
wherein $R^6$ is -alkyl-N($R^7$)$_2$ or -alkyl-N$^+$($R^7$)$_3$ and where $R^7$ is hydrogen or alkyl.
15. The method of claim 1, wherein the inflammatory response is caused by an inflammatory disorder.
* * * * *